US006828450B2

(12) United States Patent
Hua et al.

(10) Patent No.: US 6,828,450 B2
(45) Date of Patent: Dec. 7, 2004

(54) TRIPTYCENE ANALOGS

(75) Inventors: Duy Hua, Manhattan, KS (US); Jean-Pierre Perchellet, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 218 days.

(21) Appl. No.: 09/974,716

(22) Filed: Oct. 9, 2001

(65) Prior Publication Data

US 2002/0091163 A1 Jul. 11, 2002

Related U.S. Application Data

(60) Provisional application No. 60/238,856, filed on Oct. 6, 2000.

(51) Int. Cl.[7] ........................... C07C 50/12; C07C 50/04
(52) U.S. Cl. ...................... 552/296; 552/267; 552/299; 552/301; 552/303; 552/307; 552/308
(58) Field of Search ............................... 552/296, 297, 552/299, 301, 303, 307, 308

(56) References Cited

U.S. PATENT DOCUMENTS

| 5,393,909 A | * | 2/1995 | Khokhar et al. | 556/137 |
| 5,539,100 A | | 7/1996 | Wasielewski et al. | 540/145 |

FOREIGN PATENT DOCUMENTS

| WO | WO 98/39010 | 9/1998 | .......... A61K/31/54 |

OTHER PUBLICATIONS

Lipcznska–Kochany et al. Charge–transfer complexation with a new class of electron acceptors made of a tryptycene-quinone unit. Chemistry Letters (1982), (7), pp 1075–8 (abstract).*
P. Bartlett et al., Triptycene (9,10–o–Benzenoanthracene), J. Am. Chem. Soc. 64:2649–53, 1942.
P. Bedworth et al., The Synthesis of a symmetrically substituted α–octa(isopentoxy)anthralocyanine, J. Chem. Soc. Chem. Commum. 1353–54, 1997.
A. Begleiter et al., Characterization of L5178Y murine lymphoblasts resistant to quinone antitumor agents, Cancer Res. 48:1727–35, 1988.
A. Brunmark et al., Redox and addition chemistry of quinoid compounds and its biological implications, Free Radical Biol. & Med. 7:435–477, 1989.
Criswell et al., Studies related to the conversion of 9,10–anthraquinonens to anthracenes, J. Org. Chem. 39(6):770–774, 1974.
J. Daub et al., Chirale elektronentransfer–aktive chinone mit triptycenteilstrukturen: Synthesekonzeption und eigenschaften, Chem. Ber. 121:2187–2194, 1988.
A. Etienne, Dihydroxy–1.4 anthracene et derives alcoyles correspondants. Leur photooxydation et leur photodimerisation, Séance Du 1233–1235, 1955.

R. Ganapathi et al., Modulation of doxorubicin–induced chromosomal damage by calmodulin inhibitors and its relationship to cytotoxicity in progessively doxorubicin–resistant tumor cells, Biochem. Pharmacology 40(7):1657–1662, 1990.
S. Ham et al., Studies on menadione as an inhibitor of the cdc25 phosphatase, Bioorg. Chem. 25:33–36, 1997.
D. Hamon et al., Reductive elimination of bromine from 2,3–disubstituted 1,4–dibromo–2–butenes by iodide ion: A convenient route to 2,3–bis[iodomethyl]–1,3–butadiene and related compounds, J. Chem. Soco Chem. Comm. 873–874, Nov. 1981.
D. Hua, Syntheses of substituted 9,10–dihydro–9,10–[1,2] benzenoanthracene–1.4.5.8–tetraones. Unusual reactives with amines, Abstract of poster presented at ACS 36th Midwest Regional Meeting, Lincoln, Nebraska, Oct. 10–13, 2001.
D. Hua et al., Syntheses and bioactivities of substituted 9,10–dihydro–9,10–[1,2]benzenoanthracene–1,4,5,8–tetraones. Unusual reactivities with amines, J. Org. Chem. 67:2907–2912, 2002.
D. Hua et al., A one–pot condensation of pyrones and enals. Synthesis of 1H,7H–5a,6,8,9–tetrahydro–1–oxopyrano[4, 3–b][1]benzopyrans, J. Org. Chem. 62(20):6888–6896, 1997.
S. Hunig et al., 1,4,5,8–tetraoxo–1,4,5,8–tetrahydrothiantherene: synthesis, structure, and spectroelectrochemical properties, Chem. Ber. 126:465–471, 1992.
H. Iwamura et al., 5,8–dihydroxy–9,10–dihydro–9,10–[1,2] benzenoanthracene–1,4–dione. An Intramolecular triptycene quinhydrone, J. Chem. Soc. Chem. Comm. 16:720–721, 1978.
T. Jozefiak et al., Mixed–valence, conjugated semiquinones, J. Am. Chem. Soc. 111(11):4105–4106, 1989.
A. Kenani et al., Metal–complexing, DNA–binding and DNA–cleaving properties of a synthetic molecule AMBI-GLU, a simplified model for the study of bleomycin, Eur. J. Med. Chem. 24:371–377, 1989.
N. Krishnamachary et al., The MRP gene associated with non–P–glycoprotein multidrug resistance encodes a 190–kDa membrane bound glycoprotein, Cancer Res 53:3658–3661, 1993.
A. Lin et al., Potential bioreductive alkylating agents. 1. Benzoquinone derivatives, J. Med. Chem. 15(12):1247–1252, 1972.

(List continued on next page.)

Primary Examiner—Johann Richter
Assistant Examiner—Sikarl A. Witherspoon
(74) Attorney, Agent, or Firm—Greenlee, Winner and Sullivan, P.C.

(57) ABSTRACT

This invention provides analogs of triptycene which are useful as anticancer drugs, as well as for other uses. The potency of these compounds is in a similar magnitude as daunomycin, a currently used anticancer drug. Each compound of the invention produces one or more desired effects (blocking nucleoside transport, inhibiting nucleic acid or protein syntheses, decreasing the proliferation and viability of cancer cells, inducing DNA fragmentation or retaining their effectiveness against multidrug-resistant tumor cells).

40 Claims, 23 Drawing Sheets

OTHER PUBLICATIONS

A. Lin et al., Potential bioreductive alkylating agents. 2. Antitumor effect and biochemical studies of naphthoquinone derivatives, J. Med. Chem. 16(11):1268–1271, 1973.

A. Lin et al., Potential bioreductive alkylating agents. 3. Synthesis and antineoplastic activity of acetoxymethyl and corresponding ethyl carbamate derivatives of benzoquinones, J. Med. Chem. 17(5):558–561, 1974.

A. Lin et al., Potential bioreductive alkylating agents. 5. Antineoplastic activity of quinoline–5,8–diones, naphthazarins, and naphthoquinones, J. Med. Chem. 18(9):917–921, 1975.

Y–H. Ling et al., Apoptosis induced by anthracycline antibiotics in P388 parent and multidrug–resistant cells, Cancer Res. 53:1845–1852, 1993.

E. Lipczynska–Kochany et al., Charge–transfer complexation with a new class of electron acceptors made of tryptycenequinone unit, Chemistry Letters 7:1075–1078, 1982.

L. Liu, DNA topoisomerase poisons as antitumor drugs, Ann. Rev. Biochem. 58:351–375, 1989.

T. McGrath et al., Adriamycin resistance in HL60 cells in the absence of detectable P–glygoprotein, Biochem. Biophys. Res. Comm. 145(3):1171–1176, 1987.

T. McGrath et al., Mechanisms of multidrug resistance in HL60 cells. Analysis of resistance associated membrane proteins and levels of *mdr* gene expression, Biochem. Pharmacol. 38(20):3611–3619, 1989.

W. Marsh et al., Relation and characterization of Adriamycin–resistant HL–60 cells which are not defective in the initial intracellular accumulation of drug, Cancer Res. 46:4053–4057, 1986.

W. Marsh et al., Adriamycin resistance in HL60 cells and accompanying modification of a surface membrane protein contained in drug–sensitive cells, Cancer Res. 47:5080–5086, 1987.

D. Marquardt et al., Mechanisms of multidrug resistance in HL60 cells: Detection of resistance–associated proteins with antibodies against synthetic peptides that correspond to the deduced sequence of P–glycoprotein, Cancer Res. 50:1426–1430, 1990.

D. Marquardt et al., Involvement of vacuolar $H^+$–adenosine triphosphatase activity in multidrug resistance in HL60 cells, J. Natl. Cancer Inst. 83(15):1098–1102, 1991.

E. Mimnaugh et al., Adriamycin–enhanced membrane lipid peroxidation in isolated rat nuclei, Cancer Res. 45:3296–3304, 1985.

H. Moore, Bioactivation as a model for drug design bioreductive alkylation, Science 197:527–532, 1977.

T. Monks et al., Contemporary issues in toxicology. Quinone chemistry and toxicity, Toxicol. Appl. Pharmacol. 112:2–16, 1992.

C. Myers et al., Anthracyclines. Chapter 14, In: *Cancer Chemotherapy: Principles and Practice*, B. Chabner et al. (eds), Lippincott, pp. 356–381, 1990.

S. Newell et al., Tricyclic pyrone analogs: A. new class of microtubule–disrupting anticancer drugs effective against murine leukemia cells in vitro, Int. J. Oncol. 12(2):433–442, 1998.

S. Norvez, Liquid crystalline triptycene derivatives, J. Org. Chem. 58:2414–2418, 1993.

P. O'Brien, Molecular mechanisms of quinone cytotoxicity, Chem–Biol. Interact. 80:1–41, 1991.

H. Patney, A general and simple route to the synthesis of triptycenes, Synthesis 694–696, Sep. 1991.

E. Perchellet et al., Tricyclic pyrone analogs: A new synthetic class of bifunctional anticancer drugs that inhibit nucleoside transport, microtubule assembly, the viability of leukemic cells in vitro, and the growth of solid tumors in vivo, Anti–cancer Drugs 10(5):489–504, 1999.

E. Perchellet et al., Antitumor activity of tricyclic pyrone analogs, a new synthetic class of microtubule de–stabilizing agents, in the murine EMT–6 mammary tumor cell line in vitro, Anti–Cancer Drugs 6(9):565–576, 1998.

J.–P. Perchellet et al., Triptycene analogs: A novel synthetic class of bifunctional anticancer drugs effective in the nanomolar range in vitro, Introduction to Poster Presented at Am. Assoc. for Cancer Research $91^{st}$ Annual Meeting, San Francisco, CA, Apr. 1–5, 2000.

J.–P. Perchellet et al., Triptycene analogs: A novel synthetic class of bifunctional anticancer drugs effective in the nanomolar range in vitro, Abstract of Poster Presented at Am. Assoc. for Cancer Research $91^{st}$ Annual Meeting, San Francisco, CA, Apr. 1–5, 2000.

J.–P. Perchellet et al., Triptycene analogs: A novel synthetic class of bifunctional anticancer drugs effective in the nanomolar range in vitro, Proceedings of the American Association for Cancer Research 41:602, Mar. 2000.

J.–P. Perchellet et al., Antitumor activity of novel tricyclic pyrone analogs in murine leukemia cells in vitro, Anticancer Research 17:2427–2434, Apr. 1997.

X.–B. Qiu et al., Anticancer quinones induce pRb–preventable G2/M cell cycle arrest and apoptosis, Free Radical Biol. & Med. 24(5):848–854, 1998.

H. Quast et al., ESR–spektroskopischer nachweis intramolekularer wechselwirkungen in radikalkationen von poly($\alpha$–methoxy)triptycenen, Chem. Ber. 119:1016–1038, 1986.

H. Quast et al., Intramolekulare wechselwirkungen in radikalkationen von diund tetra($\alpha$–methoxy)–9,10–dihydro–9,10–ethanoanthracenen, Chem. Ber. 119:2414–2429, 1986.

C. Ramachandran et al., Bcl–2 and mdr–1 gene expression during doxorubicin–induced apoptosis in murine leukemic P388 and P388/R84 cells, Anticancer Research 17:3369–3376, 1997.

L. Rossi et al., Quinone toxicity in hepatocytes without oxidative stress, Arch. Biochem. Biophys. 251:25–35, 1986.

G. Russell et al., Radical anions of triptycene bis– and tris(quinones), J. Am. Chem. Soc. 103(6):1560–1561, 1981.

V. Skvarchenko et al., Advances in the chemistry of triptycene, Russ. Chem. Rev. 43(11):951–966, 1974.

B. Wang et al., A synthetic triptycene bisquinone, which blocks nucleoside transport and induces DNA fragmentation, retains its cytotoxic efficacy in daunorubicin–resistant HL–60 cell lines, Int. J. Ocnology 19:1169–1178, 2001.

B. Wang et al., Antitumor triptycene bisquinones: A novel synthetic class of dual inhibitors of DNA topoisomerase I and II activities, Anti–Cancer Drugs 14:503–514, 2003.

Y. Wang. et al., Induction of poly(ADP–ribose) polymerase–1 cleavage by antitumor triptycene biquinones in wild–type and daunorubicin–resistant HL–60 cell lines, Cancer Letters 188:73–83, 2002.

Scheib, S., et al. In search of Molecular Rectifiers. The donor–sigma–acceptor system derived from Triptycenequinone and tetrathiafulvalene. J. Org. Chem. Jan. 1998, vol. 63, No. 4, pp. 1198–1204.

Perchellet, E.M. et al. Triptycenes: A Novel Synthetic Class of Bifunctional Anticancer Drugs that Inhibit Nucleoside Transport, Induce DNA Cleavage and Decrease the Viability of Leukemic Cells in the Nanomolar Range In Vitro. Anti-Cancer Drugs, 1999, vol. 10, No. 8, pp. 749–766.

* cited by examiner

TRIPTYCENE ANALOGS

CROSS-REFERENCE TO RELATED APPLICATIONS

This application claims priority to U.S. provisional application Ser. No. 60/238,856, filed on Oct. 6, 2000, which is hereby incorporated by reference to the extent not inconsistent with the disclosure herewith.

STATEMENT REGARDING FEDERALLY SPONSORED RESEARCH OR DEVELOPMENT

This invention was made with Government support under Grant No. NAGW-1197 awarded by NASA and Grant No. 86842 awarded by the National Institute of Health. The Government has certain rights in the invention.

BACKGROUND OF THE INVENTION

As precursors of reactive quinone methides, many natural and synthetic quinones function as bioreductive alkylating agents and have antitumor activity. (See for example, Thomson R H, Naturally occuring quinones III: recent advances. New York: Chapman and Hall 1987; Moore H W, Science 1977, 197: 527–32; Lin A J, et al, J Med Chem 1972, 15: 1247–52; Lin A J, et al, J Med Chem 1973, 16: 1268–71; Lin A J, et al, J Med Chem 1974, 17: 558–61; Lin A J, et al, J Med Chem 1975, 18: 917–21). The cytotoxicity of quinones may be due to two competing mechanisms: soft electrophilic arylation and redox cycling oxidation. (See for example, Brunmark A, Cadenas E, Free Radical Biol Med 1989, 7:435–77; O'Brien P J, Chem-Biol Interact 1991, 80: 1–41; Monks T J, et al, Toxicol Appl Pharmacol 1992, 112: 2–16). While complete two-electron reduction of the quinone ring by DT diaphorase produces a stable hydroquinone, partial one-electron reduction of the quinone ring by NADPH-oxidizing enzymes yields an unstable semiquinone free radical (FR) that can spontaneously autoxidize at the expense of molecular $O_2$ to generate a cascade of reactive $O_2$ species (ROS) and FRs, which can induce DNA damage, lipid peroxidation and cytotoxicity. However, most quinone antitumor agents used clinically, such as anthracycline antibiotics, mitomycin C and benzoquinone derivatives, have a complex chemical structure with a number of active functional groups and the exact contribution of the quinone group to their antitumor activity remains uncertain. (See for example, Myers C E, Chabner B A, Anthracyclines. In: Chabner B A, Collins J M, eds. Cancer chemotherapy: principles and practice. Philadelphia: Lippincott 1990: 356–81; Rossi L, et al, Arch Biochem Biophys 1986, 251: 25–35; Begleiter A, et al, Cancer Res 1988, 48: 1727–35; Qiu X B, et al, Free Radical Biol Med 1998, 24: 848–54). The anthracycline quinone antibiotics adriamycin (ADR) and daunomycin (DAU) covalently bind to and intercalate into DNA, inhibit DNA replication and RNA transcription, are DNA topoisomerase (Topo) II poisons, produce oxidative stress and damage biomembranes, induce DNA breakage and chromosomal aberrations, trigger apoptosis and have a wide spectrum of anticancer activity. (See for example, Cadenas E, Free Radical Biol Med 1998, 24: 848–54; Liu L F, Annu Rev Biochem 1989, 58: 351–75; Mimnaugh E G, et al, Cancer Res 1985, 45: 3296–304; Ganapathi R, et al, Biochem Pharmacol 1990, 40: 1657–62; Ling Y-H, et al, Cancer Res 1993, 53: 1845–52; Ramachandran C, et al, Anticancer Res 1997, 17: 3369–76). However, the clinical effectiveness of DOX and DAU is severely limited by their cumulative cardiotoxicity and ability to induce multi-drug resistance, so it is important to develop drugs with improved bioactivity.

SUMMARY OF THE INVENTION

This invention provides analogs of triptycene which are useful as anticancer drugs, as well as for other uses. The potency of these compounds is in a similar magnitude as daunomycin, a currently used anticancer drug. Each compound of the invention produces one or more desired effects (blocking nucleoside transport, inhibiting nucleic acid or protein syntheses, decreasing the proliferation and viability of cancer cells, inducing DNA fragmentation or retaining their effectiveness against multidrug-resistant tumor cells).

More specifically, the invention provides triptycene analogs having the following formula:

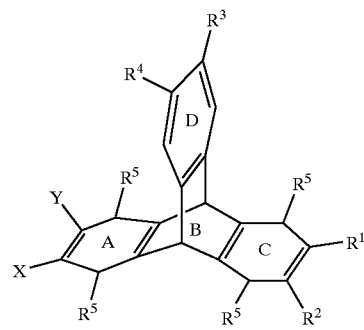

wherein X is selected from the group consisting of: H, R, SR and $NR_2$;

Y is selected from the group consisting of: halogen (preferably Cl, Br, I), R, $NR_2$, SR and H;

R and $R^{1-2}$ are independently selected from the group consisting of: H, halogen, OR, and hydrocarbyl (preferably lower alkyl, allyl, phenyl, aryl, substituted alkyl, substituted allyl, substituted phenyl, $-CH_2-(CH_2)_nCO_2H$, $-CH_2-(CH_2)_nCH(NH_2)CO_2H$, carboxylic acid, substituted carboxylic acid, amine, substituted amine, NHR, $NR_2$, amino acid, $RCO_2(CH_2)_nNH$, where one or both of the hydrogen atoms on $CH_2$ can be substituted with alkyl, allyl, phenyl, aryl, substituted allyl, substituted phenyl, substituted carboxylic acid, amine, or substituted amine, and where n is an integer from 0 to 8); $R^{3-4}$, independently of one another, are selected from the group consisting of: H, halogen (preferably bromine), OR, R, SR and $NR_2$; $R^5$, independently of other $R^5$s, is selected from the group consisting of: $=O$, $=N-OH$, and $=CHR$; and reduced forms thereof; wherein in reduced forms, either ring A or ring C or both is replaced with

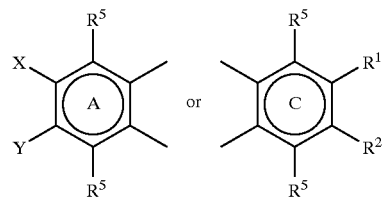

and wherein in reduced forms, each $R^5$ is independently H, C1–C8 alkyl or $-OR$;

and pharmaceutically acceptable salts of the foregoing, as well as optical isomers thereof.

The numbering scheme used herein is shown in the example structure below:

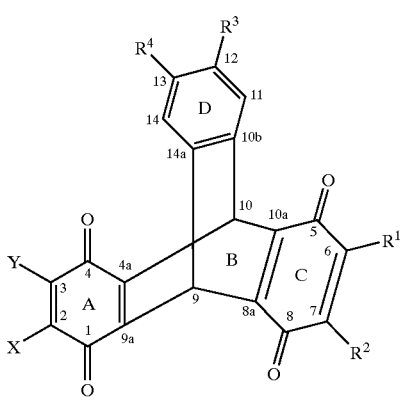

Other compounds of the invention include those with formula:

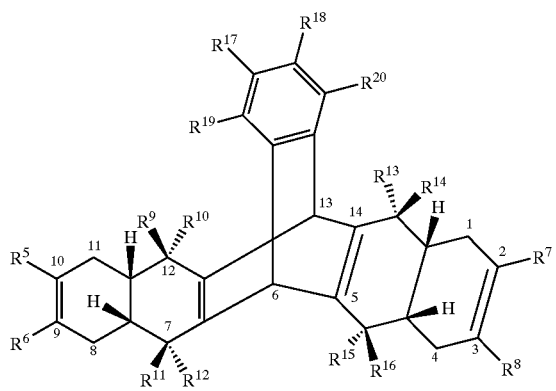

wherein
$R^5$ is selected from the group consisting of: R, halogen, $NR_2$, SR and H; $R^6$ is selected from the group consisting of: H, R, SR and $NR_2$; $R^7$ and $R^8$ are independently selected from the group consisting of: H, halogen, OR and hydrocarbyl; $R^{17}$ and $R^{18}$ are independently selected from the group consisting of: H, halogen, (preferably bromine), R, SR and $NR_2$; $R^{19}$ and $R^{20}$ are, independently of one another, H, R, or OR; ($R^9$ and $R^{10}$) and ($R^{11}$ and $R^{12}$) and ($R^{13}$ and $R^{14}$) and ($R^{15}$ and $R^{16}$) are together =O or are independently H or —OR; R is selected from the group consisting of H, halogen, OR and hydrocarbyl; reduced forms thereof and pharmaceutically acceptable salts of the foregoing, as well as optical isomers thereof.

Other compounds of the invention include those with formula:

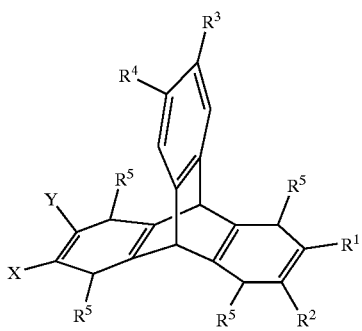

wherein X is —$NW(CW_2)_nZ$, where the Ws are independently selected from the group consisting of: H, C1–C8 alkyl, and C1–C8 alkenyl and Z is selected from the group consisting of: R, COR, COOR, $CONR_2$, OOCR and NRCOR;

Y is selected from the group consisting of: halogen, C1–C8 alkyl, C1–C8 alkenyl, OR, $NR_2$, SR, H, COR, OCOR and NRCOR;

R and $R^{1-2}$, are independently selected from the group consisting of: H, OR, and hydrocarbyl;

$R^{3-4}$, independently of one another, are selected from the group consisting of: H, OR, SR, and $NR_2$;

$R^5$, independently of other $R^5$s, is selected from the group consisting of: =O, —H and —OT, where T is H or C1–C8 alkyl or alkenyl; and pharmaceutically acceptable salts of the foregoing, as well as optical isomers thereof.

Other compounds of the invention include those with formula:

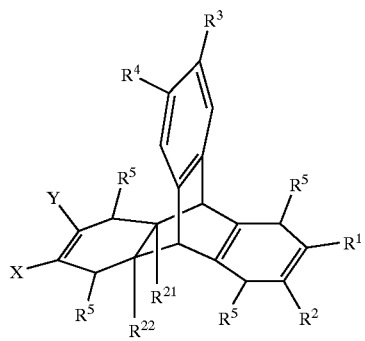

wherein X is selected from the group consisting of: H, R; SR and $NR_2$;

Y is selected from the group consisting of: halogen, $NR_2$, SR, H, and R;

R and $R^{1-2}$, are independently selected from the group consisting of: H, halogen, OR, and hydrocarbyl;

$R^{3-4}$, independently of one another, are selected from the group consisting of: H, halogen (preferably bromine), R, SR, and $NR_2$;

$R^5$, independently of other $R^5$s, is selected from the group consisting of: =O, =NOH, =C HR and reduced forms thereof;

$R^{21}$ and $R^{22}$ are independently selected from the group consisting of: H, R, and OR; and reduced forms thereof and pharmaceutically acceptable salts of the foregoing, as well as optical isomers thereof.

Also provided are compounds of the formula:

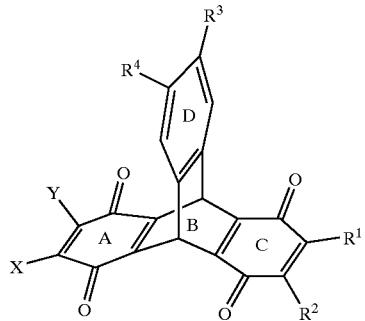

and the reduced forms thereof, wherein in said reduced forms, either ring A or ring C or both is reduced to

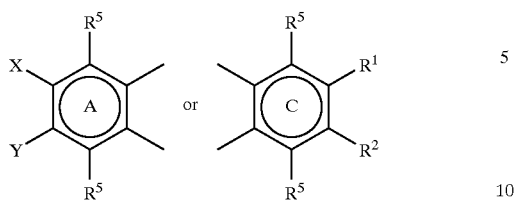

wherein all but one of X, Y, R1 and R2 is independently H, C1–C6 alkyl, C1–C6 alkenyl, OR, SR or NR2 wherein each R is independently H or C1–C6 alkyl and the other R1 or R2 is a solubilzing group; and each R5 is independently H, C1–C6 alkyl or OR. The solubilizing group may be of the formula: $NR(CR_2)_nX$ wherein X is a sugar, R, COR, COOR, $CONR_2$, OOCR and NRCOR; R is independently selected from the group consisting of: H, C1–C8 alkyl and C1–C8 alkenyl; n is an integer from 1 to 8.

Scheme 1 shows some of the compounds of the invention and abbreviations used herein.

Scheme 1

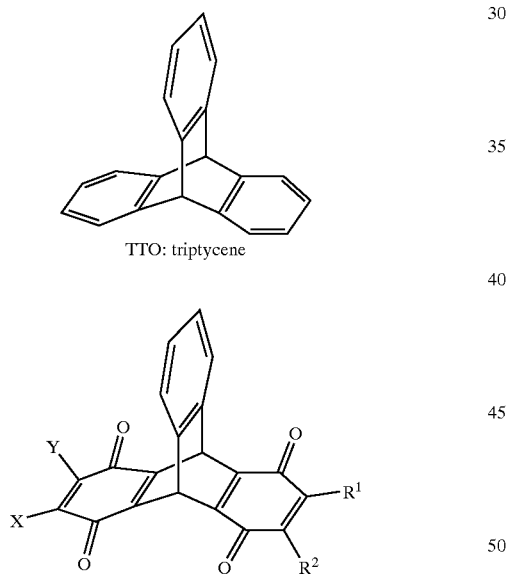

TTO: triptycene

TT1: X = Y = H
TT2: X = PMe, Y = H
TT13: X = OMe, Y = Br
TT14: X = NHMe, Y = Br
TT15: X = MHNe, Y = OH
TT16: X = OMe, Y = Br, $R^2$ = $NMe_2$
TT17: X = $NHCH_2CH_2CO_2H$, Y = Br
TT18: X = $NHCH_2CH_2CO_2Et$, Y = OH
TT19: X = $NH(CH_2)_3CH_2(NH_2)CHCO_2H$, Y = Br
TT20: X = $NH(CH_2)_3CH_2(NH_2)CHCO_2H$, Y = OH
TT21: X = $NHCH_2CH_2CO_2H$, Y = OH
TT24A: X = OMe, Y = Br, $R^2$ = NHMe
TT24B: X = OMe, Y = Br, $R^1$ = NHMe
N analog 1: X = $NH(CH_2)_3CH_2(NH_2)CHCO_2H$, Y = Br
N analog 2: Y = Br, X =

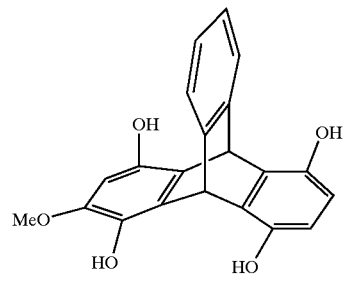

TT3

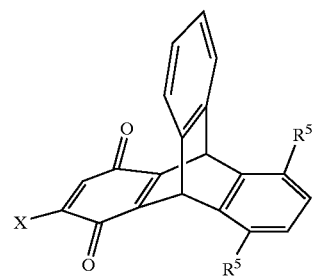

TT5: X = $R^5$ = OMe
TT7: X = $R^5$ = H
TT9: X = OMe, $R^5$ = H

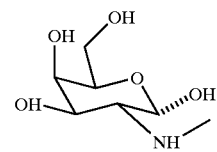

N analog 3: Y = Br, X =

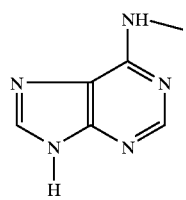

N analog 4: X = OMe, Y = Br, $R^2$ =

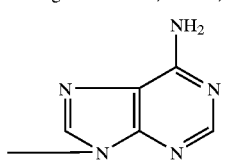

S analog 9: Y = Br, X = $SCH_2CH(CO_2H)NH_2$

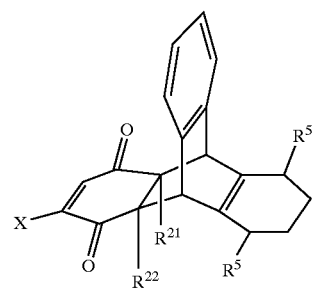

TT6: X = $R^5$ = $R^{21}$ = $R^{22}$ = H
TT8: X = OMe, $R^5$ = $R^{21}$ = $R^{22}$ = H
TT10: X = $CO_2Me$, $R^5$ = OMe, $R^{21}$ = $R^{22}$ = H

-continued

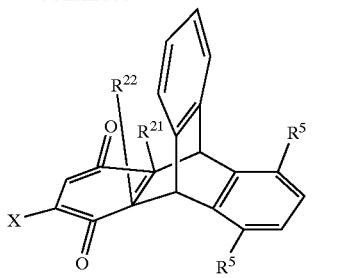

TT11: X = H, R⁵ = OMe, R²² = H, R²¹ = CO₂Me

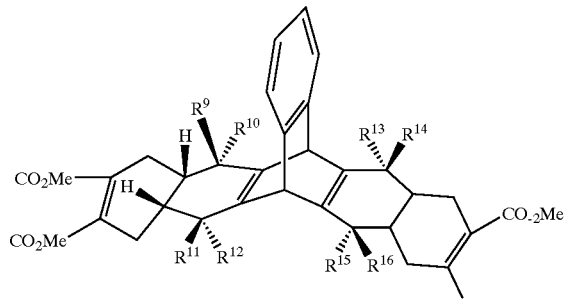

TT4: $R^9 = R^{10} = R^{11} = R^{12} = R^{13} = R^{14} = R^{15} = R^{16} = O$
TT12: $R^9 = R^{11} = R^{13} = R^{15} = H, R^{10} = R^{12} = R^{14} = R^{16} = OH$

Currently, the most preferred compounds include those compounds of the formulas listed above wherein at least one of X, Y, R¹ and R² is selected from the group consisting of: a nitrogen containing group, a water soluble group, and a sulfur containing group, and the following:

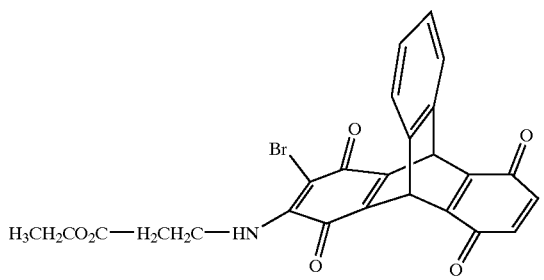

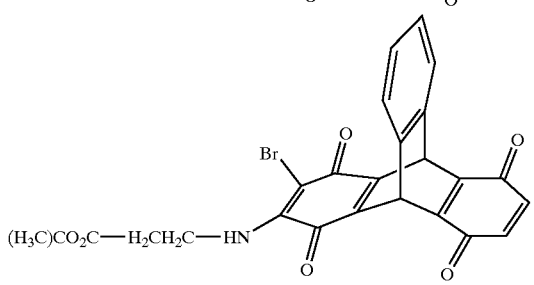

The compounds listed above are useful in treating malaria, cancer, as well as other diseases. Other preferred compounds include those specifically depicted and described in this disclosure.

A class of compounds of this invention includes those compounds listed above as presently preferred. Another class of compounds of this invention include TT2 and TT13. Another class of compounds of this invention include TT1, TT7 and TT9. Another class of compounds of this invention include one or members of the class TT3, TT5, TT6, TT8 and TT10. Another class of compounds of this invention includes homologs of the foregoing compounds. One class of compounds is the compounds TT1–13. Another class of compounds is TT14–20. One class of compounds are those where X is selected from the group consisting of: H, OMe and CO₂Me; where Y is selected from the group consisting of: H, Br, and OMe; where $R^1=R^2=H$; and where positions 1, 4, 5 and 8 are selected from the group OH, OMe, =O, H. Another class of compounds include those where one or more substituents contains one or more N atoms. Another class of compounds includes those where X and Y are not both members of the group containing: H, OMe, Br, CO₂Me, while positions 1, 4, 5, and 8 are substituted with —OH, —OMe or =O, or mixtures of those substituents. Another class of compounds include those which include at least one amine, amino acid or amine sugar substituent.

A preferred class of compounds is those which are water soluble, where one or more substituents, particularly where X,Y,R¹ and/or R² substituents of formula I are replaced with water soluble group or groups that enhance the solubility of the compound and salts thereof.

A preferred class are those compounds of formula I where X is a water soluble group or a group that enhances the water solubility of the compound; and salts thereof. These compounds include those where X is RO₂C (CH₂)ₙNH, where n is an integer from 1 to 8 and R is as defined for I.

Another class of compounds includes those that contain a sulfur containing substituent.

This invention also provides methods for inhibiting cellular transport of nucleosides; inducing DNA fragmentation; inhibiting nucleic acid and/or protein synthesis and decreasing the proliferation and viability of cancer cells (including wild type and multi-drug resistant) or other cells in which the proliferation or viability is desired to be reduced, comprising contacting the cells with an effective amount of a compound of the invention as disclosed herein. This invention provides such compounds in suitable pharmaceutical carriers in dosages effective to provide measurable nucleoside transport blocking, nucleic acid and/or protein synthesis inhibition, DNA cleavage, and/or reduction in tumor cell (including wild type and multi-drug resistant) growth and/or viability. Preferably, the compounds used in the methods of this invention are almost or at least as effective as Daunomycin, a currently used anticancer drug.

Also provided is a method of treating cancer in a host, comprising: administering to said host an effective amount of an active compound of the invention for an effective time. Administration routes include intravenously, parenterally, and other methods known in the art. As used herein, an "effective amount" is an amount which causes a measurable effect on a desired parameter. As used herein, an "effective time" is the time required to cause a measurable or desired effect on a desired parameter.

Also provided is a method for preparation of triptycene analogs, comprising in situ oxidation and [4+2] cycloaddition of substituted benzenes or quinones and optionally substituted anthracenes; and optional oxidation of the resulting compounds. The resulting compounds will be a mixture of methoxy-substituted and carbonyl-substituted triptycene analogs. This mixture can be separated into individual compounds with methods known in the art. The one pot synthesis may be separated into oxidation and cycloaddition steps, if desired. Synthesis of particular groups of compounds of the invention are described in more detail herein.

Also provided is a method to synthesize 1,4-dimethoxyanthracene comprising reduction of quinizarin to give 1,4-anthraquinone; reduction of 1,4-anthraquinone to give 1,4-dihydroxyanthracene; and methylation of 1,4-dihydroxyanthracene to give 1,4-dimethoxyanthracene. These reactions are described in more detail herein. The reduction step (first step; with sodium borohydride) has been reported in: Bedworth, P. V.; Perry, J. W.; Marder, S. R. J. Chem. Soc. Chem. Commun. 1997, 1353–1354 for use in certain synthetic methods and the following two steps (reduction with sodium hydrosulfite and methylation) have been used in certain syntheses, but preparation of 1,4-dimethoxyanthracene (1) has not been reported in one sequence of reaction.

A new synthesis of the compound TT2 is also provided. Either TT3, TT5 or a mixture of both is oxidized to give TT2. A new method to brominate triptycene analogs is also provided. Treatment of a triptycene analog which has a methoxy group on position 2 and a hydrogen on position 3 with N-bromosuccinimide gives an analog with a bromine on position 3. This bromination reaction can be extended to other triptycene analogs. For example, if a methoxy group is on position 6 or 7, bromination will result in a bromine on position 7 or 6, respectively. If the starting compound has methoxy groups on positions 5 and 6, oxidation will give the corresponding analog with carbonyl groups on positions 5 and 6.

Triptycene analogs I bearing functionalities at C12 and C13 ($R^3$ and $R^4$), can be made in an analogous reaction as described below starting with 6,7-disubstituted 1,4-dimethoxyanthracenes (analogs of compound 1). These 6,7-disubstituted 1,4-dimethoxyanthracenes are prepared from the corresponding analogs of 6,7-disubstituted 1,4-dihydroxy-9,10-anthraquinones (by following the method described below).

Also provided are triptycene analogs prepared by the methods described herein.

Compounds containing any combination of substituents or members of the Markush groups specified above are within the scope of the invention. All substituents of the compounds of the invention may be the same, all substituents may be different, or any combination of substituents may be the same or different. Compounds having substituents with a specified function, for example those that impart water solubility to the compound form a special class of compounds of this invention.

The substituents included in the compounds of the invention and used in the methods of the invention may be any substituent not having structures or reactivity which would substantially interfere with the desired activity of the compound, as may readily be determined without undue experimentation by those skilled in the art, for example, by using the assay methods disclosed herein and those methods known to one of ordinary skill in the art.

The reduced forms of all compounds described herein are included in the disclosure. It is understood that when referring to reduced forms of structures herein, any quinone-like ring of the structure may be replaced with a hydroquinone-like ring, as known in the art.

For example, in the following structure,

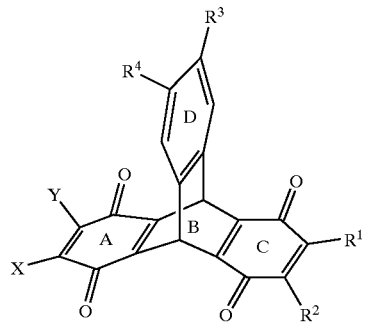

in reduced forms, either ring A or ring C or both is replaced with

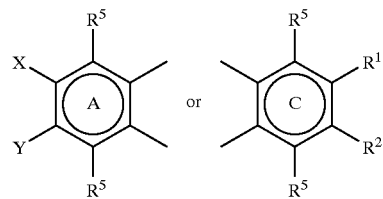

wherein in reduced forms, each $R^5$ is independently a reduced form of =O, for example, OR. In the reduced forms, each $R^5$ may also be H or C1–C8 alkyl, for example, as known in the art.

DETAILED DESCRIPTION OF THE INVENTION

Definitions

Figure 1:
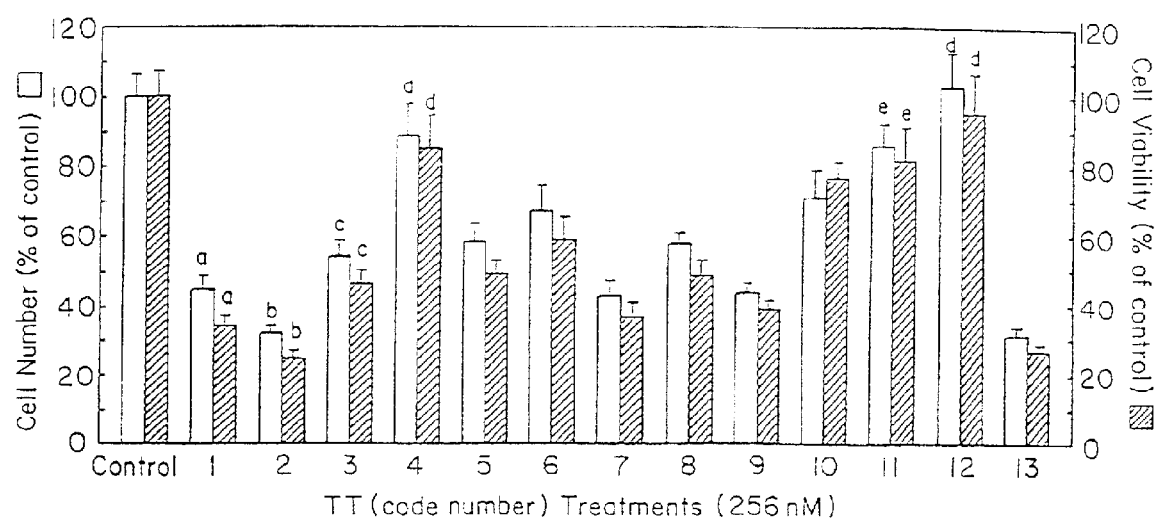
FIG. 1. Comparison of the abilities of novel TTs to inhibit the growth (open) and viability (striped) of L1210 cells after 4 days in vitro. For tumor cell growth and viability, L1210 cells were respectively seeded in triplicate at initial densities of $1 \times 10^4$ and $1.11 \times 10^4$ cells/0.5 ml/well in RPMI 1640 medium containing 7.5% FCS and penicillin (100 IU/ml)-streptomycin (100 μg/ml), and grown for 4 days in the presence or absence (control) of 256 nM concentrations of the indicated compounds in a humidified incubator at 37° C. with 5% $CO_2$ in air. Cell density was monitored using a Coulter counter. Cell growth results are expressed as % of the number of vehicle-treated control cells after 4 days in culture (1,465,110±92,595; 100±6%; open control). The ability of viable cells/0.5 ml to bioreduce 0.1 ml of MTS:PMS (20:1) reagent over a 3-h incubation period at 37° C. was assessed by measuring the absorbamce of the water-soluble formazan products at $A_{490\ nm}$. Cell viability results are expressed as % of the net absorbance of MTS/formazan after bioreduction by vehicle-treated control cells ($A_{490\ nm}$=1.164±0.089; 100±8%; striped control) after 4 days in culture. The blank value ($A_{490\ nm}$=0.202) for cell-free medium supplemented with MTS:PMS reagent has been substracted from the results. Bars: means±SD (n=3). [a]Not different from TT7 and TT9; [b]P<0.025, smaller than TT1, TT7 and TT9 but not different from TT13; [c]P<0.05, greater than TT1, TT7 and TT9 but not different from TT5, TT6 and TT8; [d]not different from control; [e]P<0.05, smaller than control.

The term "hydrocarbyl" is used herein to refer generally to organic groups comprised of carbon chains to which hydrogen and optionally other elements are attached. $CH_2$ or CH groups and C atoms of the carbon chains of the hydrocarbyl may be replaced with one or more heteroatoms (i.e., non-carbon atoms). Suitable heteroatoms include but are not limited to O, S, P and N atoms. The term hydrocarbyl includes, but is not limited to alkyl, alkenyl, alkynyl, ether, polyether, thioether, straight chain or cyclic saccharides, ascorbate, aminoalkyl, hydroxylalkyl, thioalkyl, aryl and heterocyclic aryl groups, optionally substituted tricyclic molecules, amino acid, polyalcohol, glycol, groups which have a mixture of saturated and unsaturated bonds, carbocyclic rings and combinations of such groups. The term also includes straight-chain, branched-chain and cyclic structures or combinations thereof Hydrocarbyl groups are optionally substituted. Hydrocarbyl substitution includes substitution at one or more carbons in the group by moieties containing heteroatoms. Suitable substituents for hydrocarbyl groups include but are not limited to halogens, including chlorine, fluorine, bromine and iodine, OH, SH, $NH_2$, COH, $CO_2H$, $OR_a$, $SR_a$, $NR_aR_b$, $CONR_aR_b$, where $R_a$ and $R_b$ independently are alkyl, unsaturated alkyl or aryl groups.

The term "alkyl" takes its usual meaning in the art and is intended to include straight-chain, branched and cycloalkyl groups. The term includes, but is not limited to, methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, and 1-methyl-1-propylbutyl. Alkyl groups are optionally substituted. Lower alkyl groups are $C_1$–$C_6$ alkyl and include among others methyl, ethyl, n-propyl, and isopropyl groups.

The term "cycloalkyl" refers to alkyl groups having a hydrocarbon ring, particularly to those having rings of 3 to 7 carbon atoms. Cycloalkyl groups include those with alkyl group substitution on the ring. Cycloalkyl groups can include straight-chain and branched-chain portions. Cycloalkyl groups include but are not limited to cyclopropyl, cyclobutyl, cyclopentyl, cyclohexyl, cycloheptyl, cyclooctyl, and cyclononyl. Cycloalkyl groups can optionally be substituted.

Aryl groups may be substituted with one, two or more simple substituents including, but not limited to, lower alkyl, e.g., methyl, ethyl, butyl; halo, e.g., chloro, bromo; nitro; sulfato; sulfonyloxy; carboxy; carbo-lower-alkoxy, e.g., carbomethoxy, carbethoxy; amino; mono- and di-lower-alkylamino, e.g., methylamino, ethylamino, dimethylamino, methylethylamino; amido; hydroxy; lower-alkoxy, e.g., methoxy, ethoxy; and lower-alkanoyloxy, e.g., acetoxy.

The term "unsaturated alkyl" group is used herein generally to include alkyl groups in which one or more carbon-carbon single bonds have been converted to carbon-carbon double or triple bonds. The term includes alkenyl and alkynyl groups in their most general sense. The term is intended to include groups having more than one double or triple bond, or combinations of double and triple bonds. Unsaturated alkyl groups include, without limitation, unsaturated straight-chain, branched or cycloalkyl groups. Unsaturated alkyl groups include without limitation: vinyl, allyl, propenyl, isopropanyl, butenyl, pentenyl, hexenyl, hexadienyl, heptenyl, cyclopropenyl, cyclobutenyl, cyclopentenyl, cyclopentadienyl, cyclohexenyl, cyclohexadienyl, 1-propenyl, 2-butenyl, 2-methyl-2-butenyl, ethynyl, propargyl, 3-methyl-1-pentynyl, and 2-heptynyl. Unsaturated alkyl groups can optionally be substituted.

Substitution of alkyl, cycloalkyl and unsaturated alkyl groups includes substitution at one or more carbons in the group by moieties containing heteroatoms. Suitable substituents for these groups include but are not limited to OH, SH, $NH_2$, COH, $CO_2H$, $OR_c$, $SR_c$, P, PO, $NR_cR_d$, $CONR_cR_d$, and halogens, particularly chlorines and bromines where $R_c$ and $R_d$, independently, are alkyl, unsaturated alkyl or aryl groups. Preferred alkyl and unsaturated alkyl groups are the lower alkyl, alkenyl or alkynyl groups having from 1 to about 3 carbon atoms.

The term "aryl" is used herein generally to refer to aromatic groups which have at least one ring having a conjugated pi electron system and includes without limitation carbocyclic aryl, aralkyl, heterocyclic aryl, biaryl groups and heterocyclic biaryl, all of which can be optionally substituted. Preferred aryl groups have one or two aromatic rings.

"Carbocyclic aryl" refers to aryl groups in which the aromatic ring atoms are all carbons and includes without limitation phenyl, biphenyl and napthalene groups.

"Aralkyl" refers to an alkyl group substituted with an aryl group. Suitable aralkyl groups include among others benzyl, phenethyl and picolyl, and may be optionally substituted. Aralkyl groups include those with heterocyclic and carbocyclic aromatic moieties.

"Heterocyclic aryl groups" refers to groups having at least one heterocyclic aromatic ring with from 1 to 3 heteroatoms in the ring, the remainder being carbon atoms. Suitable heteroatoms include without limitation oxygen, sulfur, and nitrogen. Heterocyclic aryl groups include among others furanyl, thienyl, pyridyl, pyrrolyl, N-alkyl pyrrolo, pyrimidyl, pyrazinyl, imidazolyl, benzofuranyl, quinolinyl, and indolyl, all optionally substituted.

"Heterocyclic biaryl" refers to heterocyclic aryls in which a phenyl group is substituted by a heterocyclic aryl group ortho, meta or para to the point of attachment of the phenyl ring to the decalin or cyclohexane. Heterocyclic biaryl includes among others groups which have a phenyl group substituted with a heterocyclic aromatic ring. The aromatic rings in the heterocyclic biaryl group can be optionally substituted.

"Biaryl" refers to carbocyclic aryl groups in which a phenyl group is substituted by a carbocyclic aryl group ortho, meta or para to the point of attachment of the phenyl ring to the decalin or cyclohexane. Biaryl groups include among others a first phenyl group substituted with a second phenyl ring ortho, meta or para to the point of attachment of the first phenyl ring to the decalin or cyclohexane structure. Para substitution is preferred. The aromatic rings in the biaryl group can be optionally substituted.

Aryl group substitution includes substitutions by non-aryl groups (excluding H) at one or more carbons or where possible at one or more heteroatoms in aromatic rings in the aryl group. Unsubstituted aryl, in contrast, refers to aryl groups in which the aromatic ring carbons are all substituted with H, e.g. unsubstituted phenyl ($-C_6H_5$), or naphthyl ($-C_{10}H_7$). Suitable substituents for aryl groups include among others, alkyl groups, unsaturated alkyl groups, halogens, OH, SH, $NH_2$, COH, $CO_2H$, $OR_e$, $SR_e$, $NR_eR_f$, $CONR_eR_f$, where $R_e$ and $R_f$ independently are alkyl, unsaturated alkyl or aryl groups. Preferred substituents are OH, SH, $OR_e$, and $SR_e$ where $R_e$ is a lower alkyl, i.e., an alkyl group having from 1 to about 3 carbon atoms. Other preferred substituents are halogens, more preferably chlorine or bromine, and lower alkyl and unsaturated lower alkyl groups having from 1 to about 3 carbon atoms. Substituents include bridging groups between aromatic rings in the aryl group, such as $-CO_2-$, $-CO-$, $-O-$, $-S-$, $-P-$, $-NH-$, $-CH=CH-$ and $-(CH_2)_l-$ where l is an integer from 1 to about 5, and particularly $-CH_2-$. Examples of aryl groups having bridging substituents include phenylbenzoate. Substituents also include moieties, such as $-(CH_2)_l-$, $-O-(CH_2)_l-$ or $-OCO-(CH_2)_l-$, where l is an integer from about 2 to 7, as appropriate for the moiety, which bridge two ring atoms in a single aromatic ring as, for example, in a 1, 2, 3, 4-tetrahydronaphthalene group. Alkyl and unsaturated alkyl substituents of aryl groups can in turn optionally be substituted as described supra for substituted alkyl and unsaturated alkyl groups.

The terms "alkoxy group" and "thioalkoxy group" (also known as mercaptide groups, the sulfur analog of alkoxy groups) take their generally accepted meaning. Alkoxy groups include but are not limited to methoxy, ethoxy, n-propoxy, isopropoxy, n-butoxy, sec-butoxy, isobutoxy, tert-butoxy, n-pentyloxy, neopentyloxy, 2-methylbutyloxy, 1-methylbutoxy, 1-ethyl propoxy, 1,1-dimethylpropoxy, n-hexyloxy, 1-methylpentyloxy, 2-methylpentyloxy, 3-methylpentyloxy, 4-methylpentyloxy, 3,3-dimethylbutoxy, 2,2-dimethoxybutoxy, 1-1-dimethylbutoxy, 2-ethylbutoxy, 1-ethylbutoxy, 1,3-dimethylbutoxy, n-pentyloxy, 5-methylhexyloxy, 4-methylhexyloxy, 3-methylhexyloxy, 2-methylhexyloxy, 1-methylhexyloxy, 3-ethylpentyloxy, 2-ethylpentyloxy, 1-ethylpentyloxy, 4,4-dimethylpentyloxy, 3,3-dimethylpentyloxy, 2,2-dimethylpentyloxy, 1,1-dimethylpentyloxy, n-octyloxy, 6-methylheptyloxy, 5-methylheptyloxy, 4-methylheptyloxy, 3-methylheptyloxy, 2-methylheptyloxy, 1-methylheptyloxy, 1-ethylhexyloxy, 1-propylpentyloxy, 3-ethylhexyloxy, 5,5-dimethylhexyloxy, 4,4-dimethylhexyloxy, 2,2-diethylbutoxy, 3,3-diethylbutoxy, 1-methyl-1-propylbutoxy, ethoxymethyl, n-propoxymethyl, isopropoxymethyl, sec-butoxymethyl, isobutoxymethyl, (1-ethyl propoxy)methyl, (2-ethylbutoxy)methyl, (1-ethylbutoxy)methyl, (2-ethylpentyloxy)methyl, (3-ethylpentyloxy)methyl, 2-methoxyethyl, 1-methoxyethyl, 2-ethoxyethyl, 3-methoxypropyl, 2-methoxypropyl, 1-methoxypropyl, 2-ethoxypropyl, 3-(n-propoxy)propyl, 4-methoxybutyl, 2-methoxybutyl, 4-ethoxybutyl, 2-ethoxybutyl, 5-ethoxypentyl, and 6-ethoxyhexyl. Thioalkoxy groups include but are not limited to the sulfur analogs of the alkoxy groups specifically listed supra.

"Optional" or "optionally" means that the subsequently described event or circumstance may or may not occur, and that the description includes instances where said event or circumstance occurs and instances in which it does not. For example, "optionally substituted phenyl" means that the phenyl radical may or may not be substituted and that the description includes both unsubstituted phenyl radicals and phenyl radicals wherein there is substitution.

"Amino acids" as used herein include naturally occurring and commercially available amino acids and optical isomers thereof. Typical natural and commercially available amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, o-, m-, and p-tyrosine, tryptophan, glutamine, asparagine, proline and hydroxyproline. "Amino acid" as used herein includes amino acid residues and amino acid side chains. An "amino acid residue" is an amino acid radical $-NHCH(R)C(O)-$, wherein R is an amino acid side chain, except for the amino acid residues of proline and hydroxyproline which are $-N(CH_2-CH_2-CH_2)CHC(O)-$ and $-N(CH-CHOHCH_2)CHC(O)-$, respectively. An amino acid side chain is a radical found on the $\alpha$-carbon of an $\alpha$-amino acid, where the radical is either hydrogen (side chain of glycine), methyl (side chain of alanine), or is a radical bonded to the $\alpha$-carbon by a methylene ($-CH_2-$), or phenyl group.

"Contacting" reaction components with each other refers to providing a medium and/or reaction chamber in which the reaction components are placed together so that they can react with each other. Preferably, the reaction components are suspended or dissolved in a carrier fluid which is a liquid medium. "Maintaining reaction components in contact" means keeping the components together in such a way that they can react with each other.

"Straight chain or cyclic saccharides" include mono-, di- and poly-, straight chain and cyclic saccharides that are optionally substituted with an amino group which is optionally acetylated. Straight chain saccharides that are useful in this invention include but are not limited to those molecules with a chain of 5 or 6 carbon atoms with one or more $-OH$ groups attached, and either an aldehyde or ketone group. Cyclic saccharides are saccharides that are in a ring form. Disaccharides are compounds wherein two monosaccharide groups are linked. Polysaccharides are compounds wherein more than two monosaccharide groups are linked. Specific examples of saccharides useful in this invention include glucose, ribose and glucosamine, among others.

Substituents which impart water solubility include but are not limited to alcohols; polyalcohols; straight chain or cyclic saccharides; amines and polyamines; sulfate groups; phosphate groups; ascorbate groups; alkyl chains optionally substituted with —OH at any position; glycols, including polyethylene glycols, and polyethers. Substituents which impart water solubility are also referred to as solubilizing groups.

This invention is also directed to pharmaceutically acceptable salts of the various formulas and structures disclosed herein. Acid addition salts are prepared by contacting compounds having appropriate basic groups therein with an acid whose anion is generally considered suitable for human or animal consumption. Pharmacologically acceptable acid addition salts include but are not limited to the hydrochloride, hydrobromide, hydroiodide, sulfate, phosphate, acetate, propionate, lactate, maleate, malate, succinate, and tartrate salts. All of these salts can be prepared by conventional means by reacting, for example, the selected acid with the selected basic compound. Base addition salts are analogously prepared by contacting compounds having appropriate acidic groups therein with a base whose cation is generally considered to be suitable for human or animal consumption. Pharmacologically acceptable base addition salts, include but are not limited to ammonium, amine and amide salts.

Pharmaceutically acceptable esters of compounds of this invention are prepared by conventional methods, for example by reaction with selected acids. Pharmaceutically acceptable esters include but are not limited to carboxylic acid esters RCOO—D (where D is a cationic form of a compound of this invention and where R is H, alkyl or aryl groups).

Effective dosages of the compounds of this invention may be easily determined by those skilled in the art following the teachings hereof and principles known to the art.

The compounds of these inventions may be administered in the form of pharmaceutical preparations including the compounds of these inventions in suitable pharmaceutical carriers to form solutions, lotions, creams, and other dosage forms known to the art. Combinations of such compounds with pharmaceutical carriers are also provided by this invention. Combinations of triptycene analogs described herein along with other compounds which may include other triptycene analogs described herein are also provided by this invention.

This invention is also directed to prodrugs and analogs which on being metabolized will result in any of the effective triptycene analogs of this invention. For example, alkoxy or acetate groups can be metabolized to hydrogens. Labile substituents may be protected employing conventional and pharmaceutically acceptable protecting groups removable on metabolism. Pharmaceutically active compounds may be derivatized by conventional methods to provide for extended metabolic half-life, to enhance solubility in a given carrier, to provide for or facilitate slow-release or timed-release or enhance or affect other drug delivery properties.

Pharmaceutical compositions according to the present invention comprise one or more triptycene compounds, salts or esters of this invention in association with a pharmaceutically acceptable carrier or excipient adapted for use in human or veterinary medicine. Such compositions may be prepared for use in conventional manner in admixture with one or more physiologically acceptable carriers or excipients. The compositions may optionally further contain one or more other therapeutic agents. The compounds, salts or esters of this invention are present in these pharmaceutical compositions in an amount or in a combined amount sufficient to elicit a measurable positive effect on a desired parameter, or a desired physiological effect. The triptycene compounds, salts and esters of this invention may be formulated for oral, buccal, parenteral, topical or rectal administration. In particular, they may be presented in unit dose form. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The pharmaceutical compositions according to the invention may also contain other active ingredients, such as antimicrobial agents, or preservatives.

The invention further provides a process for preparing a pharmaceutical composition which comprises bringing a triptycene analog of the invention into association with a pharmaceutically acceptable excipient or carrier. The carrier or excipient being selected as is known in the art for compatibility with the desired means of administration, for compatibility with the selected compounds and to minimize detrimental effects to the patient.

The magnitude of a prophylactic or therapeutic dose of a particular compound will, of course, vary with the nature of the severity of the condition to be treated, the particular triptycene analog and its route of administration. It will also vary according to the age, weight and response of the individual patient, all as will be readily ascertainable to those skilled in the art.

The compounds of the present invention are preferably formulated prior to administration. The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. The compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

This invention is further directed to therapeutic methods employing the triptycene compounds of this invention and pharmaceutical compositions containing them in the treatment of disorders or physiological conditions involving abnormal cell growth or activity. These methods comprise a step of administering to a patient having the disorder or symptoms thereof a pharmaceutical composition comprising one or a mixture of the compounds, salts or esters of this invention where the compounds, or mixtures of compounds of this invention are present in the composition at a level or a combined level sufficient to effect a positive biological response. The present invention provides triptycene analogs that can be used in place of or in combination with currently known pharmaceuticals active against disorders such as cancer and malaria. Compounds of this invention exhibit improved properties (enhanced activity and/or decreased undesired side-effects) for treatment of such disorders as compared to previously known compounds useful for such treatments.

Table 1 lists the chemical names of the compounds depicted in Scheme 1.

TABLE 1

Nomenclature of various substituted 9,10-Dihydro-9,10-[1',2']
benzenoanthracene-1,4,5,8-tetraones.

TT1: 9,10-Dihydro-9,10-[1',2']benzenoanthracene-1,4,5,8-tetraone.
TT2: 2-Methoxy-9,10-dihydro-9,10-[1',2']benzenoanthracene-1,4,5,8-tetraone.
TT13: 2-Bromo-3-methoxy-9,10-dihydro-9,10-[1',2']benzenoanthracene-1,4,5,8-tetraone.
TT14: 2-Bromo-3-(methylamino)-9,10-dihydro-9,10-[1',2']benzenoanthracene-1,4,5,8-tetraone.
TT3: 1,4-Dihydroxy-2,5,8-trimethoxy-9,10-dihydro-9,10-[1',2']benzenoanthracene.
TT5: 2,5,8-Trimethoxy-9,10-dihydro-9,10-[1',2']benzenoanthracene-1,4-dione.
TT7: 9,10-Dihydro-9,10-[1',2']benzenoanthracene-1,4-dione.
TT9: 2-Methoxy-9,10-dihydro-9,10-[1',2']benzenoanthracene-1,4-dione.
TT6: (4aS*,9aR*)-4a,9,9a,10-Tetrahydro-9,10-[1',2']benzenoanthracene-1,4-dione.
TT8: (4aS*,9aR*)-2-Methoxy-4a,9,9a,10-tetrahydro-9,10-[1',2']benzenoanthracene-1,4-dione.
TT10: (4aS*,9aR*)-5,8-Dimethoxy-2-methoxycarbonyl-4a,9,9a,10-tetrahydro-9,10-[1',2']benzenoanthracene-1,4-dione.
TT11: (4aR*,9aR*)-5,8-Dimethoxy-4a-methoxycarbonyl-9,9a,10-trihydro-9,10-[1',2']benzenoanthracene-1,4-dione.
TT4: (4aS*,7aR*,11aS*,14aR*)-Tetramethyl 1,4,4a,5,6,7,7a,8,11,11a,12,13,14,14a-tetradecahydro-5,7,12,14-tetraoxo-6,13-[1',2']benzenopentacene-2,3,9,10-tetracarboxylate.
TT12: (4aS*,5S*,7R*,12S*,14R*,7aR*,11aS*,14aR*)-Tetramethyl 1,4,4a,5,6,7,7a,8,11,11a,12,13,14,14a-tetradecahydro-5,7,12,14-tetrahydroxy-6,13-[1',2']benzenopentacene-2,3,9,10-tetracarboxylate.
TT15: 2-Hydroxy-3-(methylamino)-9,10-dihydro-9,10-[1',2']benzenoanthracene-1,4,5,8-tetraone.
TT16: 2-Bromo-3-methoxy-6-(dimethylamino)-9,10-dihydro-9,10-[1',2']benzenoanthracene-1,4,5,8-tetraone.
TT17: 2-Bromo-3-[2-(ethoxycarbonyl)ethylamino]-9,10-dihydro-9,10-[1',2']benzenoanthracene-1,4,5,8-tetraone
TT18: 2-hydroxy-3-[2-(ethoxycarbonyl)ethylamino]-9,10-dihydro-9,10-[1',2']benzenoanthracene-1,4,5,8-tetraone
TT20: 2-Hydroxy-3-[(S)-5-(hydroxycarbonyl)-5-aminopentylamino]-9,10-dihydro-9,10-[1',2']benzenoanthracene-1,4,5,8-tetraone

EXAMPLES

The following non-limiting examples are intended to aid in understanding the invention.

In contrast to their inactive parent compound triptycene (code name TT0), several triptycene (TT) analogs were shown to prevent L1210 leukemic cells from synthesizing macromolecules and growing in vitro. TT2 blocks the cellular transport of both purine and pyrimidine nucleosides ($IC_{50}$: 6 $\mu$M) over a 30-sec period in vitro, in contrast to the quinone antitumor drug daunomycin. The concentration-dependent induction of DNA cleavage at 24 h and internucleosomal DNA fragmentation at 48–72 h by TT2 peaks at 4–10 $\mu$M but disappears at 25 $\mu$M. TT2 induction of DNA cleavage is inhibited by actinomycin D, cycloheximide and the caspase inhibitor 2-VAD-fmk, suggesting that TT2 activates endonucleases and triggers apoptosis.

The antitumor activity of TT2 has been compared to that of daunomycin (DAU), a clinically valuable anthracycline antibiotic which is structurally different from TT2 but also contains a quinone moiety. TT2 inhibits the proliferation ($IC_{50}$: 300 nM at day 2 and 150 nM at day 4) and viability ($IC_{50}$: 250 nM at day 2 and 100 nM at day 4) of L1210 cells to the same maximal degree than DAU, suggesting that the cytostatic and cytotoxic activities of TT2 are a combination of drug concentration and duration of drug exposure. Since TT2 does not increase the mitotic index of L1210 cells at 24 h like vincristine, it is unlikely to be an antimitotic drug that disrupts microtubule dynamics. Like DAU, a 1.5- to 3-h pretreatment with TT2 is sufficient to inhibit the rates of DNA, RNA and protein syntheses determined over 30- to 60-min periods of pulse-labeling in L1210 cells in vitro ($IC_{50}$: 6 $\mu$M). In contrast to DAU, which is inactive, a 15-min pretreatment with TT2 has the advantage of also inhibiting the cellular transport of nucleosides occuring over a 30-sec period in vitro ($IC_{50}$: 6 $\mu$M), suggesting that TT2 prevents the incorporation of $^3$H-thymidine into DNA because it rapidly blocks the uptake of $^3$H-thymidine by the tumor cells. After 24 h, TT2 induces as much DNA cleavage as camptothecin and DAU, two anticancer drugs producing DNA-strand breaks and known to respectively inhibit DNA topoisomerase I and II activities. Interestingly, the abilities of TT2 to block nucleoside transport, inhibit DNA synthesis and induce DNA fragmentation are irreversible upon drug removal, suggesting that this compound may rapidly interact with various molecular targets in cell membranes and nuclei to disrupt the functions of nucleoside transporters and nucleic acids and trigger long-lasting antitumor effects which persist after cessation of drug treatment. Because inhibition of nucleoside transport is highly unusual among DNA-damaging drugs, the use of bifunctional TTs with antileukemic activity in the nM range in vitro provides a considerable advantage in polychemotherapy to potentiate the action of antimetabolites and sensitize multidrug-resistant tumor cells.

Materials and Methods

Cell Culture and Drug Treatments

TT0 was purchased from Aldrich (Milwaukee, Wis.). All solutions of synthetic TTs and tricyclic pyrone H10, vincristine (VCR; a gift from Lilly Researeh Laboratories, Indianapolis, Ind.) and camptothecin (CPT; from Sigma Chemical Co., St Louis, Mo.) were dissolved and diluted in dimethyl sulfoxide (DMSO), whereas daunomycin (DAU) (from Sigma) solutions were prepared in 0.1 M potassium phosphate buffer, pH 7.4, containing 0.9% NaCl. Suspension cultures of murine L1210 lymphocytic leukemia cells (American Type Culture Collection, Rockville, Md.) were maintained in continuous exponential growth by twice-a-week passage in RPMI 1640 medium supplemented with 7.5% fortified bovine calf serum (FCS; HyClone Laboratories, Logan, Utah) and penicillin (100 IU/ml)- streptomycin (100 μg/ml), and incubated in the presence or absence of drugs at 37° C. in a humidified atmosphere containing 5% $CO_2$. Since drugs were supplemented to the culture medium in 1 μl aliquots, the concentration of DMSO in the final incubation volume (0.5 ml) never exceeded 0.2% and did not affect the rates of macromolecule syntheses and growth in L1210 cells. Control cells incubated in the absence of drugs were similarly treated with vehicle only and, in every experiment, all incubates received the same volume of solvent. For drug removal, incubates were spun at 200×g for 10 min, drug-containing supernatants were discarded, and intact cells were washed thrice with 1 ml of the above RPMI 1640 culture medium and resuspended in 0.5 ml of fresh medium for further incubation.

Suspension cultures of WT, drug-sensitive, human HL-60-S promyelocytic leukemia cells, were obtained from American Type Culture Collection (Manassas, Va.), maintained in continuous exponential growth by twice-a-week passage in RPMI 1640 medium supplemented with 8.25% fortified bovine calf serum (FCS; Hyclone Laboratories, Logan, Utah) and penicillin (100 IU/ml)-streptomycin (100 μg/ml), and incubated in the presence or absence of drugs at 37° C. in a humidified atmosphere containing 5% $CO_2$. The MDR HL-60-RV and HL-60-R8 cells were developed in Melvin S. Center's laboratory (Kansas State University) and similarly maintained in RPMI 1640 medium in the absence of drugs (Marsh W, et al, Cancer Res 46: 4053–4057, 1986; McGrath T et al, and Center M S: Biochem Biophys Res Commun 145: 1171–1176, 1987; Marsh W and Center M S: Cancer Res 47: 5080–5086, 1987; McGrath T, et al, Biochem Pharmacol 38: 3611–3619, 1989; Marquardt D, et al, Cancer Res 50: 1426–1430, 1990; Marquardt D and Center M S: J Natl Cancer Inst 83: 1089–1109, 1991; Krishnamachary N and Center M S; Cancer Res 53: 3658–3661, 1993). Every 4 weeks, these HL-60-RV and HL-60-R8 sublines were exposed to 41 nM DAU for 48 h to stabilize their MDR phenotype. This concentration of DAU, which is not cytotoxic to MDR HL-60 sublines, was removed from the culture medium at least 48 h before experimentation. Since drugs were supplemented to the culture medium in 1 μl aliquots, the concentration of vehicle in the final incubation volume (0.5 ml) did not affect basal activity levels in control tumor cells incubated in the absence of drugs. RFs were determined by dividing the $IC_{50}$ of the MDR cells by that of the sensitive WT parent cell line.

Cell Proliferation Assay

For tumor cell growth, L1210 cells were resuspended in fresh FCS-containing RPMI 1640 medium, plated at an initial density of 1×10⁴ cells/0.5 ml, and incubated in 48-well Costar cell culture plates (Costar, Cambridge, Mass.). Except when otherwise specified, cells were grown for 4 days in the presence or absence of drugs and their density was monitored every 24 h using a Coulter counter (Coulter Electronics, Luton Beds, UK).

HL-60-S, HL-60-RV and HL-60-R8 cells were resuspended in fresh FCS-containing RPMI 1640 medium, seeded in triplicate at an initial density of 1.5×10⁴ cells/0.5 ml and incubated at 37° C. in 48-well Costar cell culture plates (Costar, Cambridge, Mass.). Tumor cells were grown for 4 days in the presence or absence (control) of drugs and their density was monitored every 24 h using a Z1 dual threshold Coulter counter (Beckman Coulter, Miami, Fla.).

Cell Viability Assay

L1210, HL-60-S, HL60-RV and HL-60-R8 cells suspended in FCS-containing RPMI 1640 medium were grown in 48-well Costar cell culture plates for up to 4 days in the presence or absence of drugs to evaluate drug cytotoxicity. Decreasing concentrations of cells, such as 1×10⁵ and 1.11×10⁴ cells/0.5 ml/well, were initially plated at time 0 in order to collect control samples with approximately equal cell densities after 2 and 4 days in culture, respectively. The viability of TT-treated cells was assessed from their ability to bioreduce the 3-(4,5-dimethylthiazol-2-yl)-5-(3-carboxymethoxyphenyl)-2-(4-sulfophenyl)-2H-tetrazolium (MTS) reagent (Promega, Madison, Wis.) in the presence of phenazine methosulfate (PMS; Sigma) into a water-soluble formazan product which absorbs at 490 nm. At the appropriate time after drug treatment, cell samples (about 10⁶/0.5 ml/well for controls) were further incubated at 37° C. for 3 h in the dark in the presence of 0.1 ml of MTS:PMS (2:0.1) reagent and their relative cell viability was estimated by recording the Abs. at 490 nm, using a Cambridge model 750 automatic microplate reader (Packard, Downers Grove, Ill.). Blank values for culture medium supplemented with MTS:PMS reagent in the absence of cells were substracted from the results.

Macromolecule Synthesis

For nucleic acid and protein syntheses, L1210 cells were resuspended in fresh FCS-containing RPMI 1640 medium at a density of about 1.1–1.6×10⁶ cells/0.5 ml. To estimate the rate of DNA synthesis, HL-60-S, HL-60-RV and HL-60-R8 cells were resuspended in fresh FCS-containing RPMI 1640 medium at a density of 5×10⁵ cells/0.5 ml. Except when otherwise specified, the cells were incubated at 37° C. for 90 min in the presence or absence of drugs and then pulse-labeled for an additional 30 min with 1 μCi of [methyl-³H] thymidine (50 Ci/mmol; Amersham Corp., Arlington Heights, Ill.) to estimate the rate of DNA synthesis. For RNA and protein syntheses, cells were incubated at 37° C. for 3 h in the presence or absence of drugs and then pulse-labeled for an additional 1 h with 2 μCi of (5,6-³H]uridine (46 Ci/mmol; ICN Biomedicals, Irvine, Calif.) or 2.5 μCi of [4,5-³H]L-leucine(100 Ci/mmol; Moravek Biochemicals, Brea, Calif.), respectively. The incubations were terminated by the addition of 0.5 ml of 10% trichloroacetic acid (TCA). After holding on ice for 15 min, the acid-insoluble material was recovered over Whatman GF/A glass microfibre filters and washed thrice with 2 ml of 5% TCA and twice with 2 ml of 100% EtOH. After drying the filters, the radioactivity bound to the acid-precipitable material was determined by liquid scintillation counting (LSC) in 10 ml of Bio-Safe NA (Researeh Products International Corp., Mount Prospect, Ill.).

Nucleoside Transport

L1210 cells (about 1.5×10⁶ cells/0.5 ml) were preincubated for 15 min at 37° C. in the presence or absence of TTs and then exposed to 1 μCi of ³H-thymidine for only 30 sec to assess the cellular uptake of nucleoside over such very short period of time. HL-60-S, HL-60-RV and HL-60-R8 cells (1.2×10⁶ cells/0.5 ml) were preincubated for 15 min at 37° C. in the presence or absence (control) of drugs and then exposed to 1 μCi of [2,8-³H]adenosine (30 Ci/mmol; American Radiolabeled Chemicals, St. Louis, Mo.) or [methyl-³H]thymidine (50 Ci/mmol; Amersham, Arlington Heights, Ill.) for only 30 s to, respectively, assess the cellular uptake of purine and pyrimidine nucleosides over such very short period of time Reactions were diluted with 2 ml of ice-cold $Ca^{2+}/Mg^{2+}$-free Dulbecco's phosphate buffered saline (PBS) and the unincorporated radiolabel was removed by centrifugation at 200×g for 10 min. After washing thrice with 2 ml of ice-cold PBS, intact cell pellets were harvested by centrifugation and incubated for 30 min in 1 ml of hypotonic lysis buffer (HLB) containing 10 mM Tris-HCl, pH 8.0, 1 mM EDTA and 0.2% Triton X-100. Cell lysates were mixed with 9 ml of Bio-Safe II (Research Products International) and counted to estimate the cellular uptake of $^3$H-thymidine. Drug inhibition was expressed as % of $^3$H-thymidine or $^3$H-adenosine transported into vehicle-treated control cells over similar 30-sec period.

Mitotic Index

L1210 cells (about 1×10$^6$/0.5 ml of FCS-containing RPMI 1640 medium) were incubated in triplicate for 24 h at 37° C. in the presence or absence of TTs or known antimitotic drugs, and collected by centrifugation at 200×g for 10 min to determine their mitotic index. For hypotonic treatment, cells were resuspended in 1 ml of 75 mM KCl for 20 min at 4° C. After fixation in 1 ml of MeOH:acetic acid (3:1), the final cell pellets were collected by centrifugation, resuspended in 75 μl of MeOH:acetic acid (3:1), dispensed onto glass slides, air dried, and stained by spreading 40 μl of 0.1% crystal violet under a coverslip. The % of cells in mitosis was determined microscopically by counting 500 cells/slides. The mitotic index was calculated as the % of mitotic cells in drug-treated cultures divided by the % of mitotic cells in non-treated controls.

DNA Cleavage

Drug-induced DNA cleavage was determined by intact chromatin precipitation, using L1210, HL-60-S, HL-60-RV and HL-60-R8 cells which were prelabeled with 1 μCi of $^3$H-thymidine for 2 h at 37° C., washed with 3×1 ml of ice-cold PBS, collected by centrifugation, and resuspended in fresh FCS-containing RPMI 1640 medium at a density of about 1×10$^6$ cells/0.5 ml for L1210 and 0.5×10$^6$ cells/0.5 ml for HL cells. Except when otherwise specified, such cells containing prelabeled DNA were then exposed for 24 h to TTs and drugs known to induce DNA fragmentation. After centrifugation at 200×g for 10 min to discard the drugs and wash the cells, the intact cell pellets were lysed for 30 min in 0.5 ml of HLB, centrifuged at 12,000×g for 30 min to collect the supernatants, and resuspended in 0.5 ml of HLB. After another similar centrifugation, the radioactivities in the pooled supernatants (detergent-soluble low molecular weight DNA fragments) and the pellet (intact chromatin DNA) were determined by LSC: % DNA fragmentation= [cpm in supernatant/cpm in supernatant+pellet]×100. Before being counted in 6 ml of Bio-Safe NA, the intact pelleted chromatin was incubated for 2 h at 60° C. in the presence of 0.6 ml of NCS tissue solubilizer (Amersham).

Results

Drugs

The TT quinones under study were synthesized in the laboratory by an in-situ oxidation of substituted dihydroxybenzenes followed by [4+2]cycloaddition with 1,4-dimethoxyanthracene and then oxidation. This method of synthesis is reported below. The chemical structures of the TTs tested for their antileukemic activity in vitro are shown in Scheme 1 (serial numbers indicate the order of synthesis).

Inhibition of Tumor Cell Growth and Viability by TTs

L1210

Figure 2:
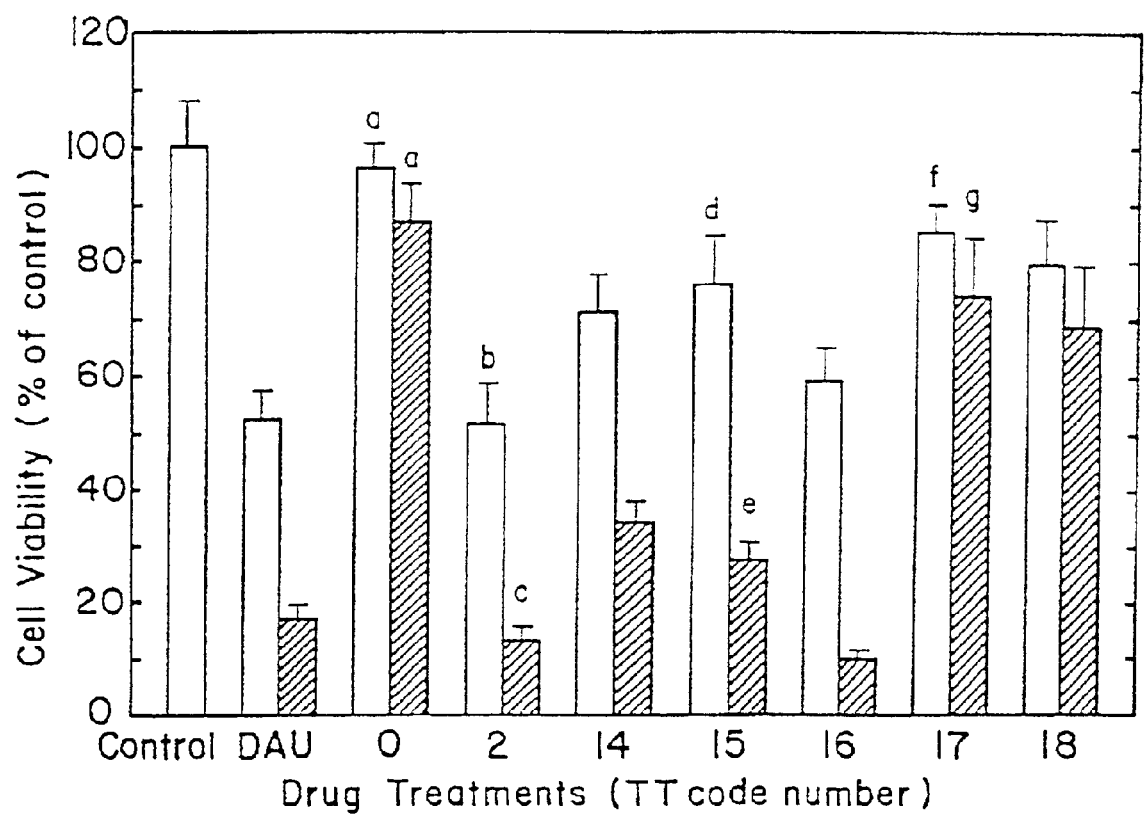
FIG. 2. The same experiment as in FIG. 1 with additional compounds.

When tested at 256 nM over a 4-day period, several TTs inhibit the rate of tumor cell growth in relation with their ability to decrease tumor cell viability (FIG. 1). Although most of these drugs are much more active at higher concentrations, at this lower concentration of 256 nM, TT4 and TT12 are inactive and TT11 and TT10 have only marginal and weak inhibitory effects. In contrast, 256 nM TT3, TT5, TT6 and TT8 have moderate cytostatic (32–45% inhibition) and cytotoxic (41–54% inhibition) activities. Under similar conditions, TT1, TT7 and TT9 are more effective and can reduce the number and viability of L1210 cells at 4 days by 55–57% and 61–66%, respectively. TT2 and its C2-brominated derivative TT13 at 256 nM, can inhibit leukemic cell proliferation and viability by 67–68% and 73–75%, respectively (FIG. 1). FIG. 2 shows the same experiment for additional TT compounds.

Figure 3:
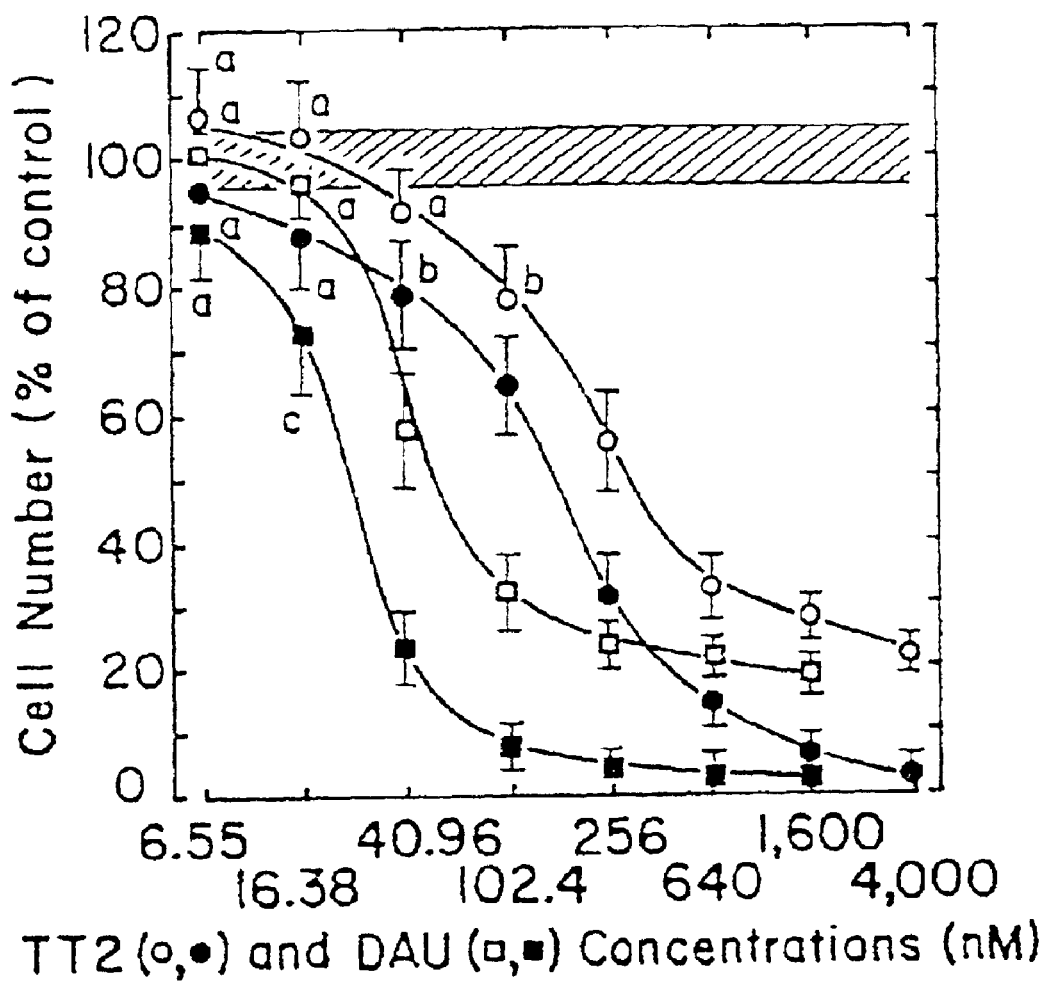
FIG. 3. Comparison of the concentration-dependent inhibitions of L1210 cell growth by the TT analog TT2 (○,●) and DAU (□,■) at days 2 (open symbols) and 4 (closed symbols) in vitro. The protocol of the experiment was identical to that of FIG. 1. The results are expressed as % of the numbers of vehicle-treated control cells (100±4%; striped area) after 2 (213,798±8,316 cells/ml) and 4 days (1,311,274±55,991 cells/ml) in culture. Drug concentrations are plotted on a logarithmic scale. Bars: means±SD (n=3). $^a$Not different from control; $^b$P<0.025 and $^c$P<0.01, smaller than control.
Figure 4:
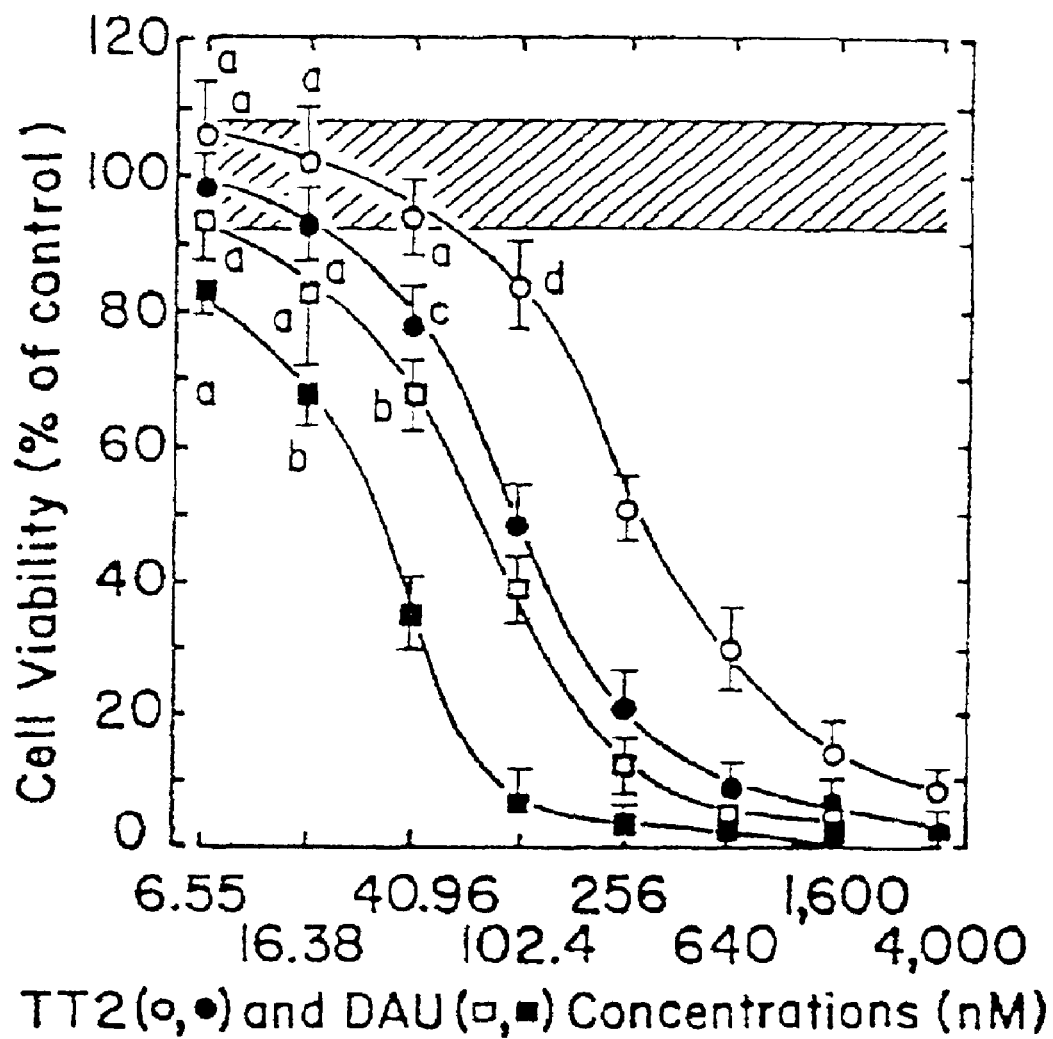
FIG. 4. Comparison of the concentration-dependent inhibitions of L1210 cell viability by the TT analog TT2 (○,●) and DAU (□,■) at days 2 (open symbols) and 4 (closed symbols) in vitro. Cells were seeded in triplicate at initial densities of 100,000 or 11,100 cells/0.5 ml/well and respectively incubated for 2 or 4 days in the presence or absence (control) of the indicated concentrations of drugs, which are plotted on a logarithmic scale. The ability of viable cells/0.5 ml to bioreduce 0.1 ml of MTS:PMS (20:1) reagent over a 3-h incubation period was assessed as described in FIG. 1. Cell viability results are expressed as % of the net absorbance of MTS/formazan after bioreduction by vehicle-treated control cells (100±8%; striped area) at days 2 ($A_{490\ nm}$=1.206±0.093) and 4 ($A_{490\ nm}$=1.096±0.086). Blank values ($A_{490\ nm}$=0.185 and 0.189 at days 2 and 4) for culture medium supplemented with MTS:PMS reagent have been substracted from the results. Bars: means±SD (n=3). $^a$Not different from control; $^b$P<0.005, $^c$P<0.025 and $^d$P<0.05, smaller than control.

DAU is a clinically valuable anthracycline antibiotic, which also contains a quinone moiety. At concentrations ≧640 nM, TT2 inhibits almost totally the proliferation and viability of L1210 cells at day 4 but these maximal cytostatic and cytotoxic activities of TT2 can be mimicked by concentrations of DAU as low as 102 nM and the smallest concentrations of TT2 and DAU that can induce significant antiproliferative and cytotoxic effects after 4 days are 41 and 16 nM, respectively (FIGS. 3 & 4). These relative potencies of TT2 and DAU can easily be compared using the full concentration-response curves of FIGS. 3 and 4, where the striped areas at 100% represent the control levels of L1210 cell growth and viability after 2 and 4 days in culture. The magnitudes of the cytostatic and cytotoxic effects of both TT2 and DAU are clearly related to the combination of their increasing concentration and duration of action. For instance, 16 nM DAU and 41 nM TT2 are ineffective at day 2 but their antiproliferative (FIG. 3) and cytotoxic (FIG. 4) activities become apparent at day 4. Moreover, 41 nM DAU and 256 nM TT2 are moderately cytostatic (42 and 44% inhibition, respectively) and cytotoxic (32 and 49% inhibition, respectively) at day 2 but respectively decrease L1210 cell proliferation by 77 and 68% and L1210 cell viability by 65 and 79% at day 4 (FIGS. 3 & 4). As a result, the antiproliferative activities of DAU and TT2 are respectively characterized by IC$_{50}$ values of 50 and 300 nM at day 2 but 25 and 150 nM at day 4, suggesting that DAU is about 6 times more cytostatic than TT2 in the L1210 tumor system in vitro (FIG. 3). Similarly, the inhibitions of tumor cell viability by DAU and TT2 are respectively characterized by IC$_{50}$ values of 70 and 250 nM at day 2 but 30 and 100 nM at day 4, suggesting that DAU is about 3.5 times more cytotoxic than TT2 in this leukemic system in vitro (FIG. 4).

HL

Figure 5:
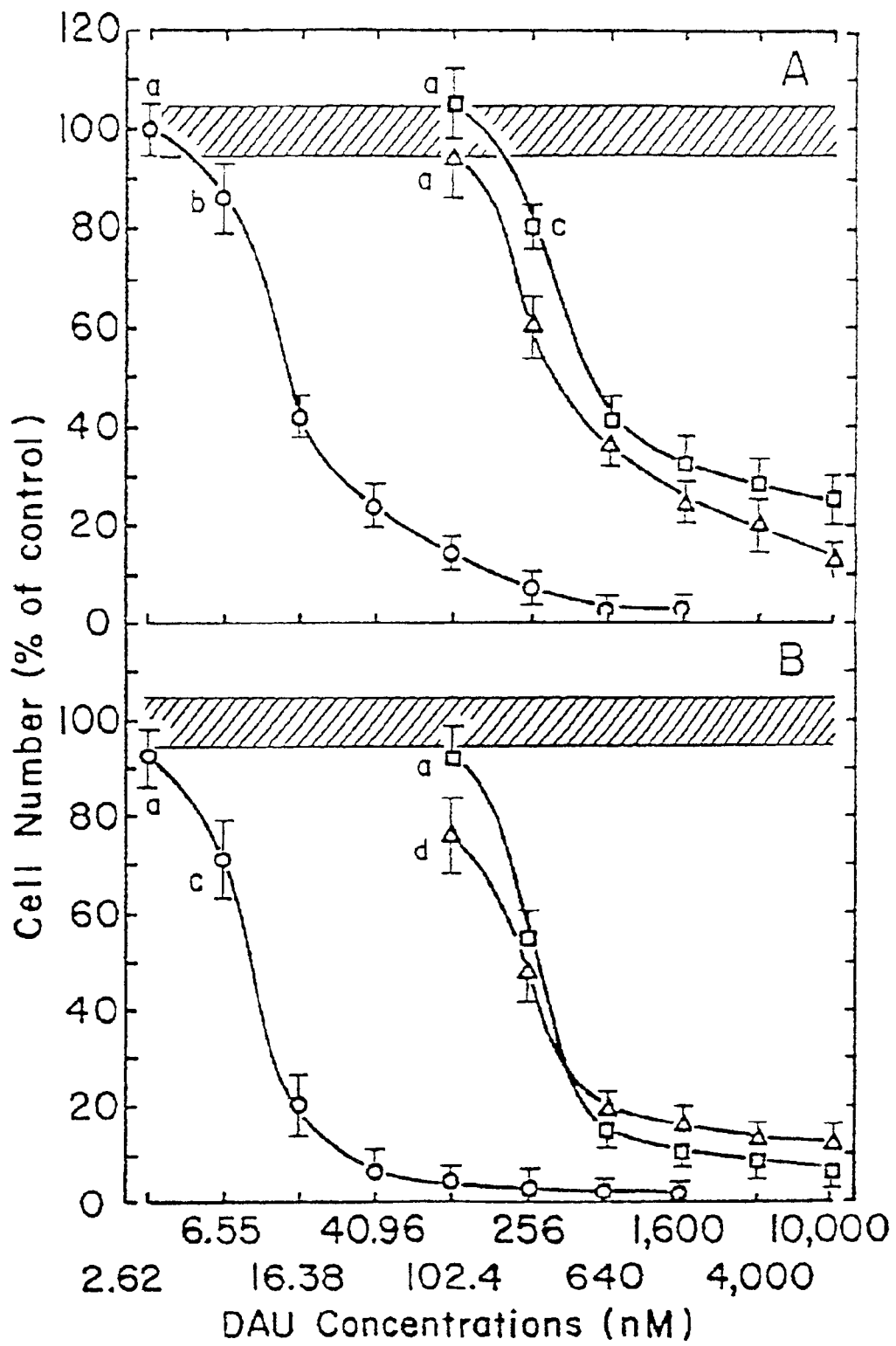
FIG. 5. Comparison of the concentration-dependent inhibitions of HL-60-S (○), HL-60-RV (□) and HL-60-R8 (Δ) cell proliferation by DAU at days 2 (A) and 4 (B) in vitro. Cell growth results are expressed as % of the numbers of vehicle-treated control tumor cells (100±5%, striped areas) after 2 (110,903±5,878 cells/ml) and 4 days (253,462±12,166 cells/ml) in culture. Bars: means±SD (n=3). $^a$Not different from control; $^b$P<0.05, $^c$P<0.01 and $^d$P<0.025, smaller than control.
Figure 6:
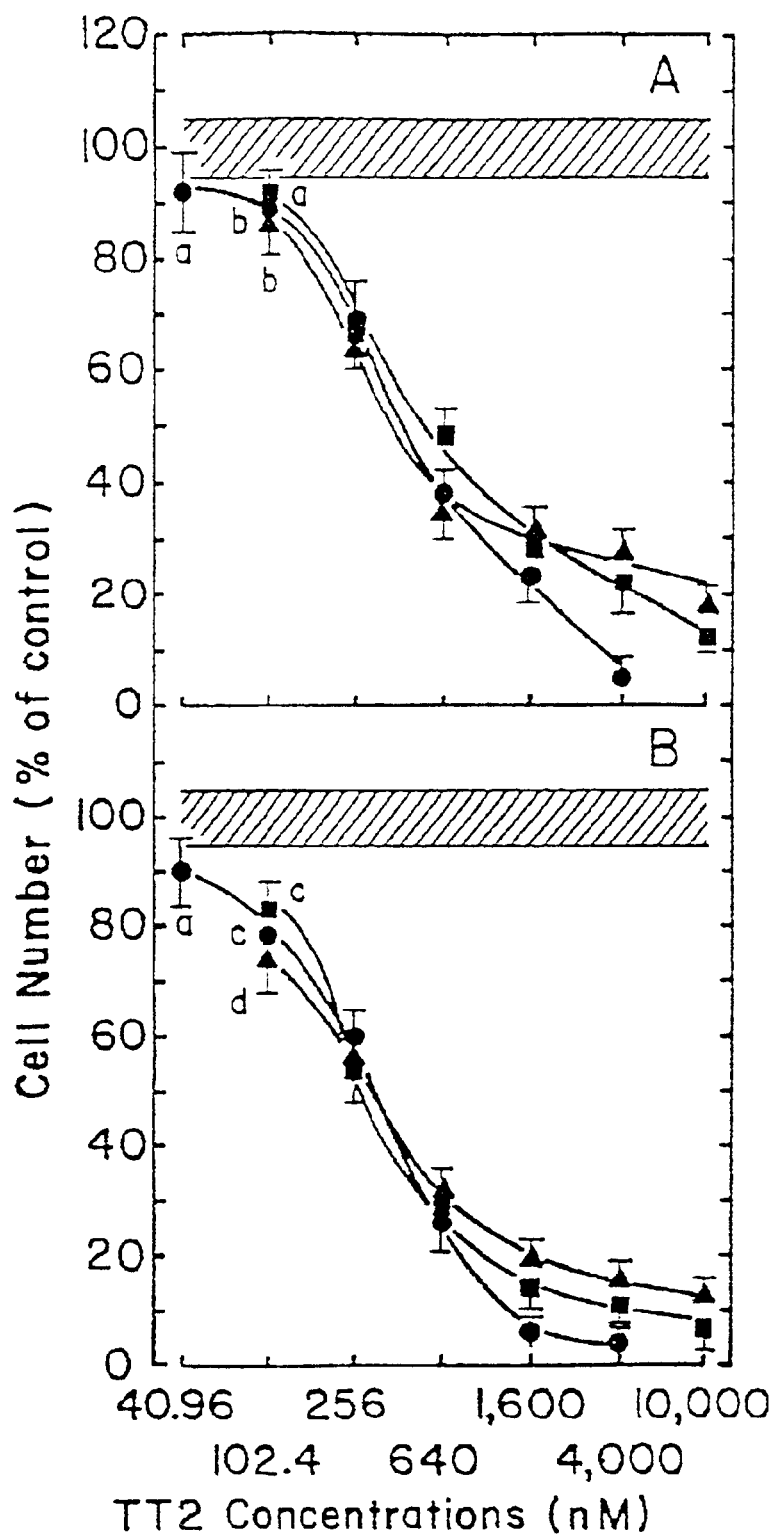
FIG. 6. Comparison of the concentration-dependent inhibitions of HL-60-S (●), HL-60-RV (■) and HL-60-R8 (▲) cell proliferation by TT2 at days 2 (A) and 4 (B) in vitro. The conditions of the experiments and the determination of the results were identical to those of FIG. 5. Bars: means±SD (n=3). $^a$Not different from control; $^b$P<0.05, $^c$P<0.025 and $^d$P<0.005, smaller than control.

The concentration-dependent inhibitions of HL-60-S, HL-60-RV and HL-60-R8 cell proliferation by DAU are respectively characterized by IC$_{50}$ values of 14, 500 and 320 nM at day 2 (FIG. 5A) and 9,275 and 225 nM at day 4 (FIG. 5B). Such RFs of 22.9–35.7 at day 2 and 25.0–30.6 at day 4 demonstrate that DAU is about 30 times less effective as a cytostatic agent in MDR than in WT HL-60 cells (FIG. 5). In contrast, the concentration-dependent inhibitions of HL-60-S, HL-60-RV and HL-60-R8 cell proliferation by TT2 are respectively characterized by similar IC$_{50}$ values of 400, 500 and 350 nM at day 2 (FIG. 6A) and 300, 260 and 290 nM at day 4 (FIG. 6B). These negligible RFs (0.9–1.3 at day 2 and 0.9–1.0 at day 4) suggest that TT2 retains its effectiveness as a cytostatic agent in MDR cells that have become 30 times less sensitive to the antiproliferative action of DAU (FIG. 6).

Figure 7:
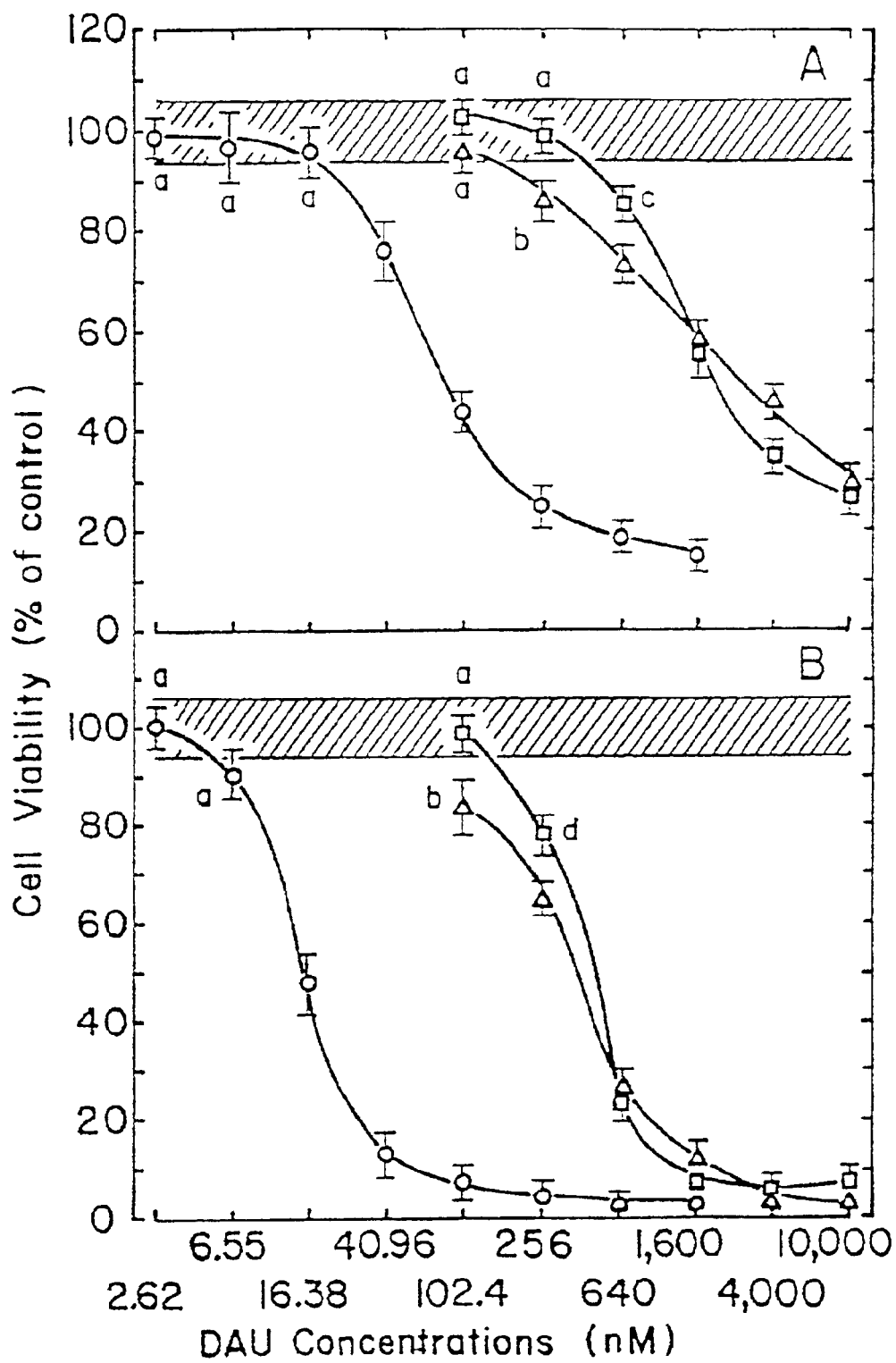
FIG. 7. Comparison of the concentration-dependent inhibitions of HL-60-S (○), HL-60-RV (□) and HL-60-R8 (Δ) cell viability by DAU at days 2 (A) and 4 (B) in vitro. Cell viability results are expressed as % of the net absorbance of MTS/formazan after bioreduction by vehicle-treated control cells (100±6%, striped areas) at days 2 ($A_{490\ nm}$=1.635±0.105) and 4 ($A_{490\ nm}$=1.428±0.086). Blank values ($A_{490\ nm}$=0.412 and 0.436 at days 2 and 4 ) for cell-free culture medium supplemented with MTS: PMS reagent have been substracted from the results. Bars: means±SD (n=3). $^a$Not different from control; $^b$P<0.05, $^c$P<0.025 and $^d$P<0.01, smaller than control.
Figure 8:
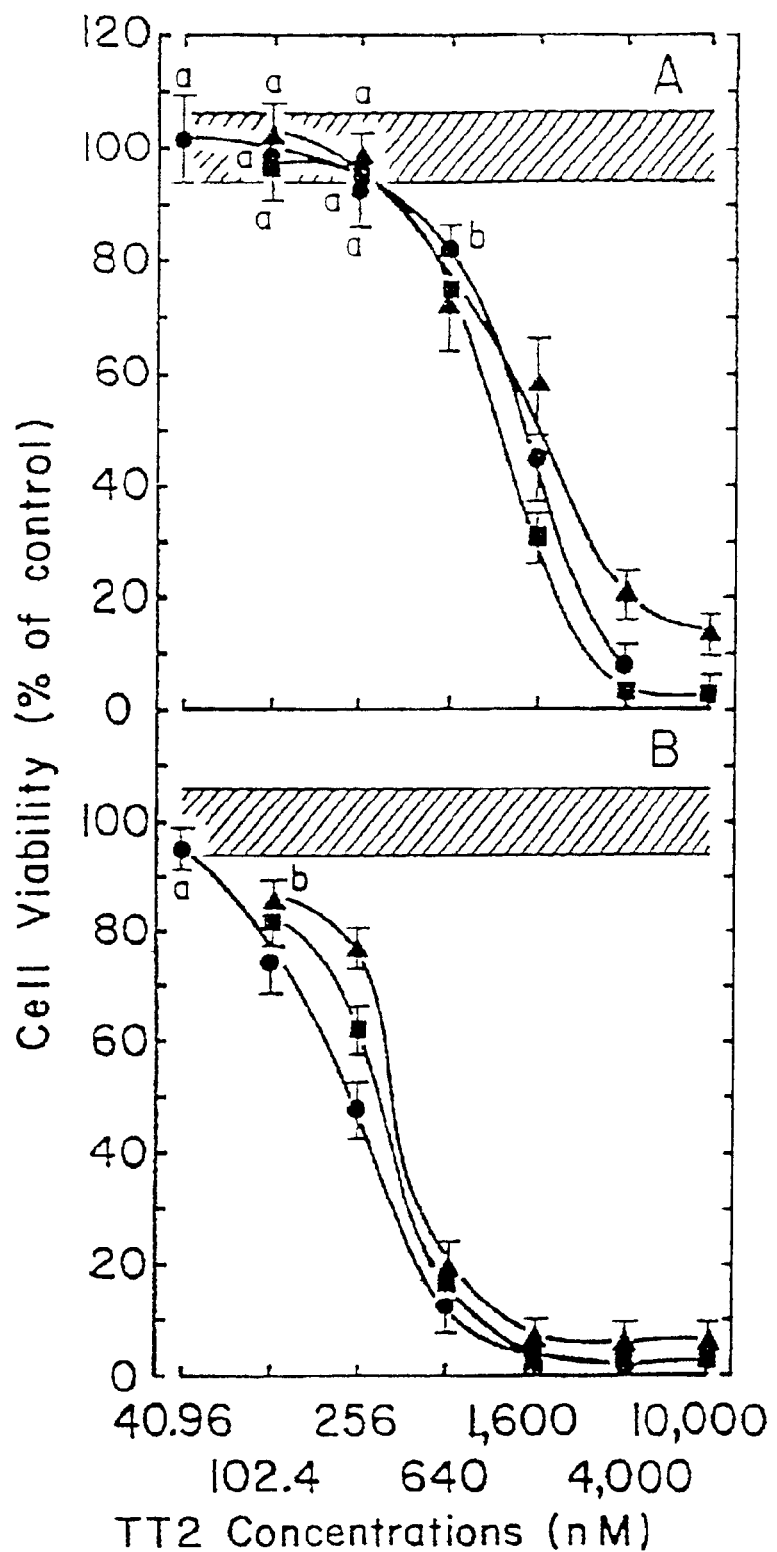
FIG. 8. Comparison of the concentration-dependent inhibitions of HL-60-S (●), HL-60-RV (■) and HL-60-R8 (▲) cell viability by TT2 at days 2 (A) and 4 (B) in vitro. The conditions of the experiments and the determination of the results were identical to those of FIG. 5. Bars: means±SD (n=3). $^a$Not different from control; $^b$P<0.025, smaller than control.

Since DAU decreases the viability of HL-60-S, HL-60-RV and HL-60-R8 cells with respective IC$_{50}$ values of 80, 1,900 and 2,500 nM at day 2 (RFs: 23.8–31.3) and 15, 450 and 380 at day 4 (RFs: 25.3–30.0), this drug is about 28 times less potent as a cytotoxic agent in MDR than in WT HL-60 cells (FIG. 7). In contrast, TT2 reduces cell viability as effectively in HL-60-S (IC$_{50}$: 1,300 and 230 nM at days 2 and 4) as in HL-60-RV (IC$_{50}$: 1,100 and 340 nM at days 2 and 4) and HL-60-R8 (IC$_{50}$: 1,600 and 350 nM at days 2 and 4) cells (FIG. 8). Such negligible RFs (0.9–1.2 at day 2 and 1.5 at day 4) demonstrate that the cytotoxic potency of TT2 persists in MDR tumor sublines that have become 28 times less sensitive to the cytotoxic activity of DAU (FIG. 8).

Inhibition of DNA Synthesis and Nucleoside Transport by TTs

L1210

Figure 9:
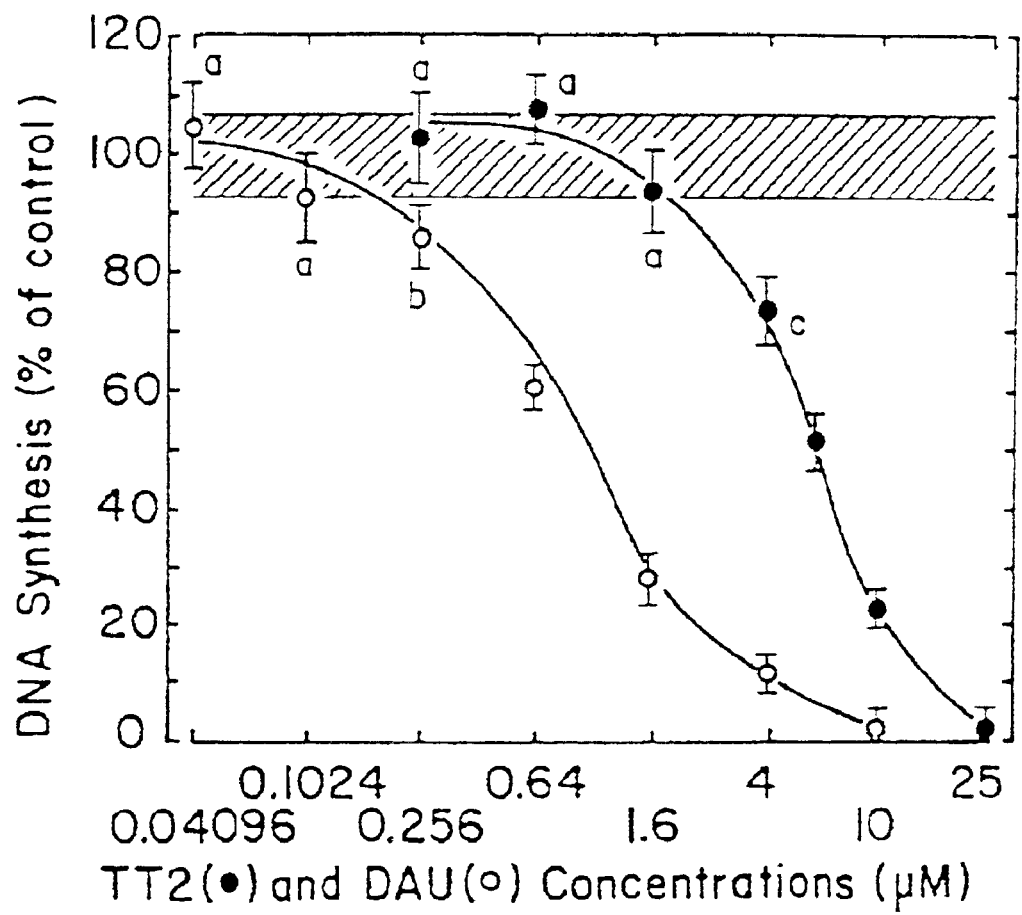
FIG. 9. Comparison of the concentration-dependent inhibitions of DNA synthesis by the TT analog TT2 (●) and DAU (○) in L1210 cells in vitro. Cells (1.14×10$^6$/0.5 ml of RPMI 1640 medium) were incubated at 37° C. for 90 min in the presence or absence (control) of the indicated concentrations of drugs, which are plotted on a logarithmic scale, and then pulse-labeled for an additional 30 min to determine the rate of $^3$H-thymidine incorporation into DNA. DNA synthesis in vehicle-treated control cells was 27,860±1,931 cpm (100±7%; striped area). The blank value (916±52 cpm) for cells incubated and pulse-labeled at 2° C. with 1 μCi of $^3$H-thymidine has been substracted from the results. Bars: means±SD (n=3). $^a$Not different from control; $^b$P<0.05 and $^c$P<0.01, smaller than control.

A 2-h treatment with TT2 is sufficient to inhibit, in a concentration-dependent manner, the rate of DNA synthesis determined over a 30-min period of pulse-labeling in L1210 cells in vitro (FIG. 9). DNA synthesis is totally inhibited by 25 $\mu$M TT2 but, as compared to DAU which becomes effective against DNA synthesis at 0.256 $\mu$M, concentrations greater than 1.6 $\mu$M must be used to demonstrate the inhibitory effect of TT2 on DNA synthesis. Hence, the concentration-dependent inhibitions of DNA synthesis by DAU ($IC_{50}$: 1 $\mu$M) and TT2 ($IC_{50}$: 6 $\mu$M) suggest that, under these experimental conditions, DAU prevents L1210 cells from synthesizing DNA about 6 times more effectively than TF2 (FIG. 9).

Figure 10:
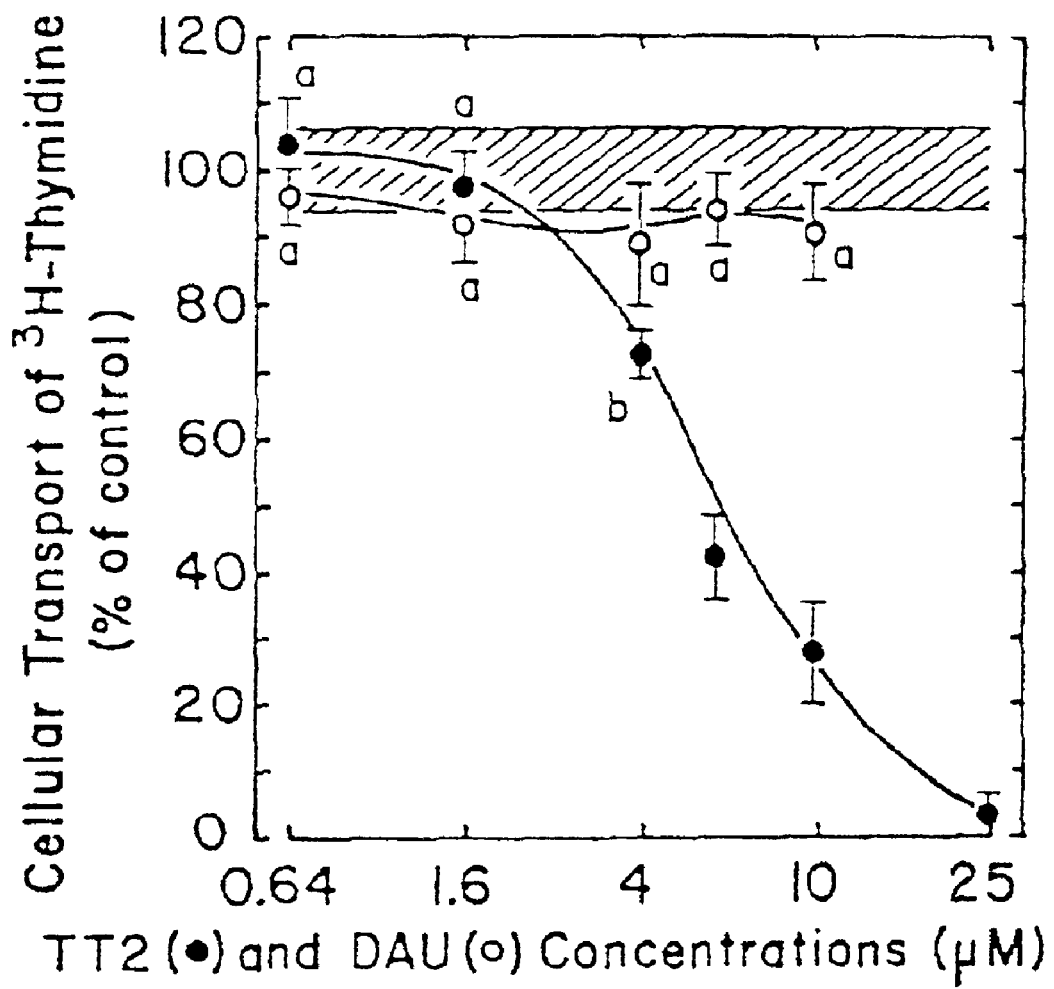
FIG. 10. Concentration-dependent inhibition of nucleoside transport by the TT analog TT2 in L1210 cells in vitro. Cells (1.48×10$^6$/0.5 ml of RPMI 1640 medium) were preincubated for 15 min at 37° C. in the presence or absence (control) of the indicated concentrations of TT2 (●) and DAU (○), which are plotted on a logarithmic scale, before being exposed to 1 μCi of $^3$H-thymidine for 30 sec at 37° C. After washing thrice with PBS, intact cell pellets were harvested by centrifugation, incubated for 30 min in 1 ml of HLB containing 0.2% Triton X-100, and these lysates were mixed with scintillation cocktail and counted to estimate the cellular uptake of $^3$H-thymidine. Results are expressed as % of $^3$H-thymidine transported into vehicle-treated control cells over 30 sec (15,031±872 cpm; 100±6%; striped area). Bars: means±SD (n=3). $^a$Not different from control; $^b$P<0.005, smaller than control.

A critical finding is that, in contrast to DAU which serves as a negative control in the assay, a 15-min treatment with TT2 is sufficient to block, in a concentration-dependent manner, the cellular transport of $^3$H-thymidine occuring over only 30 sec in vitro (FIG. 10). Nucleoside transport is totally inhibited in L1210 cells treated with 25 $\mu$M TT2. But 10 $\mu$M DAU is totally unable to alter the cellular transport of $^3$H-thymidine (FIG. 10), even though such concentration of DAU inhibits maximally the incorporation of $^3$H-thymidine into DNA (FIG. 9). Interestingly, the concentration-response curves for the inhibitory effects of TT2 on nucleoside transport (FIG. 10) and DNA synthesis (FIG. 9) are nearly identical and share similar $IC_{50}$ values of 6 $\mu$M, suggesting that the inhibition of $^3$H-thymidine incorporation into DNA caused by TT2 at 2 h (FIG. 9) may largely be due to the ability of this TT quinone to immediately block the uptake of $^3$H-thymidine by the cells (FIG. 10).

Figure 11:
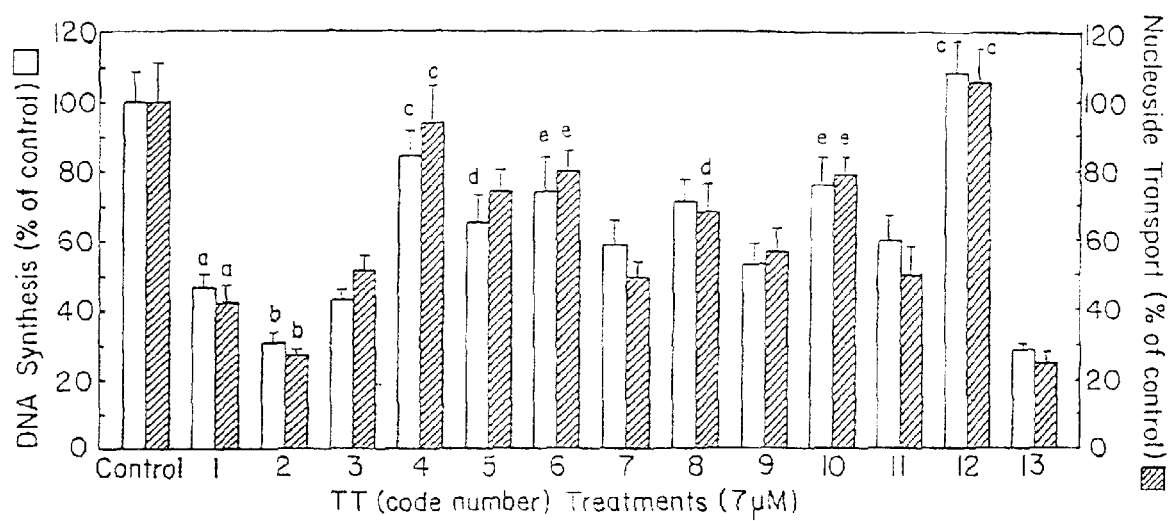
FIG. 11. Comparison of the inhibitory effects of novel TT analogs on DNA synthesis (open) and nucleoside transport (striped) in L1210 cells in vitro. The cellular uptake of $^3$H-thymidine (striped) and the rate of $^3$H-thymidine incorporation into DNA (open) were determined in cells (1.38× 10$^6$/0.5 ml of RPMI 1640 medium) respectively preincubated at 37° C. for 15 or 90 min in the presence or absence (control) of 7 μM concentrations of the indicated compounds. For the cellular transport of nucleosides, preincubated cells were then exposed to 1 μCi of $^3$H-thymidine for 30 sec at 37° C. Results are expressed as % of $^3$H-thymidine transported into vehicle-treated control cells over 30 sec (15,539±1,767 cpm; 100±11%; striped control). For DNA synthesis, preincubated cells were then pulse-labeled with 1 μCi of $^3$H-thymidine for an additional 30 min at 37° C. Results are expressed as % of $^3$H-thymidine incorporation into DNA in vehicle-treated control cells over 30 min (28,505±2,594 cpm; 100±9%; open control). The blank value (1,075±171 cpm) for cells incubated and pulse-labeled at 2° C. with 1 μCi of $^3$H-thymidine has been substracted from the results. Bars: means±SD (n=3). $^a$Not different from TT3, TT7, TT9 and TT11; $^b$P<0.01, smaller than TT1 but not different from TT13; $^c$not different from control; $^d$P<0.025, greater than TT1; $^e$P<0.05, smaller than control.

Moreover, when compared on an equal 7 $\mu$M concentration basis, the different magnitudes at which various TTs inhibit DNA synthesis at 2 h correlate with the different abilities of these compounds to block the cellular transport of nucleosides after 15 min (FIG. 11). Indeed, among all TTs tested at this concentration, TT4 and TT12 alter neither DNA synthesis nor nucleoside transport, whereas TT2 and TT13, which block the most the cellular transport of $^3$H-thymidine (72–75% inhibition), are also the most potent against the incorporation of $^3$H-thymidine into DNA (69–71% inhibition) (FIG. 11). Under similar conditions, TT1, TT3, TT7, TT9 and TT11 inhibit nucleoside transport by 44–57% and DNA synthesis by 41–58%, whereas TT5, TT6, TT8 and TT10 are less effective, inhibiting both responses in the 20–35% range only (FIG. 11).

Figure 12:
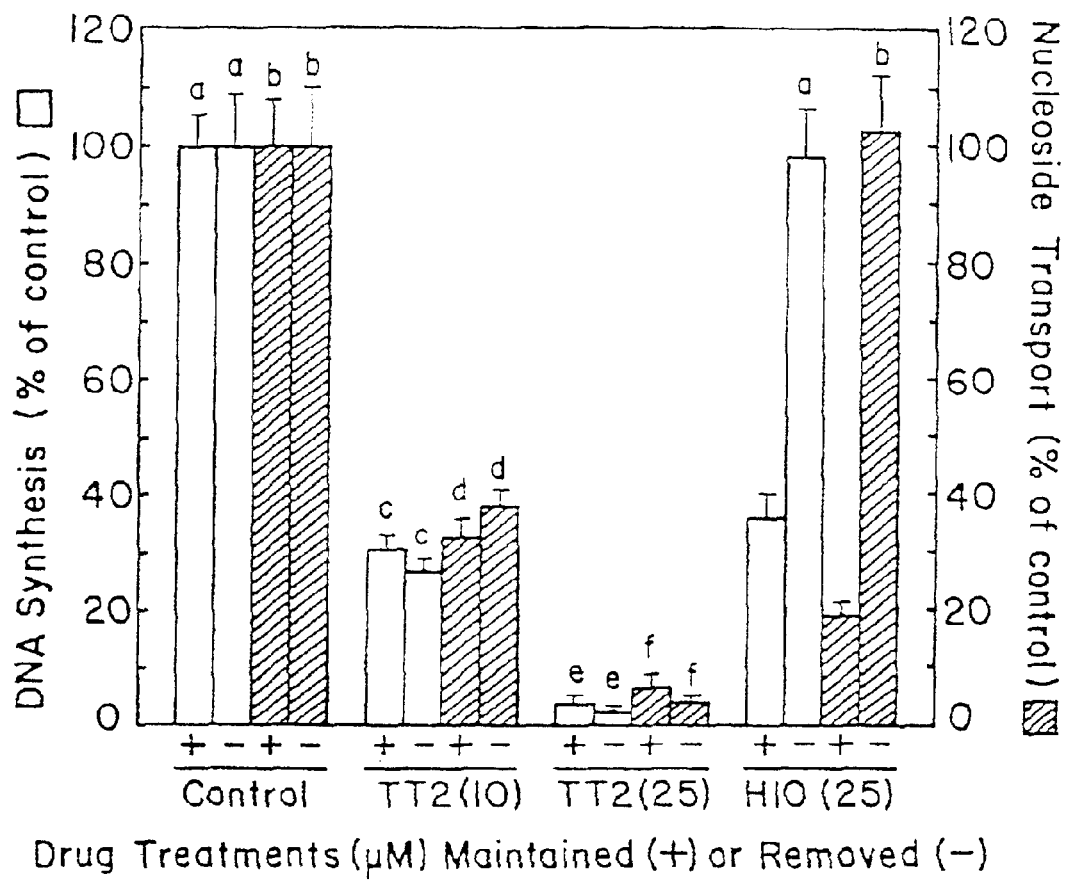
FIG. 12. Irreversibility of the inhibitory effects of the novel TT analog TT2 on DNA synthesis (open) and nucleoside transport (striped) in L1210 cells in vitro. The reversible inhibitory effects of the tricyclic pyrone H10 are demonstrated in the same experiment. The cellular uptake of $^3$H-thymidine (striped) and the rate of $^3$H-thymidine incorporation into DNA (open) were determined in cells (1.64× 10$^6$/0.5 ml of RPMI 1640 medium) respectively preincubated at 37° C. for 15 or 60 min in the presence or absence (control) of 10 and 25 μM TT2 or 25 μM H10. The protocol of the experiments and the determination of the results were identical to those of FIGS. 9 and 10, except that, after preincubation, either the drugs were maintained in the culture medium (+) or the cells were spun, washed, and resuspended in fresh medium in order to remove the drugs (−). After preincubation, vehicle-treated controls were similarly spun and washed. For the cellular transport of nucleosides, preincubated cells were then exposed, in the presence (+) or absence (−) of TT2 or H10, to 1 μCi of $^3$H-thymidine for 30 sec at 37° C. Results are expressed as % of $^3$H-thymidine transported into vehicle-treated control cells over 30 sec (11,054±754 cpm; 100±7%; striped control+; 14,486±1,260 cpm; 100±9%; striped control−). For DNA synthesis, preincubated cells were then pulse-labeled with 1 μCi of $^3$H-thymidine for an additional 30 min at 37° C. in the presence (+) or absence (−) of TT2 or H10. Results are expressed as % of $^3$H-thymidine incorporation into DNA in vehicle-treated control cells over 30 min (34,052±1,566 cpm; 100±5%; open control+; 28,811±2,506 cpm; 100±9%; open control−). The blank value (1,328±86 cpm) for cells incubated and pulse-labeled at 2° C. with 1 μCi of $^3$H-thymidine has been substracted from the results. Bars: means±SD (n=3). Values with similar superscripts are not significantly different from each others.

Finally, the abilities of 10 and 25 $\mu$M TT2 to respectively inhibit nucleoside transport by 67 and 93% and DNA synthesis by 69 and 97% are both irreversible upon drug removal (FIG. 12), suggesting that, after a 15- to 60-min pretreatment, the presence of TT quinone in the culture medium is no longer required to continually block the cellular transport of $^3$H-thymidine and thereby prevent its incorporation into DNA. For the sake of comparison, the inhibitions of nucleoside transport and DNA synthesis caused by the novel tricyclic pyrone analog H10, which are fully reversible upon drug removal, are demonstrated as a positive control under similar experimental conditions in the L1210 tumor assay system (FIG. 12).

Figure 13:
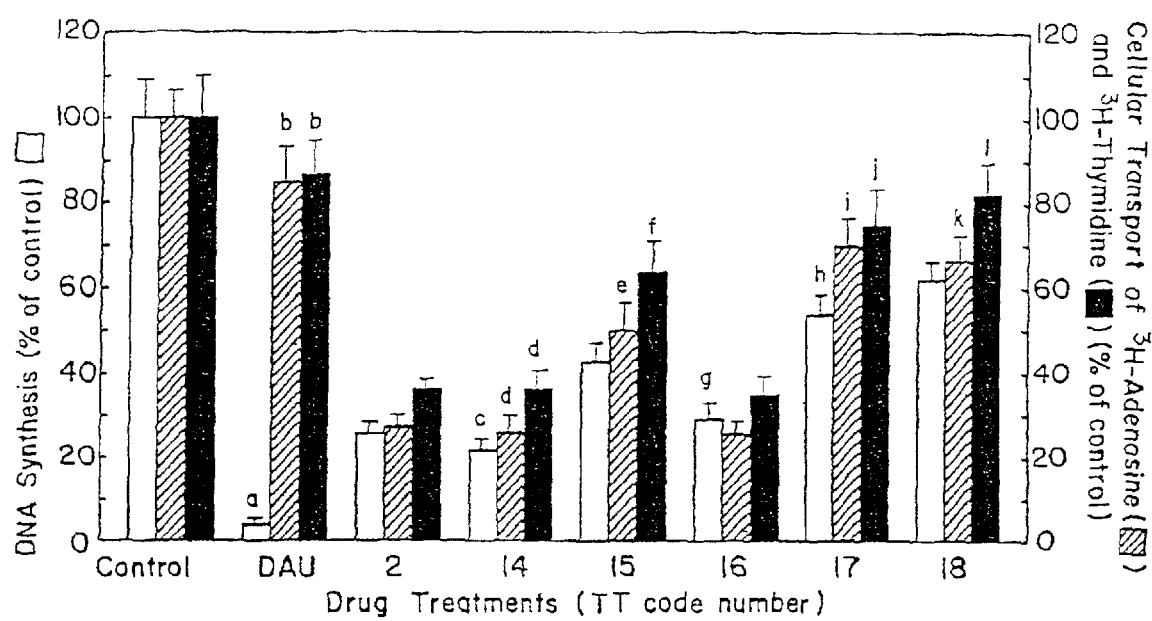
FIG. 13. The open columns represents the rate of $^3$H-Thymidine incorporation into DNA over 30 minutes, whereas the striped and closed columns represents the cellular transport of $^3$H-adenosine and $^3$H-thymidine occurring over only 30 seconds in vitro.

As shown in FIG. 13, TT16 is as potent as TT2 on both DNA synthesis and the cellular transport of adenosine and thymidine.

HL

Figure 14:
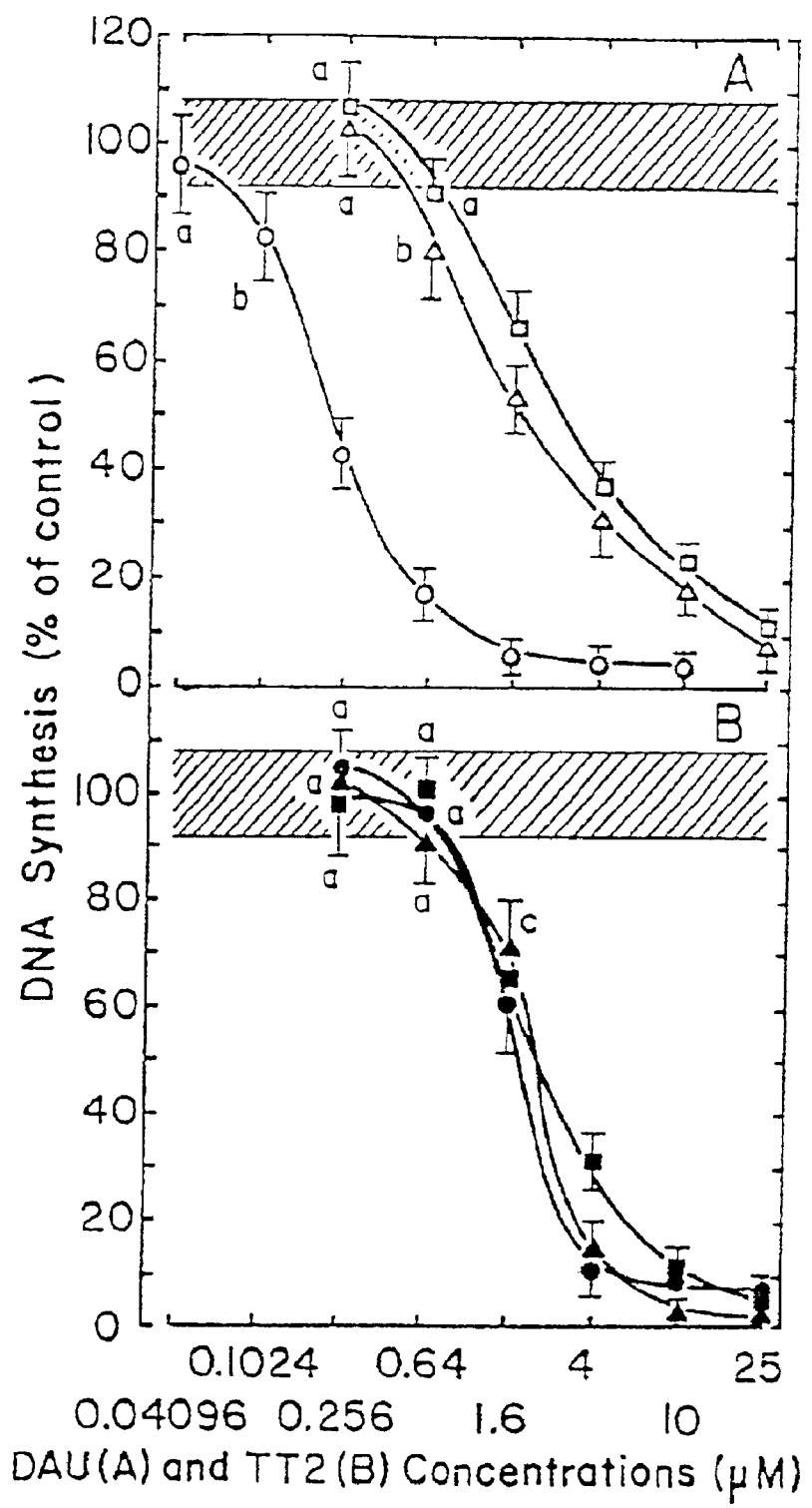
FIG. 14. Comparison of the concentration-dependent inhibitions of DNA synthesis by DAU (open symbols in A) and TT2 (closed symbols in B) in HL-60-S (circles), HL-60-RV (squares) and HL-60-R8 (triangles) cells in vitro. DNA synthesis in vehicle-treated control cells was 14,269±1,106 cpm (100±8%, striped areas). The blank value (404±38 cpm) for control cells incubated and pulse-labeled at 2° C. with 1 μCi of $^3$H-thymidine has been substracted from the results Bars: means±SD (n=3). $^a$Not different from control; $^b$P<0.05 and $^c$P<0.025, smaller than control.

The concentration-dependent inhibitions of DNA synthesis by DAU in HL-60-S ($IC_{50}$: 0.21 $\mu$M), HL-60-RV ($IC_{50}$: 2.5 $\mu$M) and HL-60-R8 ($IC_{50}$: 1.7 $\mu$M) cells are characterized by RF values of 8.1–11.9 (FIG. 14A). In contrast, TT2 inhibits the rate of incorporation of $^3$H-thymidine into DNA as effectively in HL-60-S ($IC_{50}$: 1.8 $\mu$M) as in HL-60-RV ($IC_{50}$: 2.1 $\mu$M) and HL-60-R8 ($IC_{50}$: 2.1 $\mu$M) cells and there are no significant RFs (1.2), indicating that TT2 maintains its ability to inhibit DNA synthesis in MDR tumor sublines that have become 10 times less sensitive to the action of DAU (FIG. 14B).

Figure 15:
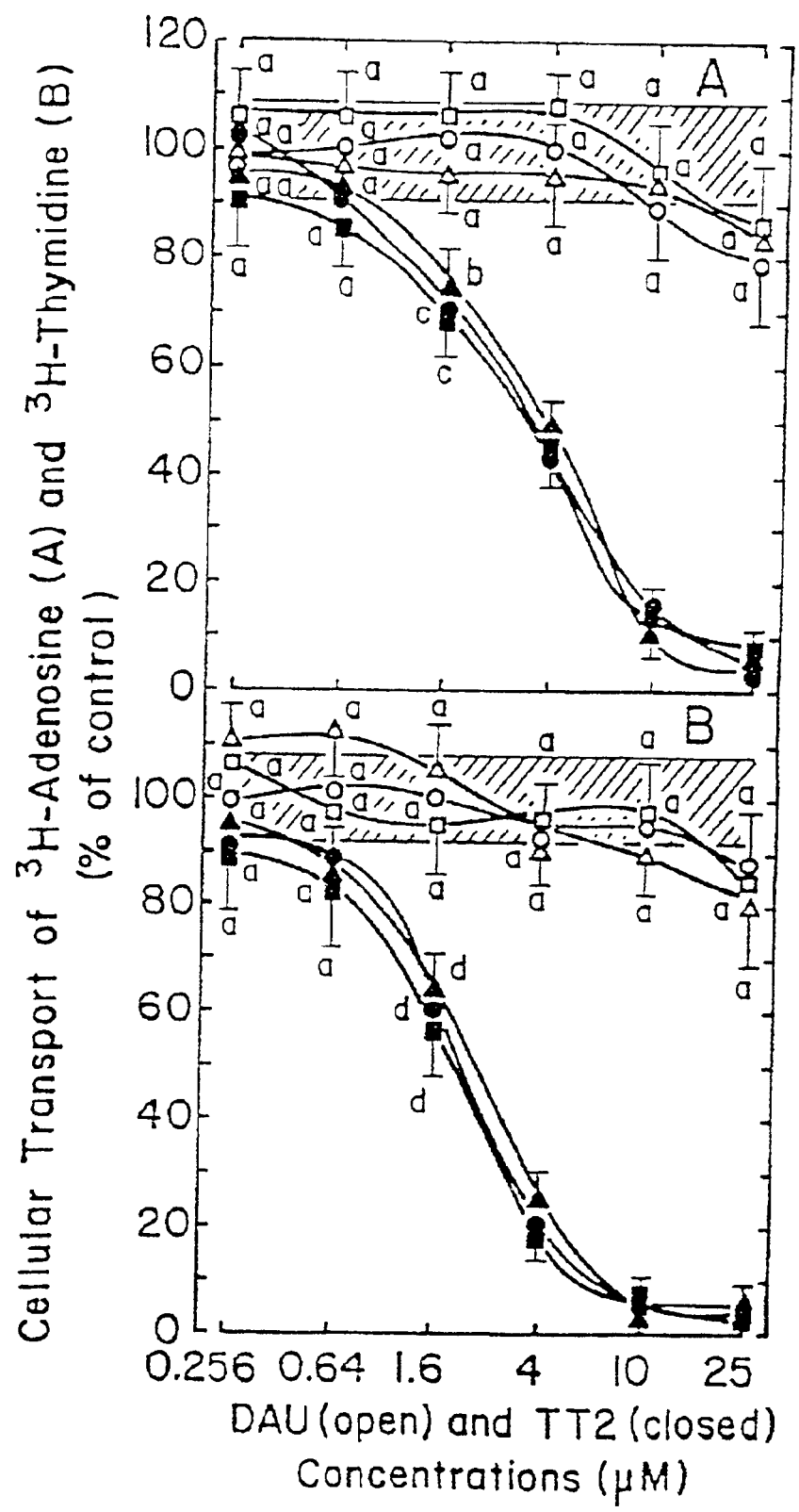
FIG. 15. Comparison of the concentration-dependent inhibitions of the cellular transport of purine (A) and pyrimidine (B) nucleosides by DAU (open symbols) and TT2 (closed symbols) in HL-60-S (circles), HL-60-RV (squares) and HL-60-R8 (triangles) cells in vitro. Results are expressed as % of $^3$H-adenosine (26,032±2,239 cpm, 100±9%, striped area in A) and $^3$H-thymidine (17,934±1, 398 cpm, 100±8%, striped area in B) transported into vehicle-treated control cells over 30 s. Bars: means±SD (n=3). $^a$Not different from control; $^b$P<0.025, $^c$P<0.01 and $^d$P<0.005, smaller than control.

DAU, which fails to significantly inhibit nucleoside transport in WT HL-60-S parental cells, is also unable to do so in their two MDR sublines (FIG. 15). In contrast, TT2 is a quinone antitumor drug that has the advantage of rapidly blocking, in a concentration-dependent manner, the cellular transport of both purine and pyrimidine nucleosides in HL-60-S cells (FIG. 15). Moreover, the ability of TT2 to prevent the cellular transport of $^3$H-adenosine and $^3$H-thymidine in WT HL-60-S cells ($IC_{50}$: 3.3 and 2.0 $\mu$M, respectively) fully persists (RFs: 1.0–1.2) in both the MDR HL60-RV ($IC_{50}$: 3.2 and 2.0 $\mu$M, respectively) and HL-60-R8 ($IC_{50}$: 3.7 and 2.3 $\mu$M, respectively) cell lines (FIG. 15).

Inhibition of RNA and Protein Syntheses by TTs

Figure 16:
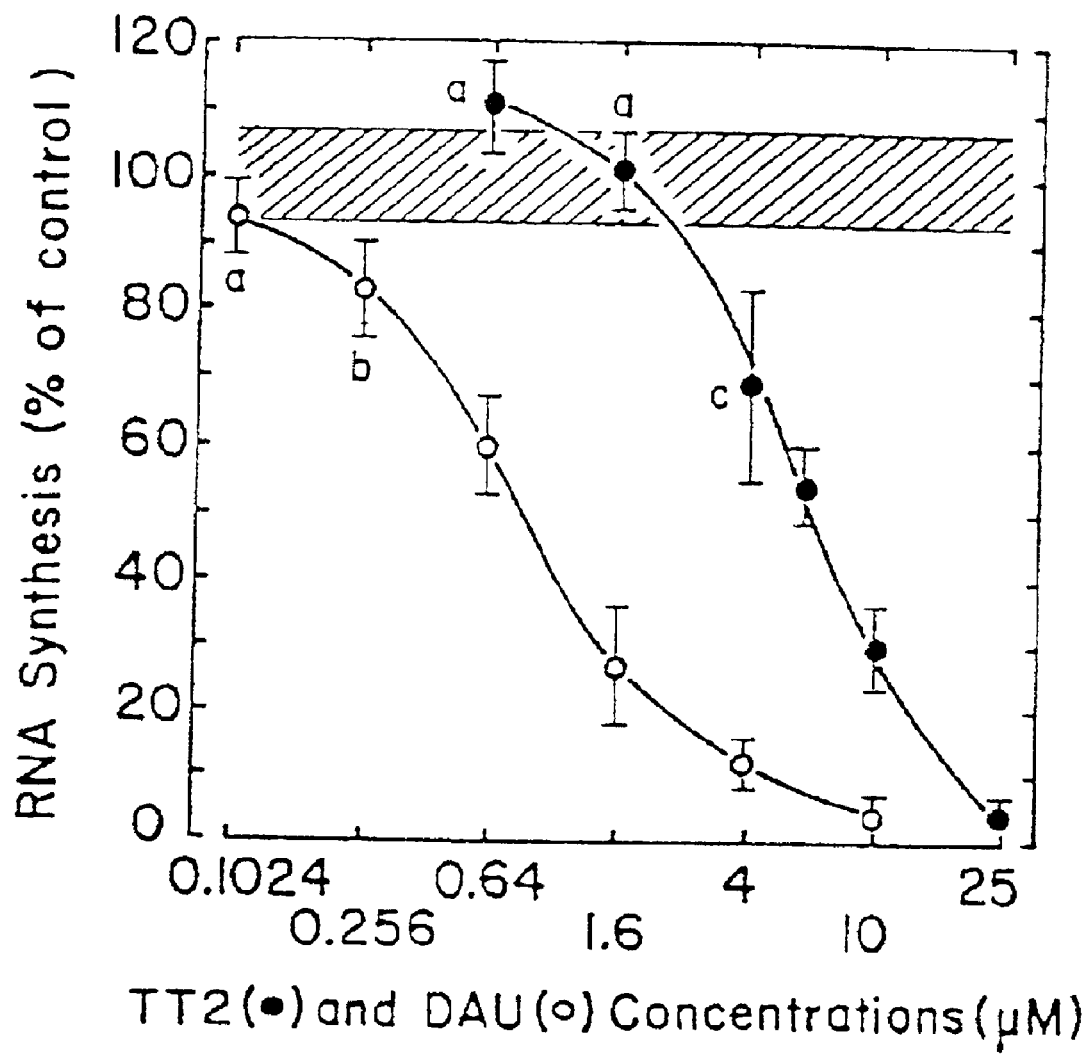
FIG. 16. Comparison of the concentration-dependent inhibitions of RNA synthesis by the TT analog TT2 (●) and DAU (○) in L1210 cells in vitro. Cells (1.2×10$^6$/0.5 ml of RPMI 1640 medium) were incubated at 37° C. for 3 h in the presence or absence (control) of the indicated concentrations of drugs, which are plotted on a logarithmic scale, and then pulse-labeled for an additional 1 h to determine the rate of $^3$H-uridine incorporation into RNA. RNA synthesis in vehicle-treated control cells was 47,117±3,204 cpm (100±7%; striped area). The blank value (1,746±155 cpm) for cells incubated and pulse-labeled at 2° C. with 2 μCi of $^3$H-uridine has been substracted from the results. Bars: means±SD (n=3). $^a$Not different from control; $^b$P<0.05 and $^c$P<0.025, smaller than control.
Figure 17:
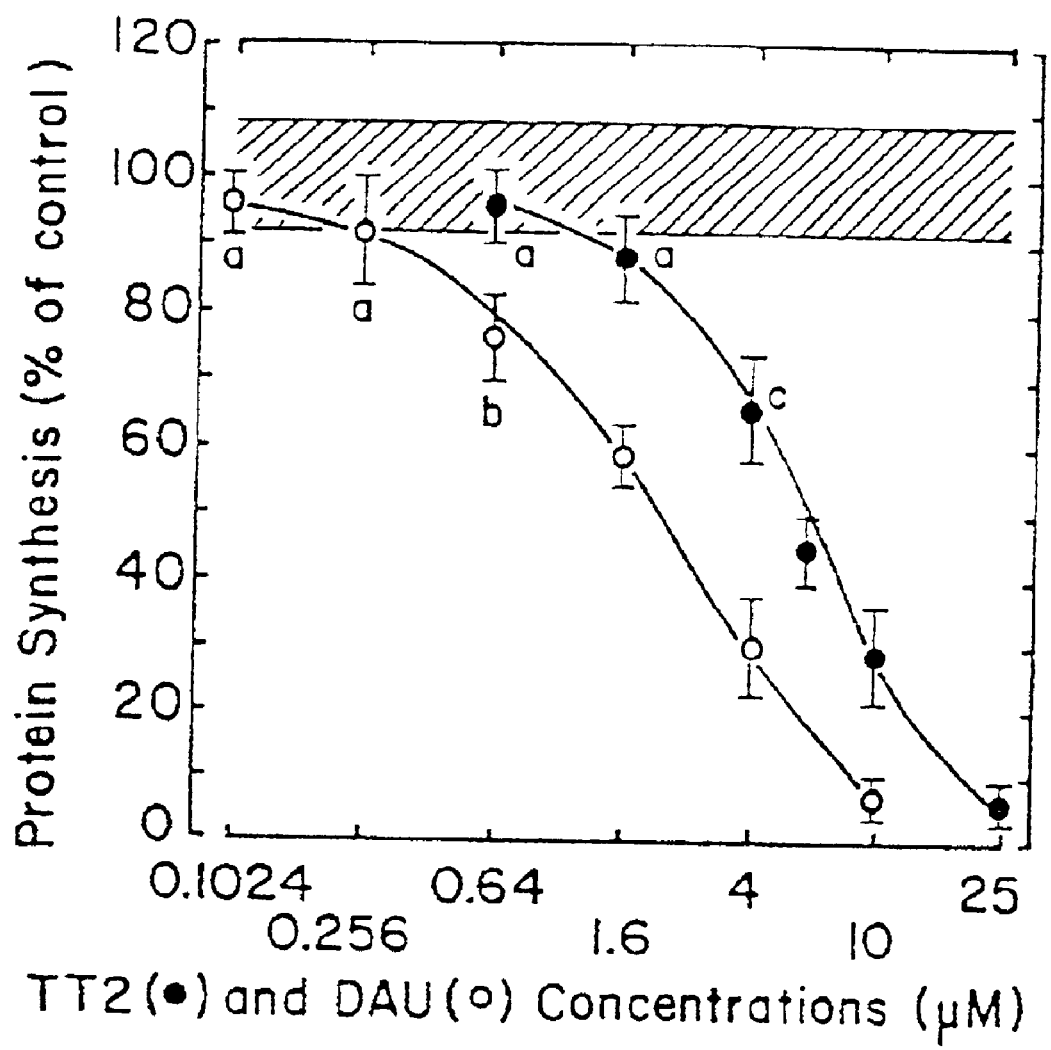
FIG. 17. Comparison of the concentration-dependent inhibitions of protein synthesis by the TT analog TT2 (●) and DAU (○) in L1210 cells in vitro. Cells (1.51×10$^6$/0.5 ml of RPMI 1640 medium) were incubated at 37° C. for 3 h in the presence or absence (control) of the indicated concentrations of drugs, which are plotted on a logarithmic scale, and then pulse-labeled for an additional 1 h to determine the rate of $^3$H-leucine incorporation into protein. Protein synthesis in vehicle-treated control cells was 13,812±1,070 cpm (100±8%; striped area). The blank value (2,436±298 cpm) for cells incubated and pulse-labeled at 2° C. with 2.5 μCi of $^3$H-leucine has been substracted from the results. Bars: means±SD (n=3). $^a$Not different from control; $^b$P<0.025 and $^c$P<0.01, smaller than control.

Besides DNA synthesis, a 3-h treatment with TT2 can also inhibit, in a concentration-dependent manner, the rates of RNA (FIG. 16) and protein (FIG. 17) syntheses determined over 60-min periods of pulse-labeling in L1210 cells in vitro. The concentration-response curves for the inhibitions of RNA (FIG. 16) and protein (FIG. 17) syntheses by TT2 are nearly identical to that for the inhibition of DNA synthesis (FIG. 8): concentrations of TT2 greater than 1.6 $\mu$M must be used to demonstrate effectiveness, total inhibition is achieved at 25 $\mu$M, and the $IC_{50}$ value in all cases is about 6 $\mu$M. Under similar conditions, DAU inhibits the respective syntheses of RNA ($IC_{50}$: 0.8 $\mu$M) and protein ($IC_{50}$: 2 $\mu$M) about 7.5 and 3 times more effectively than TT2 (FIGS. 16 & 17).

Effects of TTs on the Mitotic Index

Figure 18:
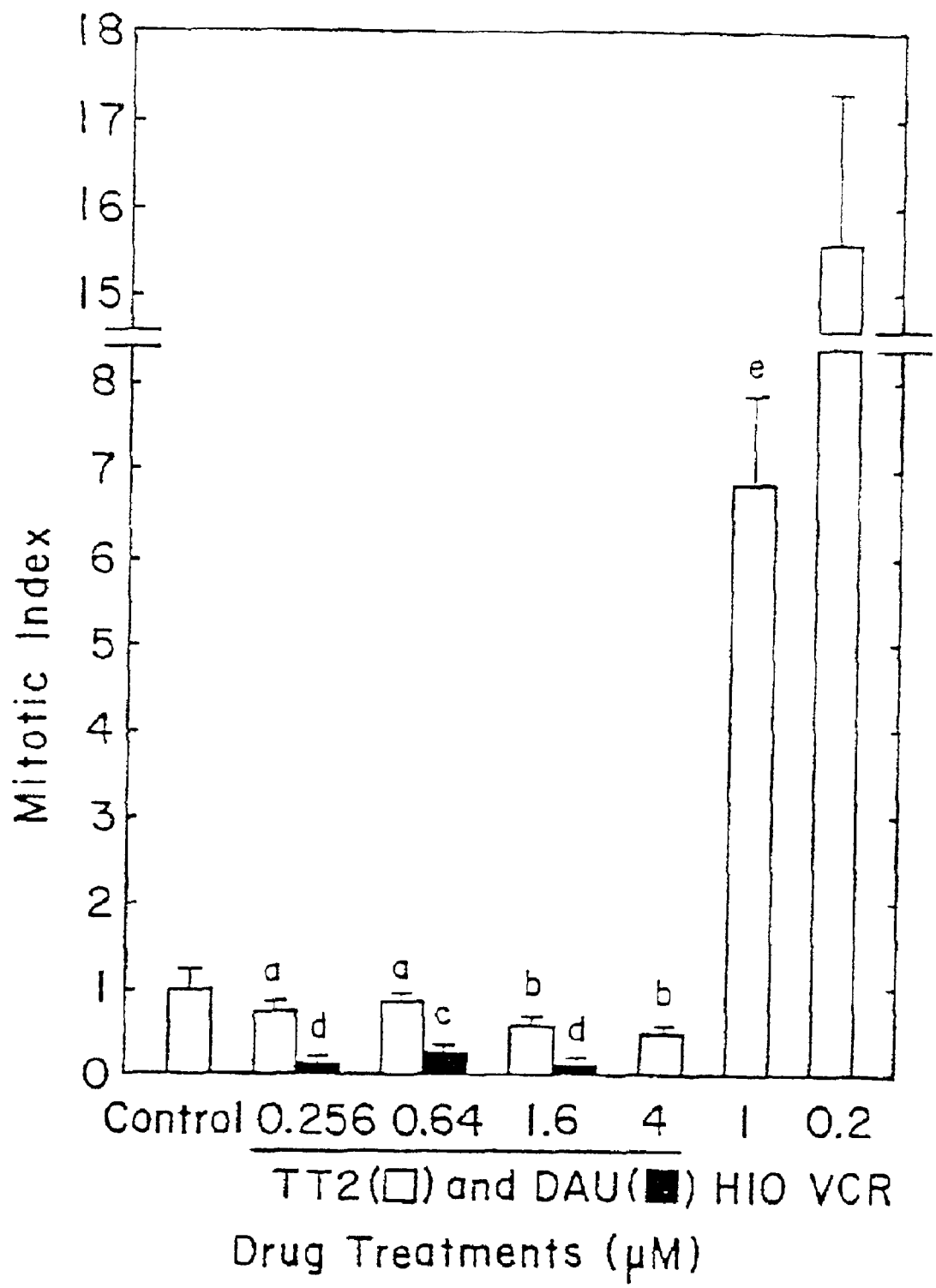
FIG. 18. Effects of the novel TT analog TT2 and DAU on the mitotic index of L1210 cells in vitro. The antimitotic activities of VCR and the tricyclic pyrone H10 are demonstrated in the same experiment. Cells (10$^6$/0.5 ml of RPMI 1640 medium) were incubated in triplicate for 24 h at 37° C. in the presence or absence (control) of 0.256, 0.64, 1.6 and 4 μM TT2, 0.256, 0.64 and 1.6 μM DAU, 0.2 μM VCR or 1 μM H10. After fixation with MeOH:acetic acid (3:1) and staining with 0.1% crystal violet, about 500 cells/slide were scored for mitotic figures and the mitotic index was expressed as the % of mitotic cells in drug-treated cultures divided by the % of mitotic cells in non-treated controls. The mean % of mitotic cells in control at 24 h was 1.86±0.43%. Bars: means±SD (n=3). $^a$Not different from control; $^b$P<0.05, $^c$P<0.01 and $^d$P<0.005, smaller than control; $^e$P<0.005, greater than control but smaller than VCR.

Control populations of L1210 cells cultured for 24 h in the absence of drugs contain only 1.86% of mitotic cells (FIG. 18). In relation with their ability to block tubulin polymerization and cell cycle progression in M-phase, 24-h treatments with VCR and the tricyclic pyrone H10 respectively produce 16- and 7-fold increases in the mitotic index (FIG. 18). Such known microtubule de-stabilizing anticancer drugs, therefore, serve as positive controls in this antimitotic assay. In contrast, none of the concentrations of TT2 tested, even those in the $\mu$M range that are highly cytostatic and cytotoxic at 24 h, are able to raise the mitotic index of L1210 cells (FIG. 18), suggesting that TT quinones are unlikely to be antimitotic drugs that disrupt microtubule dynamics to trigger their anticancer activity. In relation with its known ability to first accumulate cells in $G_2$ and then inhibit cell cycle traverse as its concentration increases, DAU actually decreases the % of mitotic cells by 74–91% (FIG. 18). Since the highest concentrations of TT2 tested significantly decrease the % of mitotic cells by 38–48% (FIG. 18), TTs might also prevent tumor cell cycle progression to mitosis.

Induction of DNA Cleavage by TTs

L1210

Figure 19:
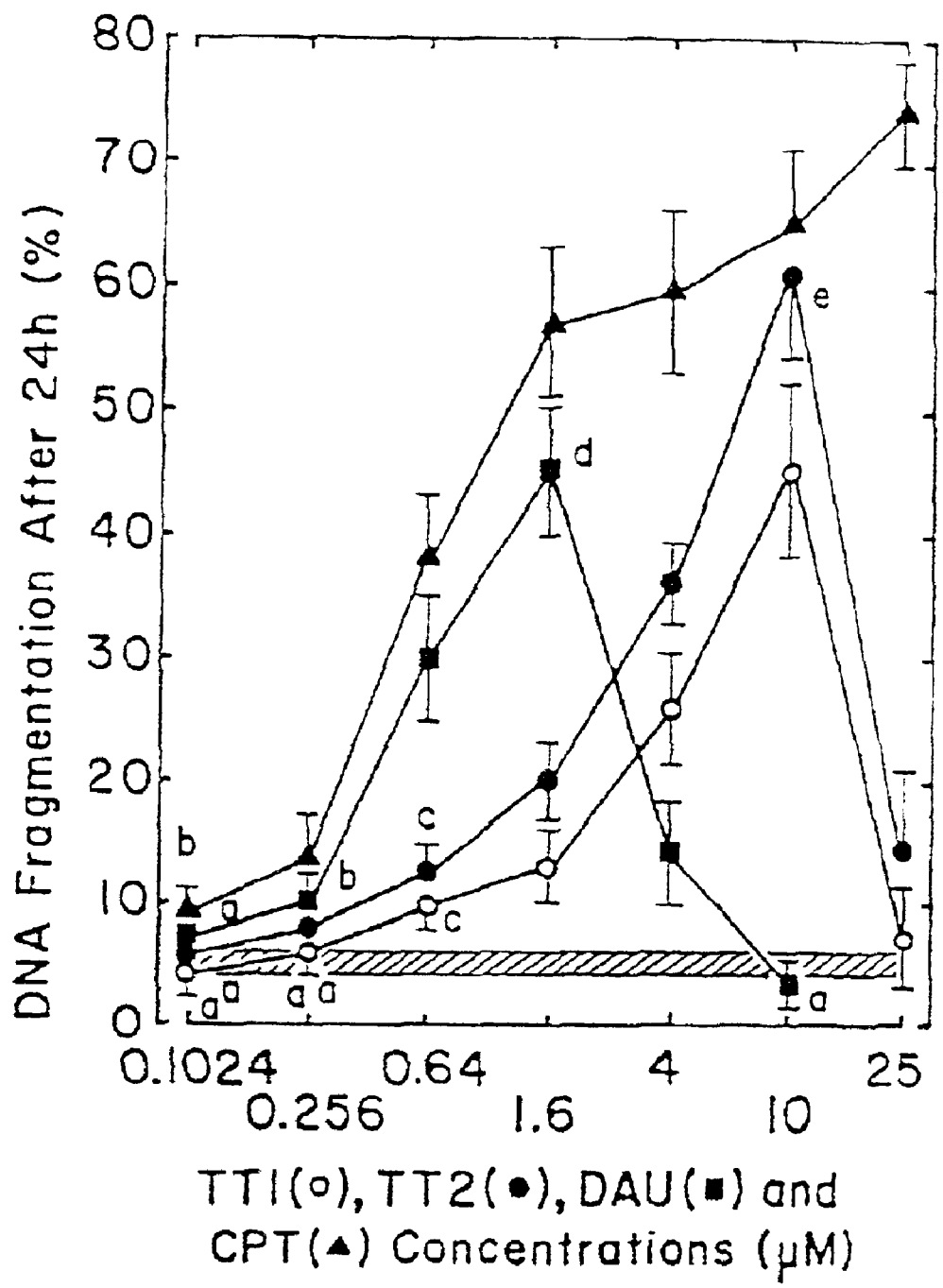
FIG. 19. Comparison of the concentration-dependent effects of novel TT analogs and known DNA-damaging anticancer drugs on DNA cleavage in L1210 cells in vitro. Cells (10$^6$/0.5 ml of RPMI 1640 medium) were prelabeled with 1 μCi of $^3$H-thymidine for 2 h, washed and resuspended in fresh FCS-containing medium, and incubated at 37° C. for 24 h in the presence or absence (control) of the indicated concentrations of TT1 (○), TT2 (●), DAU (■) or CPT (▲), which are plotted on a logarithmic scale. After lysing the cells in HLB containing 0.2% Triton X-100, the detergent-soluble DNA fragments present in the supernatants and the intact chromatin DNA remaining in the pellets were separated by centrifugation and their radioactivity estimated by LSC. Results are expressed as [cpm in supernatant/cpm in supernatant+pellet]×100 at 24 h. For untreated controls (5.3±0.6% DNA fragmentation; striped area), the supernatant is 741±79 cpm and the pellet is 13,293±1,446 cpm. Bars: means±SD (n=3). $^a$Not different from control; $^b$P<0.05 and $^c$P<0.01, greater than control; $^d$P<0.05, smaller than CPT but not different from 10 μM TT1; $^e$P<0.05, greater than TT1 but not different from CPT.

L1210 cells containing $^3$H-thymidine-prelabeled DNA were used to quantitatively determine whether TTs could induce DNA fragmentation over a 24-h period in vitro. CPT and DAU, two anticancer drugs known to induce DNA-strand breaks by respectively inhibiting Topo I and II activities, are used as positive controls in this DNA fragmentation assay (FIG. 19). As reported before with anthracycline quinone antibiotics, the concentration-dependent induction of DNA cleavage caused by 24-h DAU treatments is biphasic, peaking at 45% in response to 1.6 $\mu$M DAU but declining back to control level (5%) at higher concentrations of DAU (FIG. 19). In contrast, the concentration-dependent increase of DNA cleavage produced by 24 h CPT treatments reaches 57% in response to 1.6 $\mu$M CPT but remains at a plateau of maximal stimulation (60–70%) at higher concentrations of CPT (FIG. 19). After 24 h, the maximal levels of DNA cleavage caused by 10 $\mu$M TT1 (45%) and TT2 (61%) respectively match those induced by 1.6 $\mu$M DAU and CPT (FIG. 19). Although concentrations of TTs higher than those of DAU are required to induce such peak of DNA cleavage, the shape of the concentration-response curves for the ability of TT1 and TT2 to break DNA resembles more that of DAU than that of CPT (FIG. 19), suggesting that the DNA-damaging effects of TT quinones and DAU might share some similarity.

Figure 20:
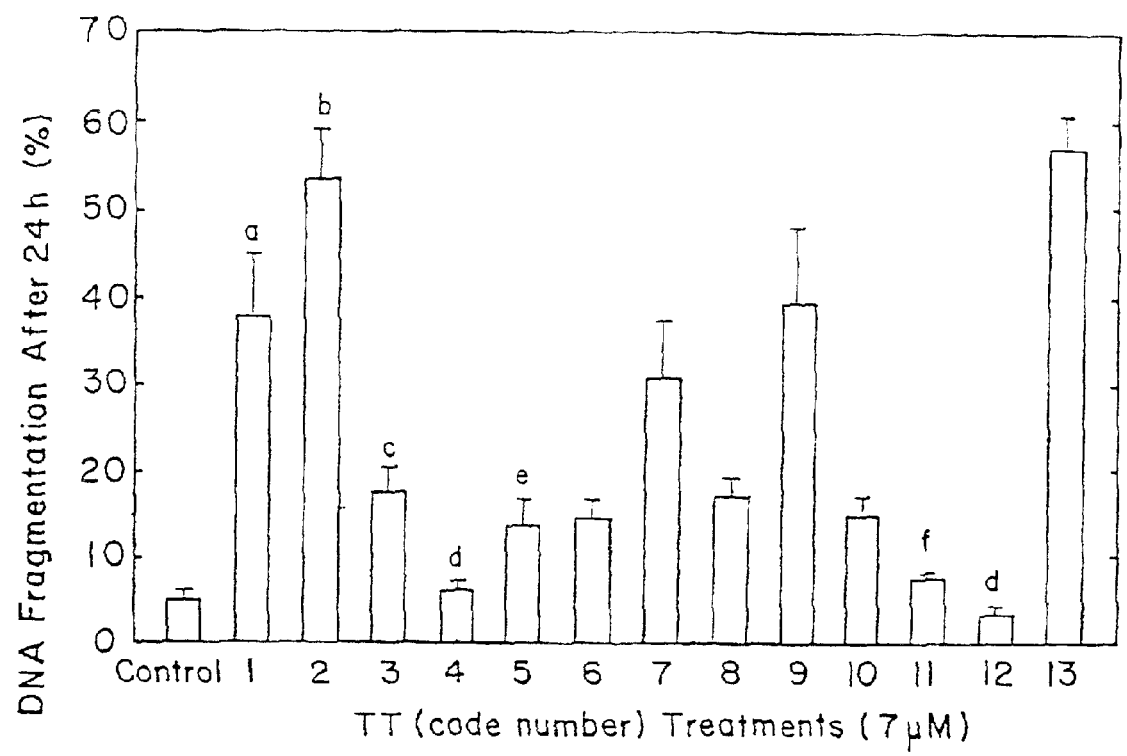
FIG. 20. Comparison of the abilities of novel TT analogs to induce DNA cleavage in L1210 cells in vitro. Cells containing prelabeled DNA were incubated at 37° C. for 24 h in the presence or absence (control) of 7 μM concentrations of the indicated compounds. The protocol of the experiment and the determination of the results were identical to those of FIG. 12. Bars: means±SD (n=3). $^a$Not different from TT7 and TT9; $^b$P<0.05, greater than TT9 but not different from TT13; $^c$P<0.05, smaller than TT7; $^d$not different from control; $^e$P<0.01, greater than control, P<0.025, greater than TT11 but not different from TT3, TT6, TT8 and TT10; $^f$P<0.01, greater than control.
Figure 21:
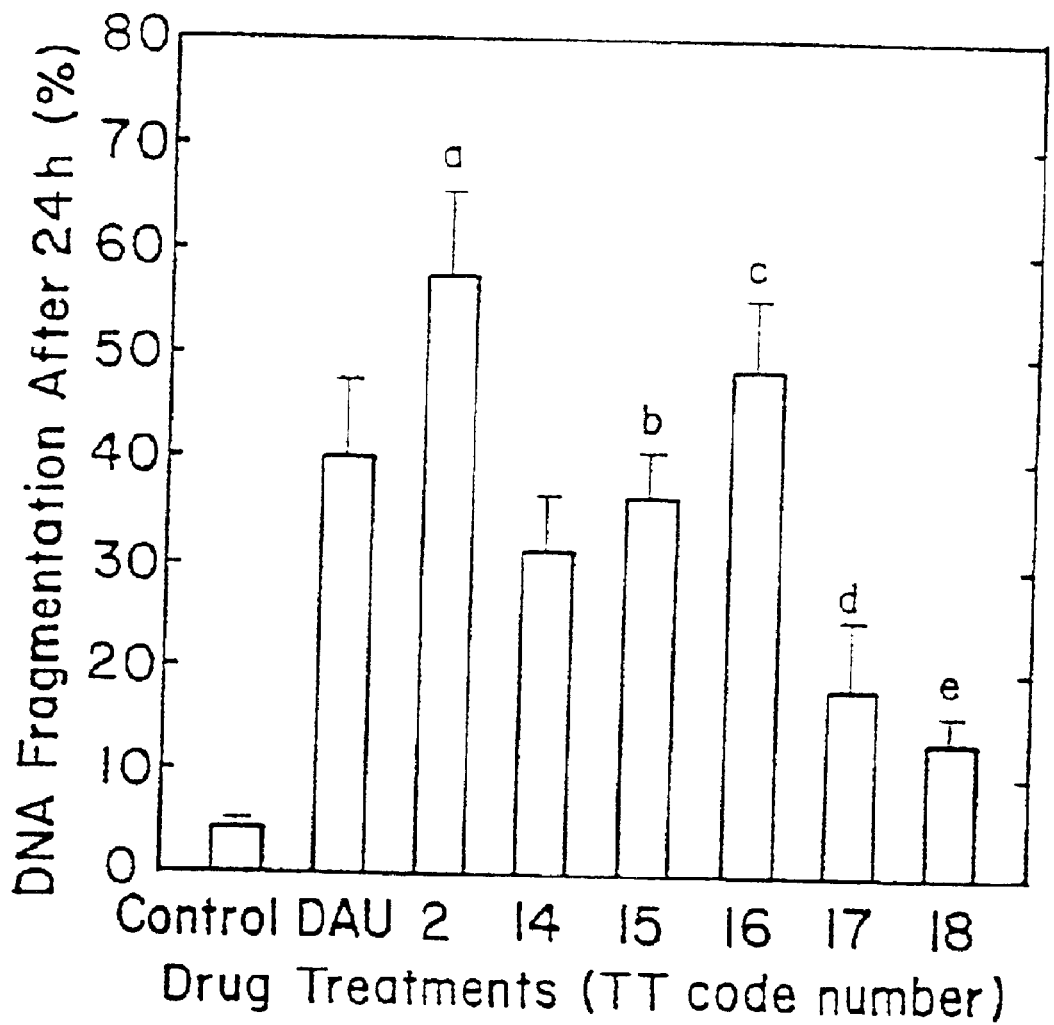
FIG. 21. Same experiment as FIG. 20 with additional analogs.

Overall, the different TTs compared at 7 $\mu$M induce various levels of DNA cleavage at 24 h (FIG. 20) in relation with their respective cytostatic and cytotoxic activities when tested at 256 nM for 4 days (FIG. 1). Indeed, TT2 and TT13, which are the most potent against L1210 cell proliferation and viability (FIG. 1), again induce the most DNA fragmentation (54–57%) after 24 h (FIG. 20), whereas TT4 and TT12, which have no antileukemic activity in the growth and viability assays (FIG. 1), also fail to significantly raise the level of DNA cleavage (4–6%) over control (5%) (FIG. 20). TT1, TT7 and TT9, which have good antileukemic activities (FIG. 1), also produce substantial levels of DNA fragmentation (31–40%) (FIG. 20). Moreover, the extent of DNA cleavage is only 14–18% in L1210 cells treated with TT3, TT5, TT6, TT8 or TT10 and the ability of TT11 to break DNA is minimal (7%) (FIG. 20), in relation with the weak and marginal antiproliferative and cytotoxic effects of these compounds in the L1210 system in vitro (FIG. 1). FIG. 21 shows the same experiment as in FIG. 20 with additional analogs.

Figure 22:
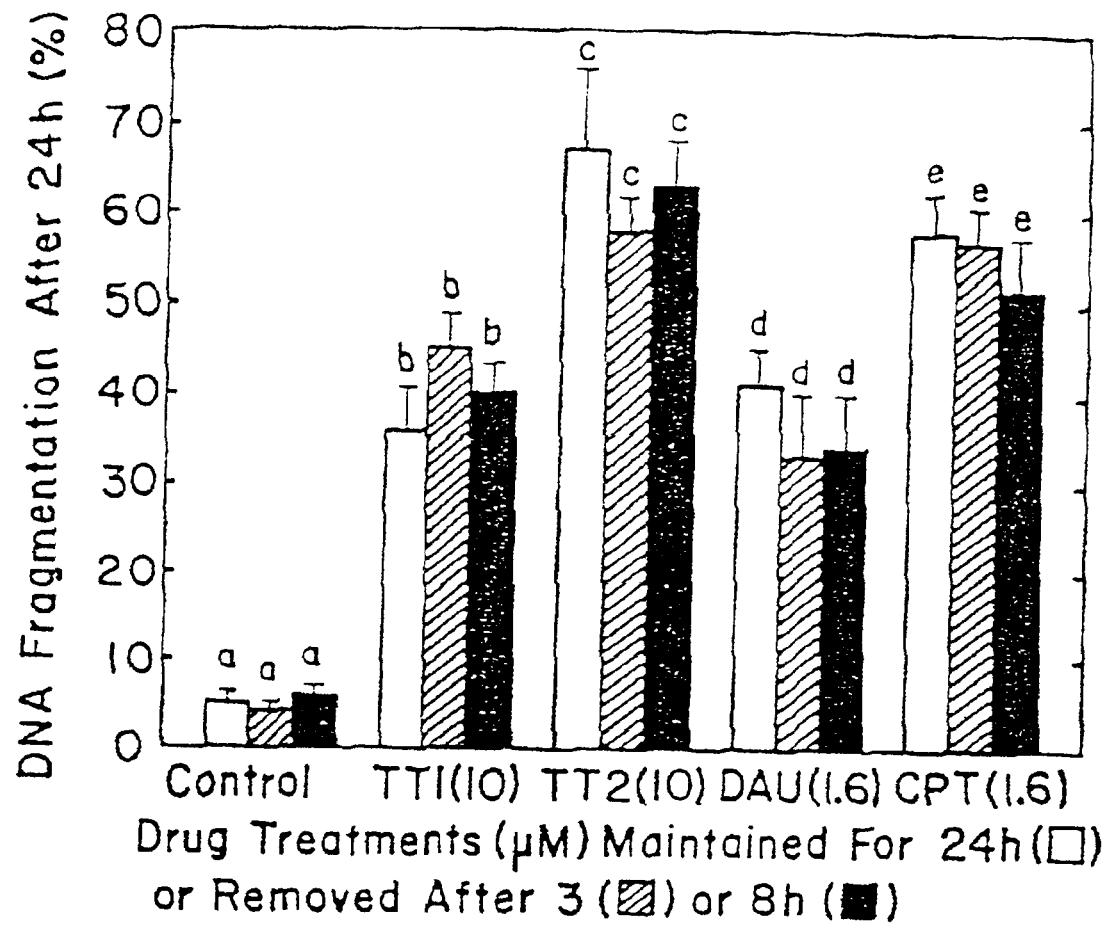
FIG. 22. Irreversibility of the effects of novel TT analogs and known DNA-damaging anticancer drugs on DNA cleavage in L1210 cells in vitro. Cells containing prelabeled DNA were incubated at 37° C. for various periods of time in the presence or absence (control) of 10 μM TT1 or TT2 and 1.6 μM DAU or CPT. The protocol of the experiment and the determination of the results at 24 h were identical to those of FIG. 19, except that the drugs were either maintained in the medium for the whole 24-h period of incubation (open) or removed after the first 3 (striped) and 8 h (closed). After spinning and washing the appropriate samples to remove the drugs, cells were resuspended in 0.5 ml of fresh medium to complete the 24-h period of incubation in the absence of drugs. Vehicle-treated controls were similarly spun and washed at 3 and 8 h. Bars: means±SD (n=3). Values with similar superscripts are not significantly different from each others. $^b$Not different from DAU; $^c$P<0.025, greater than TT1 but not different from CPT; $^d$P<0.05, smaller than CPT.

Finally, L1210 cells treated for only 3 and 8 h with 10 $\mu$M TT1 or TT2 have the same level of DNA fragmentation at 24 h (36–45% or 58–67%, respectively) than if they are exposed for the whole 24-h incubation period to TT1 or TT2 (40 or 63%, respectively) (FIG. 22). Under similar conditions, 1.6 $\mu$M DAU and CPT also rapidly trigger molecular events, which are irreversible and produce identical levels of DNA fragmentation at 24 h (33–41% and 51–58%, respectively), whether or not those drugs are maintained in the culture medium after 3 or 8 h (FIG. 20). It should be noted that no significant elevation of DNA cleavage is detectable in this assay after 3 and 8 h of drug exposure and that the increases of DNA fragmentation caused by TTs, DAU and CPT only appear after 12 h to reach a maximal level at 24 h (data not shown), suggesting that the irreversible events triggered by those drugs during the initial 3 h still require a substantial period of time, irrespective of the continual presence or absence of drugs, to fully induce DNA fragmentation. These results suggest that, like anticancer drugs known to induce DNA-strand breaks, TT quinones interact rapidly with cellular targets to induce long-lasting DNA-damaging effects, which develop and persist after drug removal.

HL

Figure 23:
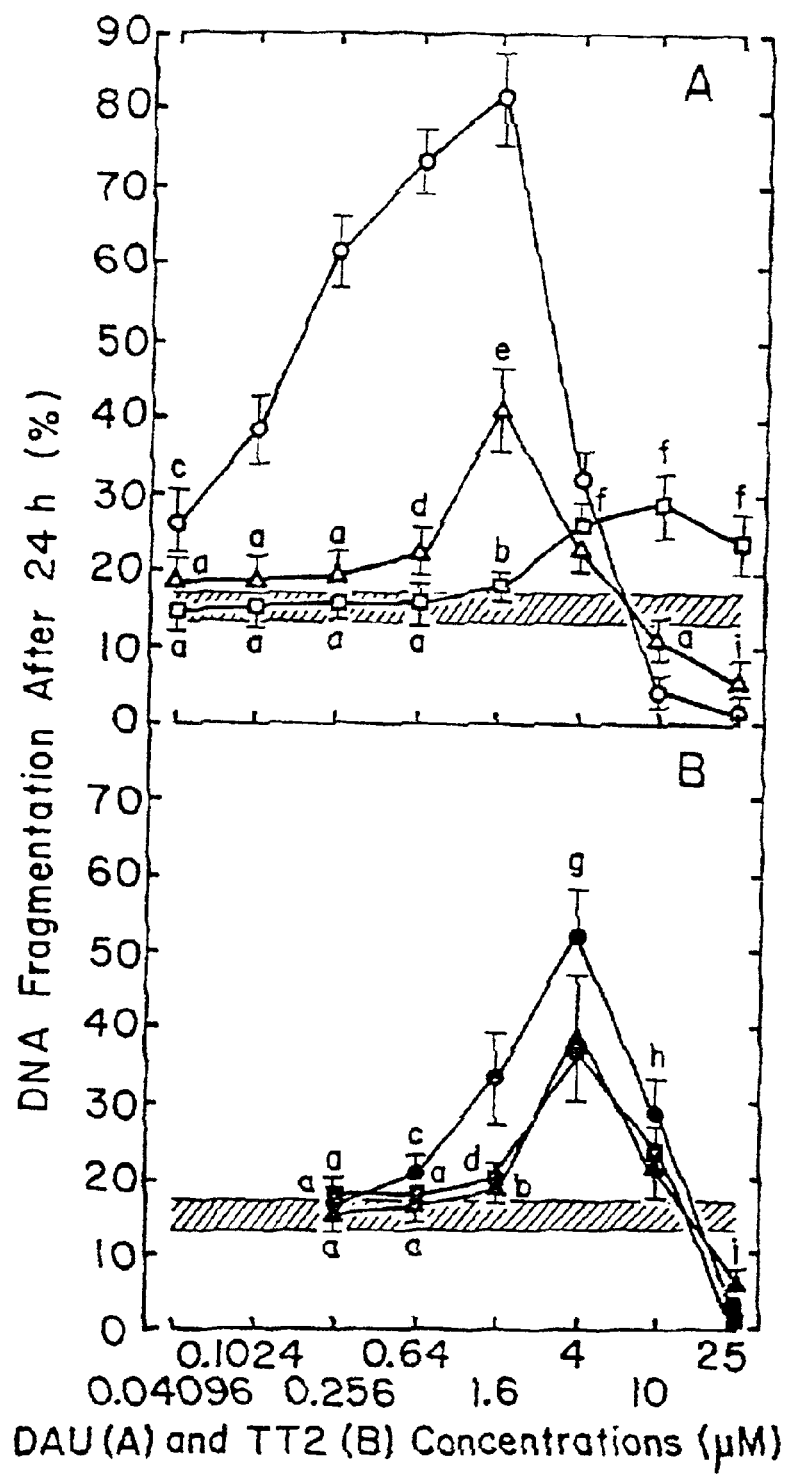
FIG. 23. Comparison of the concentration-dependent inductions of DNA cleavage by DAU (open symbols in A) and TT2 (closed symbols in B) at 24 h in HL-60-S (circles), HL-60-RV (squares) and HL-60-R8 (triangles) cells containing $^3$H-prelabeled DNA in vitro. Results are expressed as [cpm in supernatant/cpm in supernatant+pellet]×100 at 24 h. For untreated controls (14.7±1.7% DNA fragmentation, striped areas), the supernatant (DNA fragments) is 12,815±1,358 cpm and the pellet (intact DNA) is 74,406±9, 078 cpm. Bars: means±SD (n=3). $^a$Not different from control; $^b$P<0.05, $^c$P<0.025 and $^d$P<0.01, greater than control; $^e$P<0.005, smaller than the effect of 1.6 $\mu$M DAU in HL-60-S cells but not different from the effect of 0.1024 $\mu$M DAU in HL-60-S cells; $^f$not different from the effect of 0.04096 $\mu$M DAU in HL-60-S cells; $^g$P<0.05, greater than the effect of 4 $\mu$M TT2 in HL-60-RV cells but not different from the effect of 4 $\mu$M TT2 in HL-60-R8 cells; $^h$not different from the effect of 10 $\mu$M TT2 in HL-60-RV and HL-60-R8 cells; $^i$P<0.005, smaller than control.

Tumor cells containing $^3$H-thymidine prelabeled DNA were used to quantitatively determine whether TT2 would induce DNA fragmentation as effectively in WT as in MDR HL-60 cell lines that have become resistant to the DNA-damaging effects of DAU (FIG. 23). As reported before, the concentration-dependent induction of DNA cleavage caused by DAU is biphasic, peaking 67% above control level (15% DNA fragmentation) in HL-60-S cells treated for 24 h with 1.6 $\mu$M DAU but declining back to (18% above control at 4 $\mu$M), or even below (11 and 14% below control at 10 and 25 $\mu$M, respectively), control level at higher concentrations of DAU (FIG. 23A). Although TT2 is somewhat less potent than DAU, the concentration-dependent induction of DNA cleavage caused by this compound in HL-60-S cells is similarly biphasic, with a peak 37% above the control % of DNA fragmentation at 4 $\mu$M, followed by a decline toward (14% above control at 10 $\mu$M), or even below (11% below control at 25 $\mu$M), the control % of DNA fragmentation at higher concentrations (FIG. 23B). Interestingly, the ability of DAU to trigger maximal or submaximal DNA cleavage in WT cells is totally lost, drastically reduced and/or shifted toward higher concentrations in the MDR cell lines (FIG. 23A). For instance, the 0.04–0.64 $\mu$M concentrations of DAU producing submaximal stimulations of DNA cleavage (11–58% above the control level of 15%) in HL-60-S cells are almost totally unable to a do so in the HL-60-RV and HL-60-R8 cell lines. Moreover, the magnitude of the peak of maximal DNA cleavage caused by DAU in WT cells is not only reduced by 60 and 79% in HL-60-R8 and HL-60-RV cells, respectively, but it is also shifted from 1.6 to 10 $\mu$M in the latter MDR subline (FIG. 23A). As a result, the ability of 10–25 $\mu$M DAU to decrease DNA cleavage below control level in WT cells is totally or partially lost in the MDR cell lines. In contrast, the ability of TT2 to induce a peak of DNA cleavage at 4 $\mu$M and abolish the basal level of DNA cleavage at 25 $\mu$M in WT cells is pretty much unaltered in the two MDR sublines, although the magnitude of maximal stimulation observed in HL-60-S cells is reduced by 35 and 39% in the HL-60-R8 and HL60-RV cells, respectively (FIG. 23B).

The comparison studies show that the different magnitudes at which equimolar concentrations of various TT analogs inhibit tumor cell proliferation match very well the different cytotoxic activities of these compounds (FIG. 1). Moreover, the different levels of DNA fragmentation induced by the various TT analogs (FIG. 20) match exactly the ranking of these compounds for their cytostatic/cytotoxic effects (FIG. 1), suggesting that the ability of TT analogs to break DNA plays a significant role in their molecular mechanism of antitumor activity. In addition, the various TT analogs inhibit DNA synthesis in relation with their effectiveness against nucleoside transport (FIG. 11), suggesting that they prevent DNA assembly because they block the cellular uptake of DNA precursors. Because of their ability to interact with both membrane and nuclear targets to block nucleoside transport, inhibit nucleic acid and protein syntheses, cleave DNA, and reduce tumor cell growth and viability in the nM range in vitro, these TT analogs represent a novel synthetic class of bifunctional anticancer drugs valuable to develop new means of polychemotherapy.

The cytostatic and cytotoxic effects of each concentrations of TT2 increase with the time in culture (FIGS. 3 and 4), suggesting that the effectiveness of TT analogs as inhibitors of tumor cell proliferation and viability in vitro is a combination of drug concentration and duration of drug exposure. As a result, TT2 inhibits L1210 tumor cell growth at 2 and 4 days with IC$_{50}$ values of 300 and 150 nM, respectively, in relation with its ability to reduce L1210 tumor cell viability with IC$_{50}$ values of 250 nM at day 2 and 100 nM at day 4. The IC$_{50}$ required to reduce tumor cell viability at day 4 (100 nM) may be lower and perhaps more accurate than that observed for tumor cell growth inhibition at day 4 (150 nM) because the Coulter counter data include all viable and nonviable tumor cells that have previously accumulated and remain in the medium at day 4, irrespective of their present metabolic status and reproductive ability. Moreover, decreased tumor cell viability after several days of drug treatment may be a better predictor of anticancer activity than antiproliferation since growth delay may allow survivors to resume dividing and expand clonally once the drug is catabolized or eliminated and its effect is waning.

Overall, the new TT bisquinone TT2 is a potent antitumor agent, which is active in the nM range and is only 3.5–6 times less cytostatic/cytotoxic after 4 days than equimolar concentrations of the clinically proven anthracycline quinone antibiotic DAU, a very potent anticancer drug used as an arbitrary reference in our L1210 tumor cell studies in vitro (FIGS. 3 and 4). When $IC_{50}$ values are compared, TT2 also inhibits the syntheses of DNA, RNA and protein in L1210 cells after 2–3 h about 3–6 times less effectively than DAU (FIGS. 9, 16 and 17) and concentrations of TT2 about 6 times higher than those of DAU are also required to induce the same peak of DNA cleavage in L1210 cells after 24 h (FIG. 19). But in addition to mimicking all the antitumor effects of DAU studied, the data demonstrate that TT2 remarkably blocks the cellular transport of nucleosides, which DAU cannot do (FIG. 10), suggesting that these novel antitumor TT bisquinones may have a more versatile mechanism of action and be advantageous in polychemotherapy to potentiate the anticancer effects of antimetabolites and circumvent multidrug resistance (MDR). For both DAU and TT2 concentrations in the 25–150 nM range are sufficient to inhibit tumor cell growth/viability (FIGS. 3 and 4), whereas higher concentrations in the 0.8–10 $\mu$M range must be used to inhibit macromolecule syntheses (FIGS. 9, 16 and 17) and maximally induce DNA fragmentation (FIG. 19). But apparent discrepancies in potencies may be due in part to different experimental conditions and cellular responses to various periods of drug exposure: the rates of nucleic acid and protein syntheses over 30–60 min are inhibited in cells treated for only 2–3h with TT2 or DAU, whereas the level of DNA cleavage and the reduction of tumor cell growth/viability are the results of 1- and 4-day long drug treatments, respectively. It should be noted that no significant DNA fragmentation can be detected within the first 8 h of TT2 or DAU treatments and that concentrations of DAU and TT2 respectively greater than 0.25 and 1.6 $\mu$M must be used to induce substantial antiproliferative and cytotoxic effects after only 24 h of drug exposure (data not shown).

The fact that, within 24 h, TT1 and TT2 can produce as much internucleosomal DNA fragmentation in L1210 cells than the known Topo I and II inhibitors CPT and DAU (FIG. 19) suggests that the ability of TT quinones to produce DNA-strand breaks may play a major role in their mechanism of antitumor activity. Since the shapes of the concentration-response curves for the effects of TT1 and TT2 on DNA cleavage resemble the biphasic response to DAU, which has already been reported and discussed before, it is tempting to speculate that the mechanisms by which TT quinones and DAU induce DNA fragmentation share some similarity and that DNA cleavage is not always necessary for high concentrations of TT quinones and DAU to be cytotoxic. The Topo II-associated DNA lesions occuring in cells exposed to anthracycline quinone antibiotics may facilitate subsequent internucleosomal DNA fragmentation by endogenous nucleases and trigger apoptosis. Since apoptosis is an active and cell cycle phase specific process, which requires the expression of specific genes, the syntheses of new RNA and proteins and the activation of endonuclease enzymes, inhibitors of such mechanisms can prevent DNA fragmentation in anthracycline-treated cells. In spite of their increasing cytotoxicity, the highest concentrations of TT1, TT2 and DAU tested in our study might inhibit RNA and protein syntheses, reduce the level of Topo II targets, inactivate endonucleases and/or arrest cell cycle traverse to such degrees that they actually block the molecular mechanisms required for internucleosomal DNA fragmentation and apoptosis and produce the paradoxical biphasic curve of DNA cleavage shown in FIG. 19. Taken together, the irreversibilities of the inhibitions of nucleoside transport/DNA synthesis and of the induction of DNA fragmentation upon TT2 removal suggest that, because TT analogs may rapidly and tightly interact with various membrane and intracellular targets, their presence is soon no longer required in the medium to disrupt the structures/functions of nucleoside transporters, nucleic acids and proteins and to trigger long-lasting antitumor events, which persist after cessation of drug treatment.

Combining drugs, which target different molecules and achieve complementary or synergistic antitumor effects, is an important strategy in cancer chemotherapy. A TT quinone inhibiting nucleoside transport and inducing DNA cleavage might disrupt a wider spectrum of molecular targets in populations of unsynchronized tumor cells than another drug affecting a single of these events. Nucleoside transporters in mammalian plasma membranes function by equilibrative (facilitated diffusion) or $Na^+$-dependent (concentrative) mechanisms. All nucleosides are substrates for the $Na^+$-independent transporters but $Na^+$-dependent transporters generally accept purine rather than pyrimidine nucleosides as substrates. Dipyridamole (DPR), 6-(4-nitrobenzylmercapto)purine ribonucleoside (NBMPR) and dilazep are standard potent inhibitors of equilibrative nucleoside transport, whereas phloridzin specifically inhibits $Na^+$-dependent nucleoside transport. Like TT2, NBMPR and DPR also reduce $^3H$-thymidine incorporation into DNA. Nucleoside transport inhibitors block equally well the influx and efflux of nucleosides. L1210 cells possess 3 distinct nucleoside transporters: 2 equilibrative transporters sensitive (es) or insensitive (ei) to NBMPR and one $Na^+$-dependent transporter (cif), of low sensitivity to NBMPR and DPR.

For nucleotide synthesis, cells use purine and pyrimidine nucleosides generated either through de novo synthesis or through the utilization of salvage pathways. MDR is sometimes associated with increases in the number of nucleoside transporters and their rate of transport, resulting in the increased uptake of adenosine. By blocking the rescue effect of exogenous nucleosides, NBMPR, DPR and dilazep may potentiate or prolong the antitumor activity of antimetabolites which inhibit the de novo pathway for nucleoside synthesis. The clinical effectiveness of ADR and DAU is limited by their cumulative cardiotoxicity and ability to induce MDR. The multifactorial mechanisms of MDR to anthracycline quinone antibiotics may include altered expressions of P-glycoprotein (P-gp), Topo II and multidrug resistance-associated protein, increased DNA repair and glutathione-dependent detoxifying enzyme activities, and alterations in cell cycle progression and apoptotic pathways. DPR circumvents ADR resistance and its analog, BIBW 22, is a bifunctional modulator which reverses the MDR phenotype by interfering with both P-gp and nucleoside transport in MDR cells. As bifunctional inhibitors of nucleoside transport and inducers of DNA cleavage, TT quinones might be valuable in polychemotherapy to potentiate the antitumor activity of methotrexate and 5-fluorouracil and sensitize MDR tumor cells that have become unresponsive to the cytotoxicity of other conventional DNA-damaging anticancer agents.

TT2 is also cytostatic (IC$_{50}$: 300 nM) and cytotoxic (IC$_{50}$: 230 nM) to WT human HL-60-S leukemic cells in the present study. Another attractive feature of TT2 identified in the present study is the finding that this new quinone antitumor drug retains its effectiveness in two MDR HL-60-RV and HL-60-R8 sublines that have developed different mechanisms of resistance to DAU and, therefore, might not be recognized by either the P-gp or the MRP.

The magnitude at which TT2 inhibits HL-60-S, HL-60-RV and HL-60-R8 cell proliferation (IC$_{50}$ values: 260–300 nM) matches its ability to decrease cell viability (IC$_{50}$ values: 230–350 nM) in the same WT and MDR tumor cell lines at day 4. Moreover, the cytostatic and cytotoxic effects of each concentrations of TT2 obviously increase with the time in culture at days 2 and 4, suggesting that the effectiveness of TT2 as an inhibitor of tumor cell proliferation and viability is a combination of drug concentration and duration of drug exposure. Decreased WT and MDR tumor cell viability after TT2 treatment in vitro may be a reliable predictor of anticancer activity in vivo. However, it should be noted that DAU is about 3.5–6 times more cytostatic/cytotoxic than TT2 in L1210 cells, even though TT2 appears more potent in the L1210 than in the HL-60-S cells. Hence, TT2 inhibits tumor cell growth, viability and DNA synthesis respectively 33, 15 and 9 times less effectively than DAU in the HL-60-S leukemic system (FIGS. 5–8, 10). Moreover, concentrations of TT2 at least 2.5 times greater than those of DAU are required to induce more than 50% of DNA cleavage in HL-60-S cells at 24 h (FIG. 23). Nevertheless, the magnitudes of the inhibitory and stimulatory effects trigged by DAU and somewhat higher concentrations of TT2 are nearly identical in HL-60-S cells. But the critical finding is that the ability of TT2 to inhibit tumor cell growth, viability and DNA synthesis in HL-60-S cells persists unaltered in the HL-60-RV and HL-60-R8 cell lines (RFs: 0.9–1.5) while DAU becomes dramatically less effective against DNA synthesis (RFs: 8.1–11.9), cell proliferation (RFs: 22.9–35.7) and cell viability (RFs: 23.8–31.3) in these MDR HL-60 sublines than in their parental WT counterparts. Finally, TT2 which, in contrast to DAU, has the unique ability to rapidly block the cellular transport of both purine and pyrimidine nucleosides in L1210 (13) and HL-60-S cells, retains such additional advantage in the MDR HL-60 sublines (FIG. 15). These observations substantiate the hypothesis that, because of its bifunctional mechanism of action, TT2 is a quinone antitumor drug which may be more versatile than DAU and able to circumvent MDR.

SYNTHESIS EXAMPLES

Synthesis of TT2, TT13 and Their Analogs:

Although the preparation of 1,4-dimethoxyanthracene (1) has been reported (Criswell, et al., J. Org. Chem. 1974, 39, 770–774) by using methylation of quinizarin (3) followed by sequential reduction of the diketo function with sodium borohydride in diglyme, the difficulty in the reduction steps prompted us to investigate an easier method in the preparation of 1. Reduction of 3 with sodium borohydride in MeOH followed by quenching with HCl gave a 95% yield of 1,4-anthraquinone (4) (Scheme 2). Reduction of the quinone moiety of 4 with aqueous sodium hydrosulfite in 1,4-dioxane provided 1,4-dihydroxyanthracene (5). Methylation of 5 with sodium hydride in DMF at room temperature gave excellent yield of 1.

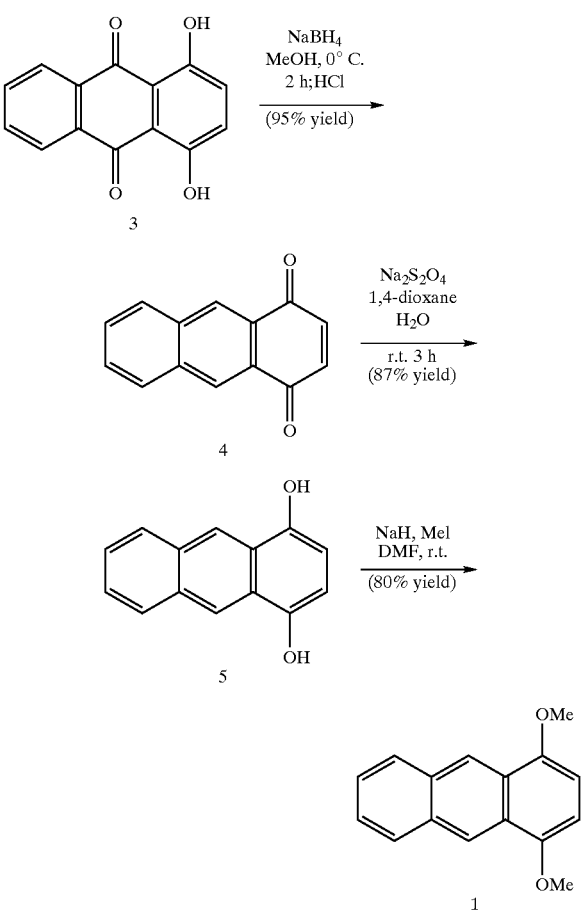

In Situ Oxidation Followed by [4+2]-Cycloaddition:

A short syntheses of TT2, TT3, and TT5 were discovered. Without the use of quinones as the dienophiles in the Diels-Alder reaction, such as 2-methoxyquinone (8), a one-pot oxidation followed by [4+2]cycloaddition of 2-methoxyhydroquinone (6) with anthracene 1 was found (Scheme 3). Hence, treatment of 2 equiv of 6, 1 equiv of anthracene 1, 2 equiv of silver oxide, and 0.2 equiv of zinc iodide in refluxing toluene for 24 h gave diketone 7 (51% yield; based on reacted 1), hydroquinone TT3 (26% yield; based on reacted 1), quinone TT5 (13% yield; based on reacted 1) and 55% recovery of 1.

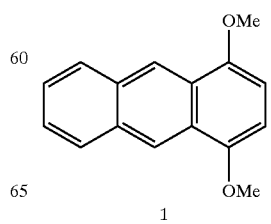

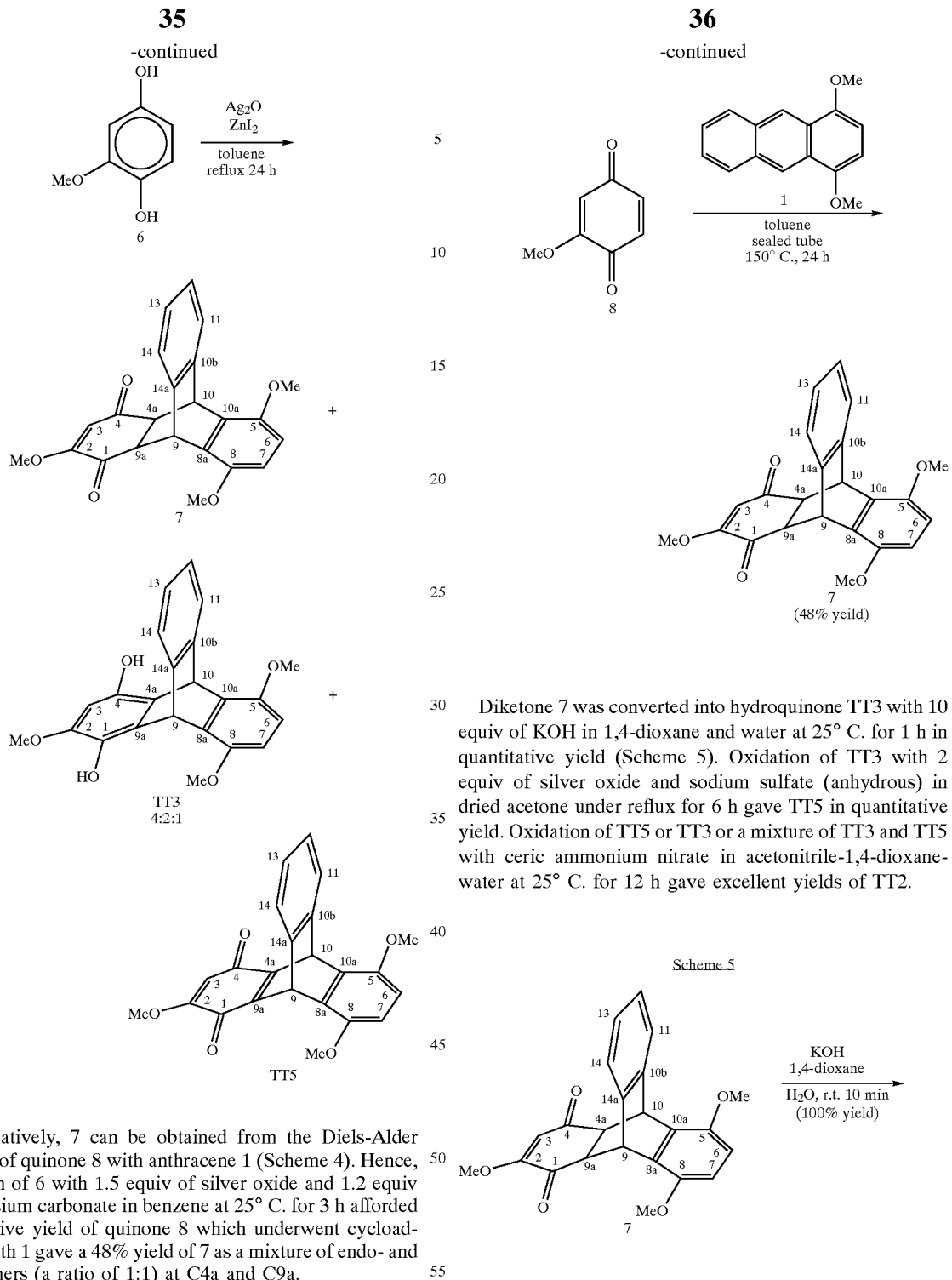

Alternatively, 7 can be obtained from the Diels-Alder reaction of quinone 8 with anthracene 1 (Scheme 4). Hence, oxidation of 6 with 1.5 equiv of silver oxide and 1.2 equiv of potassium carbonate in benzene at 25° C. for 3 h afforded quantitative yield of quinone 8 which underwent cycloaddition with 1 gave a 48% yield of 7 as a mixture of endo- and exo-isomers (a ratio of 1:1) at C4a and C9a.

Diketone 7 was converted into hydroquinone TT3 with 10 equiv of KOH in 1,4-dioxane and water at 25° C. for 1 h in quantitative yield (Scheme 5). Oxidation of TT3 with 2 equiv of silver oxide and sodium sulfate (anhydrous) in dried acetone under reflux for 6 h gave TT5 in quantitative yield. Oxidation of TT5 or TT3 or a mixture of TT3 and TT5 with ceric ammonium nitrate in acetonitrile-1,4-dioxane-water at 25° C. for 12 h gave excellent yields of TT2.

Scheme 4

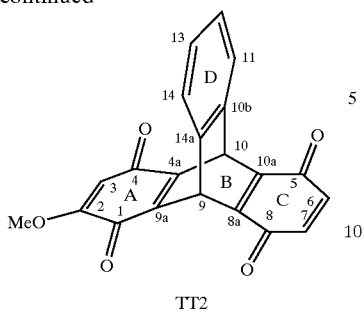

TT2

Selective Bromination of 2-Methoxy Triptycene Quinone:

A new bromination reaction was found (Scheme 6). Hence, when TT5 was treated with N-bromosuccinimide (NBS) in DMF at 40° C. for 12 h, a quantitative yield of the C-2 brominated product 9 was obtained. Without purification, compound 9 was directly subjected to the ceric ammonium nitrate oxidation and a 59% yield of TT13 was achieved.

2-chlorohydroquinone (11), under similar reaction conditions, reacted with 1,4-dimethoxyanthracene (1) in the presence of silver oxide and zinc iodide under refluxing toluene to give a 73% yield of the chloro derivative 12 (Scheme 7).

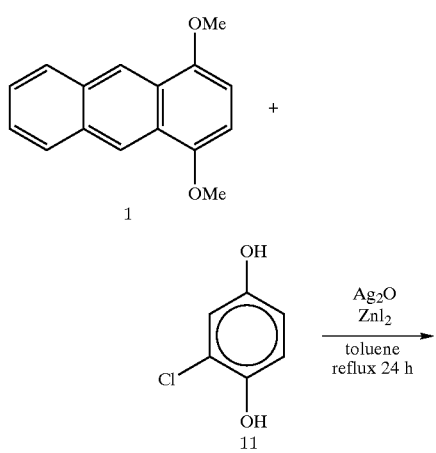

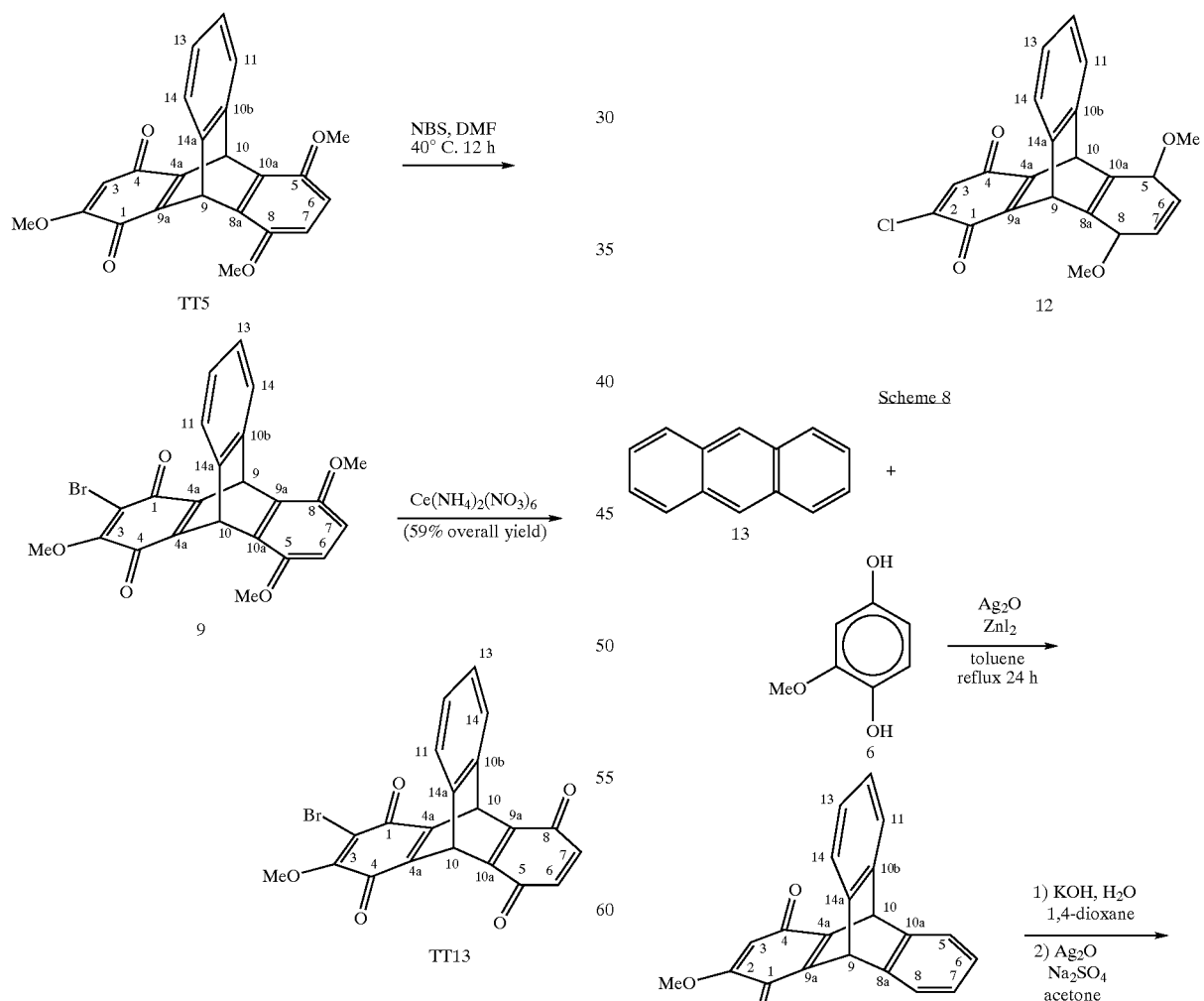

Syntheses of 2-Chloro-4a,9,9a,10-tetrahydro-9,10-[1',2'] benzenoanthracene-1,4-dione (10), TT8, TT9 and TT7:

The in-situ oxidation and cyclization reaction is applicable to other hydroquinone substrates. For instance,

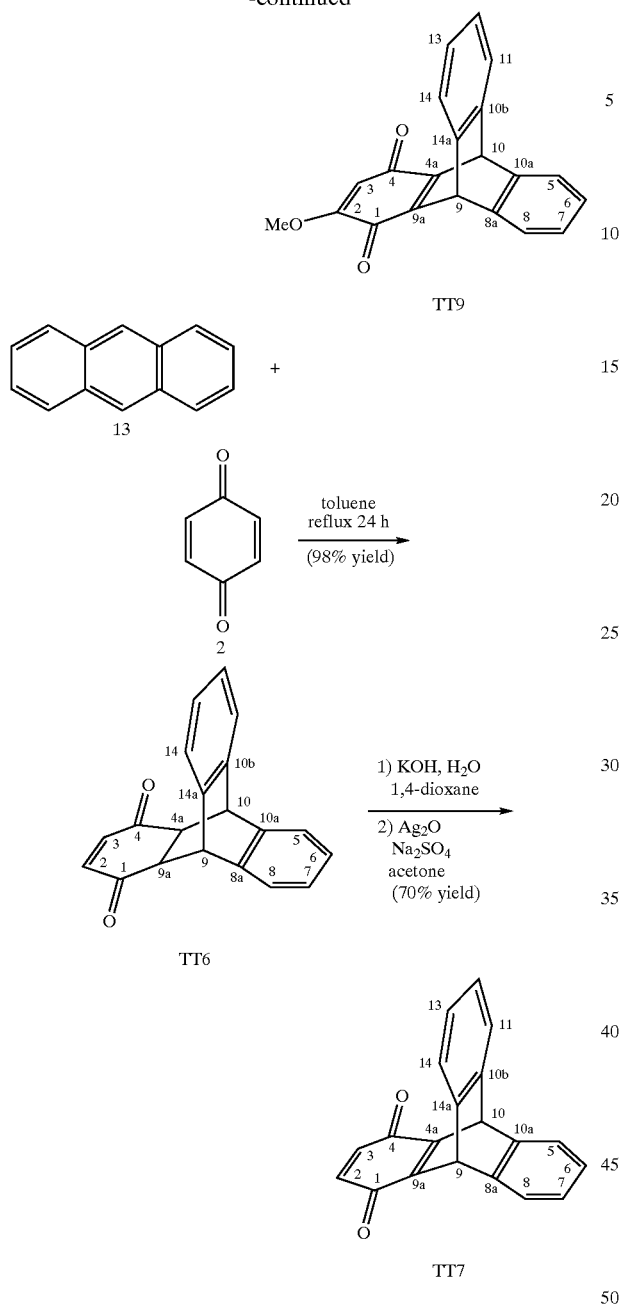

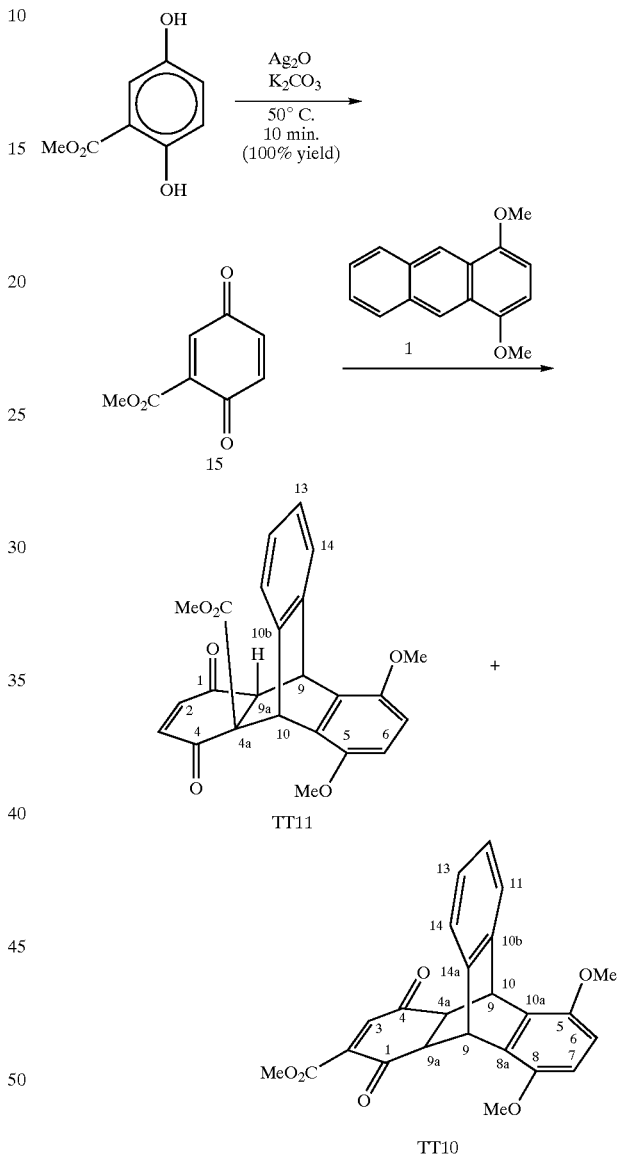

with 2 equiv of silver oxide and 1.2 equiv of potassium carbonate in benzene at 50° C. for 10 min under dark gave a quantitative yield of the corresponding quinone 16 (Scheme 9). Diels-Alder reaction of 15 and anthracene 1 at 70° C. for 14 h and then under reflux for 5 h gave 58% yield of TT11 (as a mixture of endo- and exo-isomers) and 37% yield of TT10.

Similarly, treatment of 2-methoxyhydroquinone (6) with anthracene (13) and silver oxide and zinc iodide gave a 56% yield of the 2-methoxy derivative TT8 (Scheme 8). Basic isomerization of ketone 14 with 3 equiv of KOH in 1,4-dioxane and water at 25° C. for 2 h followed by oxidation with silver oxide and sodium sulfate (anhydrous) in dried acetone at 25° C. for 3 h to give an 80% yield of quinone TT9. Quinone TT7 was prepared by the Diels-Alder reaction of benzoquinone (2) with anthracene 13 to give adduct TT6 (98% yield) which under similar isomerization and oxidation as those for the conversion of TT8 into TT9 gave TT7 (70% yield for the last two steps).

Syntheses of TT10 and TT11:

Contrary to the above results, when methyl gentisate (14) was used in the in-situ oxidation followed by [4+2] cycloaddition reaction, only small amount of a mixture of products was isolated. Compound 14 was then oxidized first Syntheses of TT4 and TT12:

The triptycene bis-quinones such as TT1 could be treated with dienes to produce various substituted triptycene analogs such as TT4 and TT12 (Scheme 10). Hence, treatment of TT1 with 2.2 equiv of dimethyl butadiene-2,3-dicarboxylate (16) (Hamon, et al., J. Chem. Soc. Chem. Commun. 1981, 873–4) in toluene under reflux for 20 h gave a 54% yield of TT4 and 14% yield of monoadduct 17. The stereochemistry of TT4 was firmly established by a single-crystal X-ray analysis. Reduction of TT4 with 10 equiv each of sodium borohydride and cerium trichloride heptahydrate in MeOH at room temperature for 12 h afforded an 89% yield of TT12. The $^1$H and $^{13}$C NMR spectrum of TT12 indicated a single stereoisomer. It is anticipated that the hydride (sodium borohydride) should attack the carbonyl group from the exo face (b-face) and the stereochemistry is therefore assumed.

Syntheses of TT14, TT15, and TT16:

Bromomethoxyquinone TT13 can be converted into methylaminoquinone TT14 in 25% yield along with a 29% yield of TT15 by the treatment with methylamine in THF at room temperature for 20 min (Scheme 11). This reaction is unusual in that the nucleophile, methylamine, displaces the methoxy group of TT13 instead of the bromine. Again, unexpectedly, when TT13 was treated with dimethylamine in THF at 0° C., TT16 was isolated as the only identifiable product (Scheme 12). The regiochemistry of the dimethylamino group of TT16 is tentatively assigned.

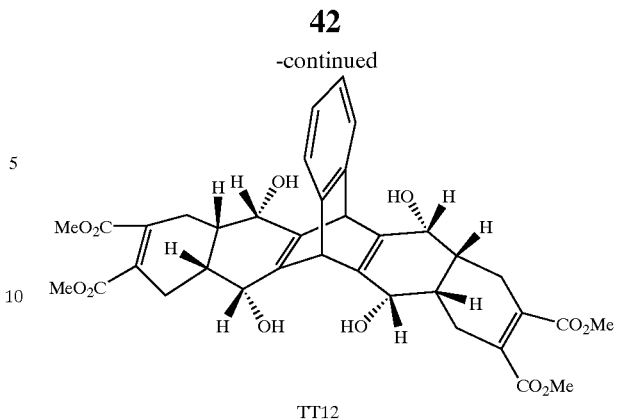

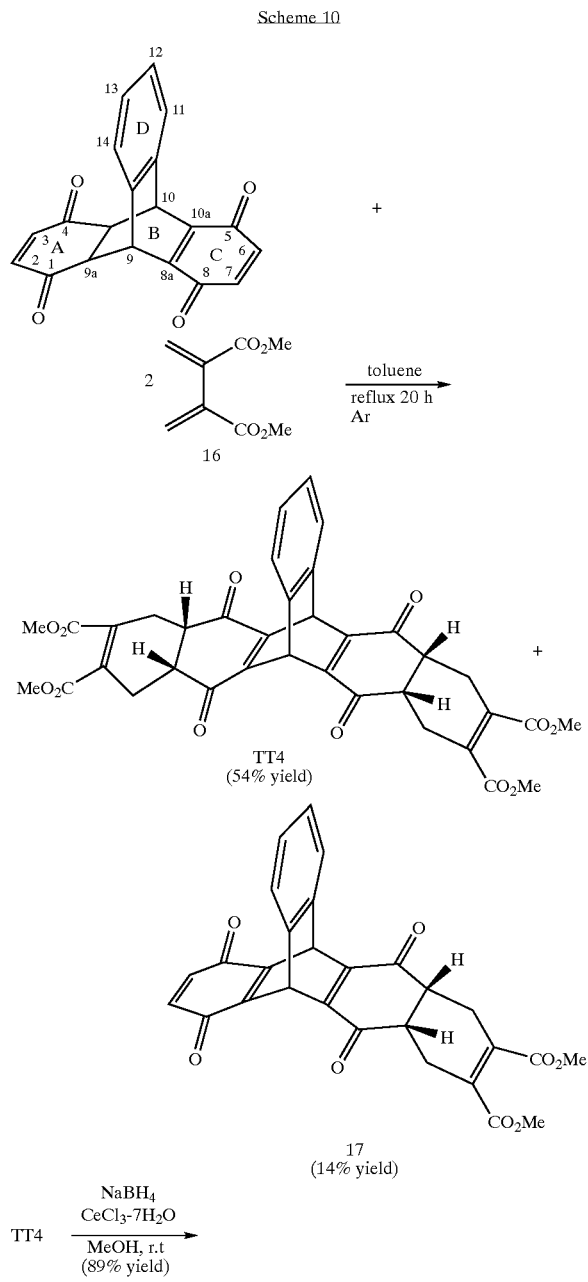

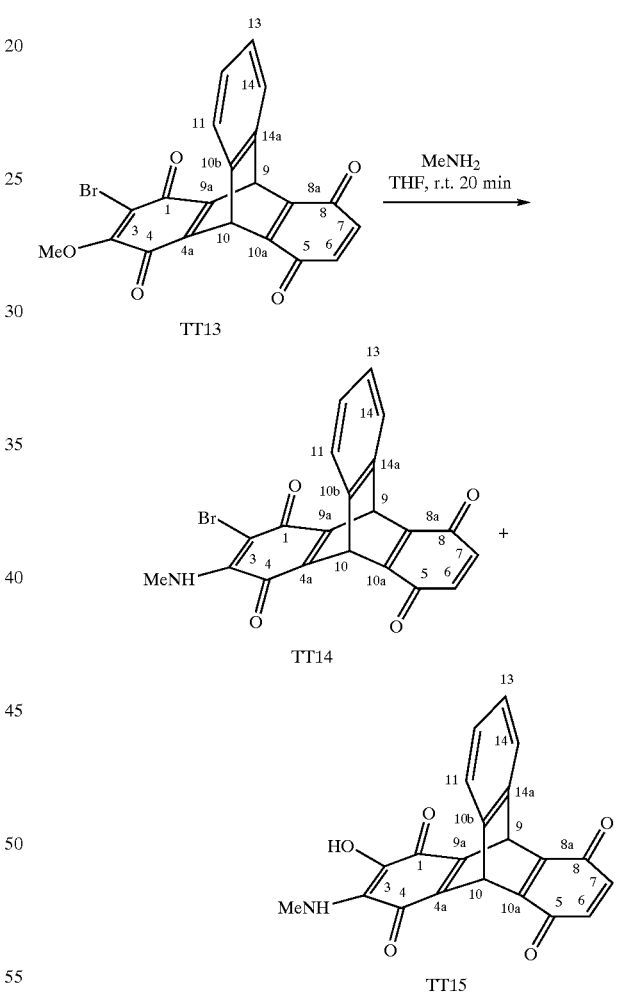

Similar to the addition reaction of methylamine with TT13, other primary amines, such as ethyl b-alanine and L-lysine also add to TT13 to provide the corresponding amino acid adducts TT17~TT20 (Scheme 13). Hence, treatment of TT13 with ethyl b-alanine (derived from ethyl b-alanine hydrochloride with 1 equiv of sodium hydride in THF) in THF and DMF at 25° C. to give a mixture of TT17 and TT18 (based on the proton NMR spectrum of the crude product). Column chromatographic separation on silica gel gave TT18 in 69% yield. The ethyl ester function of TT18 can be removed by treatment with sodium iodide in DMF with heat to give amino acid TT21 which is water soluble.

Scheme 12
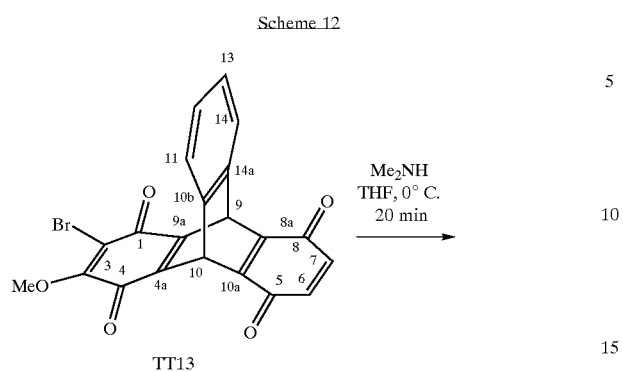
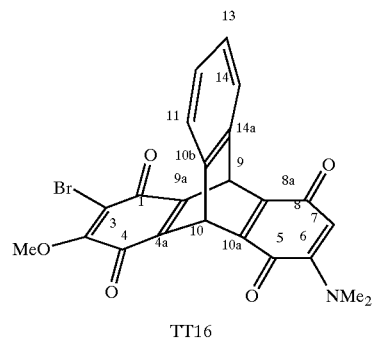
Scheme 13
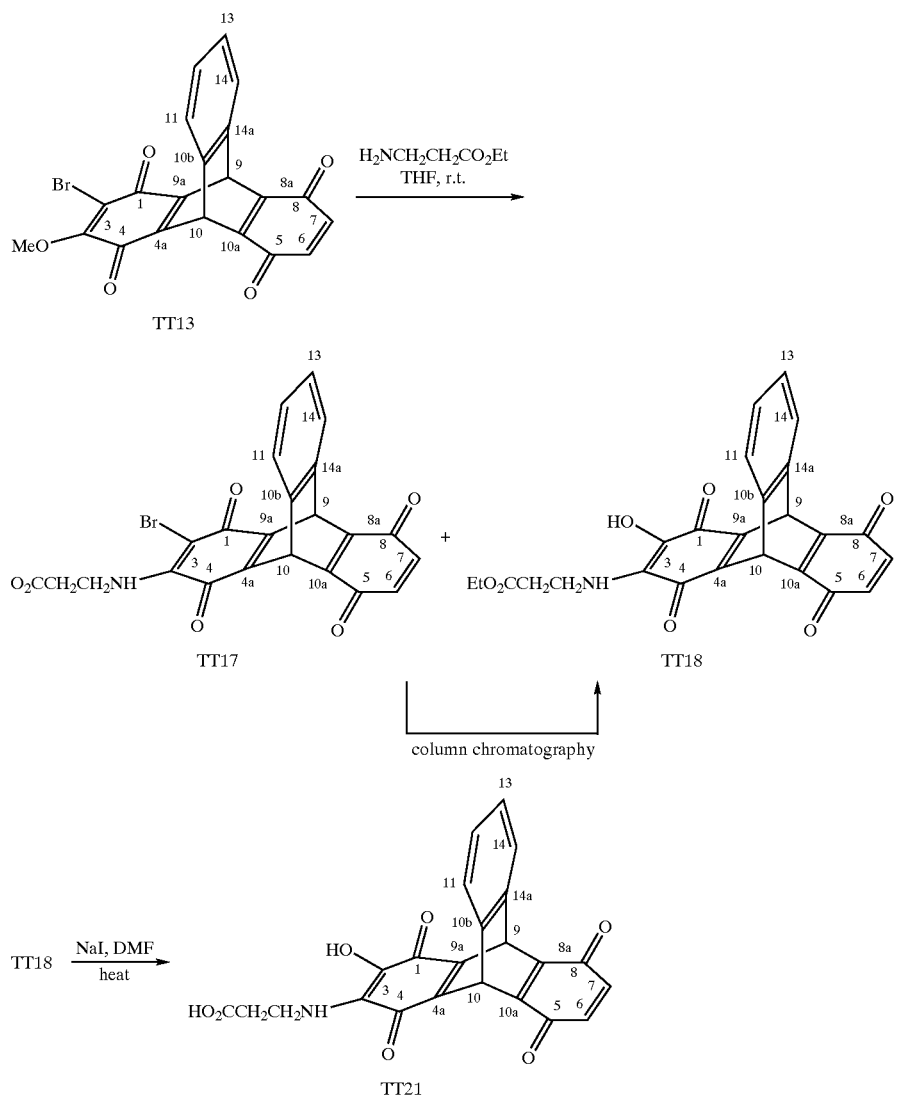

Under similar reaction conditions, TT13 was treated with L-lysine (derived from L-lysine monohydrochloride and 1 equiv of NaH in THF) in THF and DMF to give adducts TT19 and TT20 which were purified on HPLC to give TT20 (TT19 most likely hydrolyzes on the column to give TT20) .Hence, a number of water-soluble drugs can be obtained by adding amino acids or amino sugars onto TT13, by reactions that are known in the art.

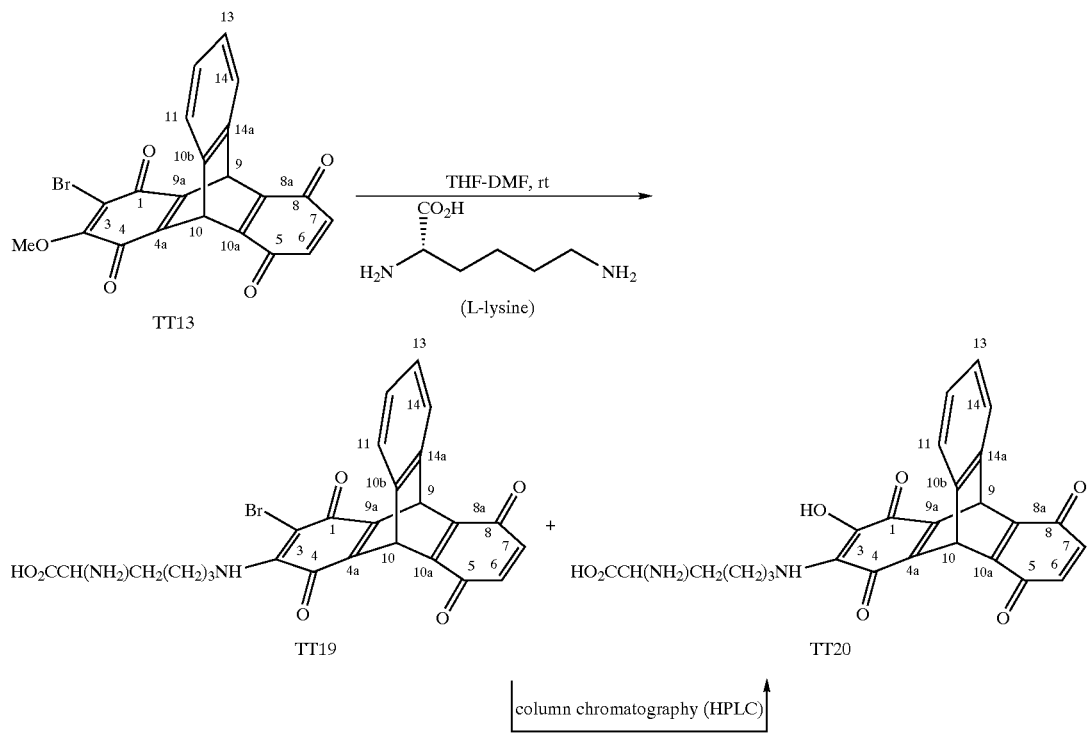

Preparation of 1,4-anthracenedione (4):

To a dried 100 mL-round-bottom flask equipped with stirring bar and serum cap, was added 1 g (MW 240.21; 0.0042 mol) of quinizarin (3). The compound was dried under vacuum, and then maintained under argon. Methanol (distilled over Mg), 20 mL, was added via syringe. The solution was stirred to dissolve the quinizarin and then cooled over an ice-water bath equipped with a thermometer. To it, 0.638 g (MW 38; 0.0168 mol) of sodium borohydride was added. The resulting mixture was stirred at 0° C. for 1 hour. The progress of the reaction was monitored by TLC (using hexanes: ether 1:1 as the eluant). The reaction was quenched by adding carefully 11 mL of 6 N HCl dropwise at 0° C. over a period of 10 minutes. Orange solids precipitate. The solids were collected by filtration over a fritted filter funnel, and washed several times with distilled water to remove the acid. The solid was then dried under vacuum and recrystallize from acetone-ether to give 0.83 g (95% yield) of yellow crystals, mp 204–206° C.

$^1$H NMR (CDCl$_3$) d ppm: 7.1 (s, 2H, C 2,3 Hs), 7.7 (dd, J=6.4, 3.2 Hz, 2H, C 6,7 Hs), 8.1 (dd, J=6.4, 3.2 Hz, 2H, C 5,8 Hs), 8.6 (s, 2H, C 9,10 Hs); $^{13}$C NMR (CDCl$_3$) d ppm: 184.68 (s, C=O), 140.06 (d), 134.83 (s), 130.22 (d), 129.59 (d), 128.87 (d), 128.37 (s).

Preparation of 1,4-Dihydroxyanthracene (5):

To a 250 ml-round-bottom flask, was added 2 g (MW 208; 0.0096 mol) of 1,4-anthracenedione (4). To it a solution of 6.6816 g (MW 174; 0.0384 mol) of sodium hydrosulfite in 50 mL of distilled water and 50 mL of 1,4-dioxane were added. The resulting mixture was stirred at room temperature for 2–3 hours. The reaction progress is checked with TLC (using CH$_2$Cl$_2$:hexanes:ether 1:1:0.2 as the eluant). The mixture was transferred to a 500-mL beaker slowly, cooled over an ice-water bath, and added 100 mL of distilled water. Dark green solids precipitated. The beaker was covered with aluminum foil, and placed in the refrigerator for 1 h. The solid was filtered through a glass fritted funnel and the product was washed with 30 mL of distilled water twice. The solid product was dried under vacuum to give 1.754 g (87% yield), mp 167–169° C.; $^1$H NMR (CDCl$_3$ contains a small amount of p-dioxane) d 8.7 (m, 2H, C 9,10 Hs), 8.05 (m, 2H, C 5,8 Hs), 7.5 (s, 2H, C 6,7 Hs), 6.6 (s, 2H, C 2,3 Hs). The diol is insoluble in chloroform but soluble in DMSO and DMF.

Preparation of 1,4-Dimethoxyanthracene (1):

To a dried flask, 0.549 g (0.011 mol; 50% oil) of sodium hydride was added. The material was dried under vacuum and flame and maintained under argon. To it 3 mL of distilled ether was added, stirred, and the ether layer containing the oil was removed and discarded. To the sodium hydride flask, 1 g (0.0048 mol) of diol 5 was added and the mixture was dried under vacuum and flame and maintained under argon. DMF (10 mL) was added via syringe and the solution was stirred at room temperature for 1.5 h. TLC of a sample from the reaction solution indicated no starting material. The solution was diluted with 20 mL of water and 6 N HCl until pH=2. The mixture was extracted with ethyl acetate three time. The combined extract was washed with water twice and brine, dried (MgSO$_4$), concentrated to give 1.07 g (94% yield) fo the crude product (proton NMR spectrum indicated >90% pure). The product was recrystallized from ether:hexane to give 0.89 g (78% yield) of black solids, mp 255–258° C. $^1$H NMR (CDCl$_3$) d 8.70 (s, 2H, C9,10H), 7,97 (dd, J=6.1, 3.6 Hz, 2H, C5,8H), 7.40 (dd, J=6.6, 3.2 Hz, 2H, C6,7H ), 6.55 (s, 2H, C2,3H), 3.97 (s, 6H, OCH$_3$); $^{13}$CNMR (CDCl$_3$) d 149.47 (s, C8a,10a), 131.45 (s, C4a,9a), 128.51 (d, C9,10), 125.47 (d, C5,8), 120.73 (d, C6,7), 100.88 (d, C2,3), 55.61 (s, OCH$_3$); M.S. (FAB) m/z=238 (M), 239 (MH$^+$).

2,5,8-Trimethoxy-4a,9,9a,10-tetrahydro-9,10-[1',2']benzenoanthracene-1,4-dione (7), 1,4-Dihydroxy-2,5,8-triethoxy-9,10-dihydro-9,10-[1',2']benzenoanthracene (TT3), and 2,5,8-Trimethoxy-9,10-dihydro-9,10-[1',2']benzenoanthracene-1,4-dione (TT5).

A mixture of 0.2 g (0.84 mmol) of 1,4-dimethoxyanthracene (1), 0.235 g (1.68 mmol) of methoxyhydroquinone (6), 0.39 g (1.68 mmol) of silver oxide and 54 mg (0.17 mmol) of zinc iodide in 20 mL of toluene (distilled over CaH$_2$) was heated to reflux under argon for 24 h. The reaction mixture was cooled to room temperature, concentrated and directly subjected to a silica gel column. After elution with a gradient mixture of hexane and ether and then with ethyl acetate and methanol, 0.11 g (55% recovery) of compound 1, 0.11 g of methoxy-1,4-quinone, 73 mg (51% yield) of 7, 37 mg (26% yield) of TT3, and 18 mg (13% yield) of TT5 were isolated.

Compound 7: $^1$H NMR(CDCl$_3$) d 7.24–7.18 (m, 2H, C12,13 Hs), 7.08–7.04 (m, 2H, C11,14 Hs), 6.65 (s, 2H, C6,7 Hs), 5.61 (s, 1H), 5.33 (s, 1H), 3.82 (s, 6H, OMe), 3.48 (s, 3H, OMe), 3.10 (q, J=9 Hz, 2H, C4a,9a Hs). Compound TT3: $^1$H NMR (CDCl$_3$) d 7.43 (dd, J=5.5, 3 Hz, 1H), 7.38 (dd, J=5.5, 3 Hz, 1H), 6.96 (dd, J=5.5, 3 Hz, 2H, C11,14 Hs), 6.51 (s, 2H, C6,7 Hs), 6.29 (s, 1H, C3H), 6.09 (s, 1 H), 5.98 (s, 1H), 5.3 (s, 1H, OH), 4.96 (bs, 1H, OH), 3.81 (s, 3H, OMe), 3.805 (s, 3H, OMe), 3.66 (s, 3H, OMe). Compound TT5: $^1$H NMR (CDCl$_3$) d 7.43 (dd, J=5.5, 3 Hz, 2H, C12,13 Hs), 7.0 (dd, J=5.5, 3 Hz, 2H, C11,14 Hs), 6.52 (s, 2H, C6,7 Hs), 6.25 (s, 1H), 6.23 (s, 1H), 5.71 (s, 1H, C3H), 3.79 (s, 6H, OMe), 3.72 (s, 3H, OMe).

Isomerization of 7 to TT3:

To a solution of 0.77 g (2 mmol) of 7 in 30 mL of p-dioxane and 30 mL of water was added 1.12 g (20 mmol) of KOH. The solution was stirred at room temperature for 1 h, acidified with 1 M HCl, and extracted with methylene chloride three times. The combined extract was washed with brine, dried (MgSO$_4$), concentrated to give 0.77 g (100% yield) of TT3.

Oxidation of TT3 to TT5:

To a mixture of 0.77 g (2 mmol) of TT3 and 0.6 g of sodium sulfate (anhydrous) in 15 mL of dried acetone under argon at room temperature was added 0.557 g (4 mmol) of silver oxide. The mixture was heated under reflux for 6 h, cooled to room temperature, diluted with methylene chloride, and filtered through Celite. The filtrate was concentrated to give 0.77 g (100% yield) of TT5. $^1$H NMR spectrum indicates it to be the desired product and was used in the next step without purification.

2-Methoxy-9,10-dihydro-9,10-[1',2']benzenoanthracene-1,4,5,8-tetraone (TT2):

To a solution of 0.77 g (0.002 mol) of TT5 in 16 mL of acetonitrile, 26 mL of p-dioxane and 10 mL of water was added 2 g (3.6 mmol) of ceric ammonium nitrate at room temperature. The solution was stirred for 12 h, diluted with methylene chloride, and washed with water. The organic layer was dried (MgSO$_4$), concentrated to give the crude product. Recrystallization from ether gave 0.68 g (99% yield) of TT2. $^1$H NMR (CDCl$_3$) d 7.48 (dd, J=5.5, 3 Hz, 2H, C12,13 Hs), 7.07 (dd, J=5.5, 3 Hz, 2H, C11,14 Hs), 6.65 (s, 2H, C6,7 Hs), 6.2 (s, 1H), 6.18 (s, 1H), 5.78 (s, 1H, C3H), 3.78 (s, 3H, OMe). MS, CI, m/z 345 (M+1).

2-Bromo-3,5,8-trimethoxy-9,10-dihydro-9,10-[1',2']benzenoanthracene-1,4-dione (9):

To a solution of 90 mg (0.24 mmol) of TT5 in 5 mL of DMF under argon at room temperature was added 52 mg (0.3 mmol) of N-bromosuccinimide (NBS). The solution was stirred at 40° C. for 12 h. A sample was withdrawn and checked by TLC to show that no starting material presented. The solution was diluted with ether and washed with twice with water and once with brine, dried (MgSO$_4$), concentrated to give 109 mg (quantitative yield) of the crude product. This material was used in next step without purification. $^1$H NMR (CDCl$_3$) d 7.44 (dd, J=5.5, 3 Hz, 2H, C12,13 Hs), 7.01 (dd, J=5.5, 3 Hz, 2H, C11,14 Hs), 6.54 (s, 2H, C6,7 Hs), 6.29 (s, 1H), 6.22 (s, 1H), 4.14 (s, 3H, C3 OMe), 3.81 (s, 3H, OMe), 3.79 (s, 3H, OMe).

2-Bromo-3-methoxy-9,10-dihydro-9,10-[1',2']benzenoanthracene-1,4,5,8-tetraone (TT13):

To the above product, compound 9, in a solution of 5 mL of acetonitrile, 6 mL of p-dioxane, and 2 mL of water was added 0.66 g (1.2 mmol) of ceric ammonium nitrate. The solution was stirred at room temperature for 6 h, diluted with ether. The mixture was transferred into a separatory funnel, washed with water and brine, dried (MgSO$_4$), concentrated, and column the (59% yield) of pure TT13; mp 207–210° C. $^1$H NMR (CDCl$_3$) d 7.48 (dd, J=5.5, 3 Hz, 2H, C12,13 Hs), 7.09 (dd, J=5.5, 3 Hz, 2H, C11,14 Hs), 6.66(s, 2H, C6,7 Hs), 6.23 (s, 1H), 6.16 (s, 1H), 4.17 (s, 3H, C3 OMe). $^{13}$C NMR (CDCl$_3$) d 182.2 (s, C1), 182.0 (s, C4), 176.2 (s, C=O), 175.5 (s, C=O), 156.2, 151.6, 151.4, 150.2, 141.8, 135.5, 135.4, 126.2, 126.1, 126.07, 126.0, 125.6, 125.4, 117.2, 61.7 (q, OMe), 43.0 (d), 42.1 (d). MS EI, m/z 424 & 422 (1:1, M+), 344 (M−Br), 300, 287, 232, 152, 126.

2-Chloro-5,8-dimethoxy-4a,9,9a,10-tetrahydro-9,10-[1',2']benzenoanthracene-1,4-dione (12):

A solution of 0.1 g (0.42 mmol) of 1,4-dimethoxyanthracene (1), 0.121 g (0.84 mmol) of chlorohydroquinone (11), 0.195 g (0.84 mmol) of silver oxide, and 27 mg (0.084 mmol) of zinc iodide in 10 mL of toluene was heated under reflux for 10 h. The mixture was concentrated on a rotary evaporator and the residue was subjected to a silica gel column. After elution of a gradient mixture of hexane and ether, 64 mg (73% yield based on reacted 1) of 12 and 45 mg (45% recovery) of 1. Compound 12: $^1$H NMR (CDCl$_3$) d 7.42 (m, 2H, C12,13 Hs), 7.18 (dd, J=5.5, 3 Hz, 2H, C11,14 Hs), 6.64 (d, J=6 Hz, 1H), 6.61 (d, J=6 Hz, 1H), 6.55 (s, 1H, C3H), 5.31 (d, J=3 Hz, 1H), 5.28 (d, J=3 Hz, 1H), 3.76 (s, 3H, OMe), 3.75 (d, 3H, OMe), 3.17 (qd, J=9, 2.6 Hz, 2H, C4a,9a Hs).

2-Methoxy4a,9,9a,10-tetrahydro-9,10-[1',2']benzenoanthracene-1,4-dione (TT8):

A mixture of 0.5 g (2.8 mmol) of anthracene (13), 0.787 g (5.6 mmol) of methoxyhydroquinone (6), 1.298 g (5.6 mmol) of silver oxide and 0.179 g (0.56 mmol) of zinc iodide in 10 mL of toluene was heated under reflux for 24 h under argon. The mixture was diluted with methylene chloride and water, filtered through Celite, and the filtrate was transferred into a separatory funnel. After washing with brine, the organic layer was dried (MgSO$_4$), concentrated to give dark green solids; NMR spectrum of this material indicated desired product. The solid was recrystallized from ether to give 0.50 g (56% yield) of TT8 as light green white solids, mp 182–184° C.; $^1$H NMR (CDCl$_3$) d 7.4 (m, 2H), 7.2 (m, 4H), 7.1 (m, 2H), 5.64 (s, C3H), 4.89 (s, 2H, C9,10 Hs), 3.51 (s, 3H, MeO), 3.17 (qd, J=9.5, 3 Hz, 2H, C4a,9a Hs); $^{13}$C NMR (CDCl$_3$) d 193.25 (s, C=O), 162.84, 161.76, 141.63, 139.84, 139.29, 126.68, 126.66, 126.57, 126.51, 124.91, 124.61, 123.89, 123.82, 113.57, 56.12 (OMe), 49.56, 49.15, 48.87, 48.84.

2-Methoxy-9,10-dihydro-9,10-[1',2']benzenoanthracene-1,4-dione (TT9):

To a solution of 0.2 g (0.63 mmol) of ketone TT8 in 5 mL of p-dioxane and 1 mL of water was added 0.106 g (1.9 mmol) of KOH. The solution was stirred at room temperature for 2 h, neutralized with 1 N HCl, and extracted with methylene chloride twice. The combined extract was washed with brine, dried (MgSO$_4$), concentrated to give the crude product diol. This compound was used in the following oxidation reaction without purification. A solution of the above diol, 0.4 g (2.8 mmol) of sodium sulfate (anhydrous), and 0.4 (1.7 mmol) of silver oxide in 12 mL of acetone was stirred at room temperature for 3 h. The mixture was diluted with methylene chloride, filtered through Celite, washed with brine, dried (MgSO$_4$), concentrated, and column chromatographed on silica gel using a gradient mixture of hexane and ether as eluant to give 0.16 g (80% yield) of TT9; mp 195–197° C.; $^1$H NMR (CDCl$_3$) d 7.43 (m, 2H, C12,13 Hs), 7.03 (dd, J=5, 3 Hz, 2H, C11,14 Hs), 5.83 (s, 1H), 5.80 (s, 1H), 5.74 (s, 1H, C3H), 3.76 (s, 3H, OMe); $^{13}$C NMR (CDCl$_3$) d 183.45 (s, C=O), 178.2 (s, C=O), 158.48 (s), 152.93 (s), 150.07 (s), 143.71 (s, 2 C), 143.57 (s, 2 C), 125.52 (d, 4 C), 124.43 (d, 2 C), 124.3 (d, 2 C), 105.71 (d), 56.48 (q, OMe), 47.5 (d), 47.17 (d).

4a,9,9a,10-Tetrahydro-9,10-[1',2']benzenoanthracene-1,4-dione (TT6):

A solution of 1 g (5.6 mmol) of anthracene (13) and 2.42 g (22 mmol) of 1,4-benzoquinone (2) in 20 mL of toluene was heated under reflux under argon for 24 h. The solution was cooled to room temperature, diluted with 100 mL of methylene chloride, washed with water, dried (MgSO$_4$), and concentrated to give yellow solids. Proton NMR spectrum indicated desired product and starting quinone 2. The solids were washed with ether several time (the product is insoluble in ether and benzoquinone dissolves), and the remaining solids were dried under vacuum to give 1.56 g (98% yield) of TT6; mp 219–221° C.; $^1$H NMR (CDCl$_3$) d 7.40 (dd, J=5, 3 Hz, 2H), 7.2~7.17 (m, 4H), 7.08 (dd, J=5, 3 Hz, 2H), 6.32 (s, 2H, C2,3 Hs), 4.87 (s, 2H, C9,10 Hs), 3.14 (s, 2H, C4a,9a Hs); $^{13}$C NMR (CDCl$_3$) d 198.29 (s, C=O), 141.49 (s), 140.53 (d), 139.64 (s), 126.68 (d), 126.59 (d), 124.68 (d), 123.83 (d), 49.0 (d), 48.85 (d).

9,10-Dihydro-9,10-[1',2']benzenoanthracene-1,4-dione (TT7):

The procedure is the same as that of the preparation of TT9 from TT8. A solution of 1 g (3.5 mmol) of TT6 and 0.784 g (14 mmol) of KOH in 50 mL of p-dioxane and 10 mL of water was stirred at room temperature for 2 h. The solution was acidified with 1 N HCl until pH=1, extracted twice with methylene chloride, and the combined methylene chloride layer was washed with brine, dried (MgSO$_4$), concentrated to give dark brown solids. The proton NMR spectrum indicated a mixture of the diol (major product) and TT7 (minor). The mixture was stirred with 2 g (8.6 mmol) of silver oxide and 2 g (14 mol) of anhydrous sodium sulfate in 60 mL of dried acetone at room temperature under argon for 3 h. The mixture was filtered through Celite, rinse with methylene chloride, and the filtrate was concentrated to give dark brown solids. Column chromatographic separation of the crude product with silica gel using a gradient mixture of hexane and ether to give 0.7 g (70% yield) of TT7. Mp 295–298° C.; $^1$H NMR (CDCl$_3$) d 7.42 (dd, J=5, 3 Hz, 4H), 7.03 (dd, J=5, 3 Hz, 4H), 6.6 (s, 2H, C2,3 Hs), 5.8 (s, 2H, C9,10 Hs); $^{13}$C NMR (CDCl$_3$) d 183.52 (s, C=O), 151.92 (s), 143.57 (s, 4 C), 135.39 (d, 2 C), 125.57 (d, 4 C), 124.42 (d, 4 C), 47.36 (d, C9,10).

5,8-Dimethoxy-2-methoxycarbonyl-4a,9,9a,10-tetrahydro-9,10-[1',2']benzeno-anthracene-1,4-dione (TT10) and 5,8-Dimethoxy-4a-methoxycarbonyl-9,9a,10-trihydro-9,10-[1',2']benzenoanthracene-1,4-dione (TT11):

A mixture of 0.2 g (0.00119 mol) of methyl gentisate (14), 0.2 g (0.0014 mol) of potassium carbonate and 0.6 g (0.0026 mol) of silver oxide in 10 mL of benzene (freshly distilled) was stirred at 50° C. (bath temperature) under argon for 10 min under dark. The reaction mixture was cooled to room temperature, filtered through Celite, rinsed with small amount of ether, concentrated on a rotary evaporator and then under vacuum to give 0.198 g (100% yield) of methoxycarbonyl-1,4-benzoquinone (15); $^1$H NMR (CDCl$_3$) d 7.13 (s, 1H, C3 H), 6.84 (s, 2H, C5,6 Hs), 3.92 (s, 3H, OMe). The proton NMR spectrum indicates the material is about 100% pure and is used in the next step without purification.

A solution of 73 mg (0.44 mmol) of 15 and 70 mg (0.294 mmol) of 1,4-dimethoxyanthracene (1) in 1 mL of toluene was heated at 70° C. for 14 h and under reflux for 5 h under argon. The solution was cooled to room temperature and subjected to a silica gel column using gradient mixtures of hexane, ether and ethyl acetate to give 69 mg (58% yield) of TT11 and 44 mg (40% yield) of TT10. Compound TT11: mp 176–178° C.; $^1$H NMR (CDCl$_3$) d 7.24 (m, 1H), 7.18 (m, 1H), 7.05 (dd, J=5, 3 Hz, 2H), 6.65 (dd, J=10, 9 Hz, 2H, C6,7 Hs), 6.38 (d, J=10 Hz, 1H, C2H), 6.28 (d, J=10 Hz, 1H, C3H), 5.67 (s, 1H, C10H), 5.27 (d, J=2.4 Hz, 1H, C9H), 3.86 (s, 3H, OMe), 3.81 (s, 3H, OMe), 3.61 (s, 3H, OMe), 3.5 (d, J=2.4 Hz, 1H, C9a H); $^{13}$C NMR (CDCl$_3$) d 196.67 (s, C=O), 193.48 (s, C=O), 169.23 (s, C=O of ester), 149.85 (s), 148.08 (s), 140.61 (2), 140.22 (d), 139.31 (d), 131.4 (s), 129.11 (s), 126.7 (d), 126.59 (d), 125.93 (d), 124.68 (d), 111.2 (s), 109.4 (d), 104.36 (d), 63.4 (s), 56.23 (q), 55.91 (q), 53.9 (q), 53.17 (d), 45.02 (d), 42.1 (d). Compound TT10: $^1$H NMR (CDCl$_3$) d 7.4 (m, 2H), 7.18 (m, 2H), 6.54 (s, 2H), 6.42 (s, 1H of one isomer, exo or endo), 6.25 (s, 1 H of one isomer), 5.28 (m, 1H), 5.25 (m, 1H), 3.86 (s, 3H, OMe), 3.83 (s, 3H, OMe), 3.82 (s, 3H, OMe), 3.15 (m, 1H), 3.12 (m, 1H).

9,10-Dihydro-9,10-[1',2']benzenoanthracene-1,4,5,8-tetraone (TT1):

Preparation of endo-(5aS,8aR,9S,10R )-1,4-dimethoxy-5a,8a,9,10-tetrahydro-9,10[1',2']benzenoanthracene-5,8-dione (18a) and exo-(5aR,8aS,9S,10R)-1,4-Dimethoxy-5a,8a,9,10-tetrahydro 9,10-[1',2']benzenoanthracene-5,8-dione (18b).

To a solution of 1.19 g (0.005 mol) 1,4-dimethoxyanthracene (1) in 20 mL of toluene was added a solution of 0.54 g (0.005 mol) 1,4-benzoquinone (2) in 15 mL of toluene, the resulting solution was heated at reflux for 3 hr., added 1.08 g (0.01 mol) 1,4-benzoquinone. After 24 hr., another portion of 1.08 (0.01 mol) 1,4-benzoquinone was added. The solution was refluxed for 19 h. Subsequent evaporation of solvent and sublimation of excess 1,4-benzoquinone gave a mixture of 1.85 g of isomers 18a and 18b (~100% yield) in a ratio of 1:1. Further purification was performed and the products (1.73 g) were used for the next step. The endo-, exo-isomers were assigned according to $^1$H NMR spectra analysis. The deshielding effect between enone ring and benzene ring in the exo-configuration resulted in a downfield shift of proton signals on these two rings, especially the benzene protons (7.41 ppm, 7.17 ppm), compared with those of endo-isomer (7.20 ppm, 7.06 ppm). Mp. 198~201° C.; 18a (endo-): $^1$HNMR (CDCl$_3$) d 7.20 (dd, J=5.5, 3.2 Hz, 2H, C3',6'), 7.06 (dd, J=5.5, 3.2 Hz, 2H, C4', 5'H), 6.59 (s, 2H, C2,3H), 6.28 (s, 2H, C6,7H), 5.31 (s, 2H, C9,10H), 3.82 (s, 6H, OMe). 18b (exo-): Mp 218–221° C. $^1$HNMR (CDCl$_3$) d 7.41 (dd, J=5.5, 3.2 Hz, 2H, C3',6H'), 7.17 (dd, J=5.5, 3.2 Hz, 2H, C5',4'H), 6.59 (s, 2H, C2,3H), 6.31 (s, 2H, C6,7H), 5.31 (s, 2H, C9,10H), 3.75 (s, 6H, OMe). The structure of this exo isomer (the two C4a,9a Hs orient at the same side with the phenyl ring) was proven by a single crystal X-ray diffraction.

Exoisomer: $^{13}$C NMR (CDCl$_3$) d 198.44, 148.500, 140.46, 139.95, 131.21, 126.52, 124.86, 109.09, 56.04, 48.51, 42.16.

Endoisomer: $^{13}$C NMR (CDCl$_3$) d 198.12, 149.13, 141.808, 140.29, 128.32, 126.45, 123.99, 109.32, 126.45, 123.99, 109.76, 56.39, 48.80, 42.38.

Preparation of 1,4dimethoxy-5,8-dihydroxy-9,10-dihydro-9,10-[1',2']benzenoanthracene (19):

To a solution of 1.73 g (0.005 mol) of 18a&b in 100 mL of 1,4-dioxane was added 10.61 g of potassium hydroxide in 100 mL of water. The resulting mixture was stirred at 35° C. for 18.5 hr., neutralized by 6N hydrochloric acid solution, and extracted with methylene chloride twice (40 ml each), and once with ethyl acetate (40 ml). The combined extracts were dried over anhydrous magnesium sulfate, and concentrated to give 1.75 g of crude product 19 (~100% crude yield). No purification was performed at this stage. $^1$H NMR (CDCl$_3$) d: 3.80 (s, 6H, —OCH$_3$), 6.20 (s, 2H, C 9,10 Hs), 6.34 (s, 2H, C 6,7 Hs), 6.51 (s, 2H, C 2,3H s), 7.00 (dd, J=5.5, 3.2 Hz, 2H, C 12,15 Hs), 7.43 (dd, J=5.5, 3.2 Hz, 2H, C 13,14 Hs].

5,8-Dimethoxy-9,10-dihydro-9,10[1'2']benzenoanthracene-1,4-dione (20):

A mixture of 1.73 g (0.005 mol) of crude 19, 6 g (0.042 mol) of sodium sulfate and 5.8 g (0.025 mol) of silver oxide in 150 mL of acetone was heated at reflux for 22 hr. The reaction mass was filtered through Celite and washed with methylene chloride. The filtrate was dried over anhydrous magnesium sulfate, concentrated and column chromatographed on silica gel using a gradient mixture of ethyl acetate and hexane as eluant to give 1.15 g of pure 20 in a yield of 67.25% (based on crude 19). The melting point and IR agree with reported data.[1] M.p. 266~271° C. (decom.), lit.[1] 271.5~272.5° C.; IR: 3060 cm$^{-1}$ (Ar—H), 1660 cm$^{-1}$ (C=O), 1584 cm$^{-1}$ (aromatic C=C), 1258 cm$^{-1}$ (C—O); $^1$H NMR (CDCl$_3$) d 7.44 (dd, J=5.3, 3.2 Hz, 2H, C12,13 Hs), 7.00 (dd, J=5.3, 3.2 Hz, 2H, C11,14 Hs), 6.54 (s, 2H, C6,7 Hs), 6.51 (s, 2H, C2,3 Hs), 6.23 (s, 2H, C9,10 Hs), 3.79 (s, 6H, OMe); $^{13}$C NMR (CDCl$_3$) d 183.52 (s, C=O), 152.75 (s, C—OMe), 149.51 (s), 144.14 (s), 135.23 (d), 133.44 (s), 125.28 (d), 124.51 (d), 109.36 (d, C2,3), 56.30 (s, OMe), 41.30 (d, CH).

Preparation of 9,10-Dihydro-9,10-[1',2']-benzenoanthracene-1,4,5,8-tetrone (TT1):

To a solution of 0.4 g (1.17 mmol) of compound 20 in 30 mL of acetonitrile was added dropwise a solution of 3.2 g (5.84 mmol) of ceric ammonium nitrate in 70 mL of a mixture of dioxane and water (3:1) at r.t under argon. After stirred for 3 h, the reaction mixture was extracted with methylene chloride four times (40 mL each). The combined methylene chloride extracts were dried over anhydrous magnesium sulfate, concentrated and column chromatographed on silica gel using a gradient mixture of ethyl acetate and petrolium ether as eluant to give 0.37 g of bisquinone TT1 in a yield of about 100%. Recrystallization in methylene chloride and petroleum ether gave TT1 as yellow needle-like crystals; m.p. 303~305° C. (dec.), lit.[1]>220°C. (dec.); $^1$H NMR (CDCl$_3$) d 7.49 (dd, J=5.3, 3.0 Hz, 2H, C12,13 Hs), 7.08 (dd, J=5.3, 3.0 Hz, 2H, C11,14 Hs), 6.65 (s, 4H, =CH—CO), 6.18 (s, 2H, CH); $^{13}$C NMR(CDCl$_3$) d 182.22 (s, C=O), 151.51 (s), 142.20 (s), 135.41 (d), 125.91 (d), 125.47 (d), 42.13 (d).

Preparation of Dimethyl Butadiene-2,3-dicarboxylate (16): (Z)-Dimethyl 2,3-dimethyl-2-butenedioate (21):

To a solution of 2 g (0.0158 mol) of 2,3-dimethylmaleic anhydride in 40 mL of methanol was added 0.2 mL of concentrated sulfuric acid. After refluxing for 7 days, the solution was diluted with 100 mL of methylene chloride, neutralized with aqueous sodium bicarbonate solution. The methylene chloride layer was washed with 30 mL of brine, the aqueous layer was extracted with methylene chloride four times (30 mL twice and 15 mL twice). The combined methylene chloride layer and extracts were dried over anhydrous magnesium sulfate, concentrated to give 2.11 g of crude product. $^1$H NMR check indicated about 25% of starting material existing, the crude mixture with 0.2 mL of concentrated sulfuric acid in 40 mL of methanol was heated at reflux again for 5 days. The solution was concentrated until 30% of methanol was left, neutralized with saturated sodium bicarbonate aqueous solution, followed by addition of 30 mL of brine solution, and the mixture was extracted with ethyl acetate four times (100 mL once, 30 mL three times). The combined ethyl acetate extracts were dried over anhydrous magnesium sulfate, concentrated to give 3.26 g of crude product 21 (~100% yield). It was of satisfactory purity for the next step. $^1$H NMR (CDCl$_3$) d 3.77 (s, 6H, OMe), 1.95 (s, 6H, Me)

(Z)- and (E)-Dimethyl-2,3-bis[bromomethyl]-2-butenedioate (22a & 22b):

A mixture of 3.2384 g (0.0188 mol) of butenedioate 21, 7.37 g (0.04 mol) of N-bromosuccinimide (NBS) and 100 mg (cat.) of 2,2'-azobisisobutyronitrile (AIBN) in 50 mL of carbon tetrachloride was heated under reflux and irradiated with a 275 W sunlamp for 3 h. The reaction solution was cooled, diluted with 150 mL of ether, and filtered. The filtrate was concentrated, and flash column chromatographed using a gradient mixture of ether-hexane as eluant to give 1.33 g of oily liquid trans-isomer 22b (18.4% yield) and 4.40 g of oily liquid cis-isomer 22a (71.6% yield) with a total yield of 90%. The assignment of 22a and 22b was based on the reported $^1$H NMR data.

22a: $^1$H NMR (CDCl$_3$) d 4.50 (s, 4H, CH$_2$ Br), 3.91 (s, 6H, OMe); $^{13}$C NMR (CDCl$_3$) d 165.54 (s, C=O), 136.95 (s, C=), 52.97 (s, OMe), 26.75 (t, CH$_2$Br)

22b: $^1$H NMR (CDCl$_3$) d 4.24 (s, 4H, CH$_2$Br), 3.84 (s, 6H, OMe); $^{13}$C NMR (CDCl$_3$) d 165.96 (s, C=O), 137.06 (s, C=), 52.99 (s, OMe), 23.95 (CH$_2$Br).

Dimethyl 1,3-butadiene-2,3-dicarboxylate (16):

To a solution of 6.53 g (0.02 mol) of bromoesters 22 in 20 mL of acetone was added 9.49 g (0.06 mol) of sodium thiosulphate and 9.96 g (0.06 mol) of potassium iodide. After refluxing for 2 hr., The mixture was cooled, poured onto 50 g of ice, and extracted with methylene chloride three times (150 mL once, 50 mL twice). The combined methylene chloride extracts were washed with 20 mL of saturated aqueous sodium chloride, dried over anhydrous magnesium sulfate, concentrated, and column chromatographed on silica gel using a gradient mixture of hexane-ethyl acetate as eluant to give 2.8206 g of butadiene 16 in a yield of 83%. $^1$H NMR (CDCl$_3$) d 6.71 (dd, J=1.4, 0.6 Hz, 2H, =CH), 5.83 (dd, J=1.4, 0.6 Hz, 2H, =CH), 3.76 (s, 6H, OMe); $^{13}$C NMR (CDCl$_3$) d 166.20 (s, C=O), 138.42 (s, =C), 127.79 (t, =CH$_2$), 52.09 (q, OMe).

(4aS*,7aR*,11aS*,14aR*)-Tetramethyl 1,4,4a,5,6,7,7a,8, 11,11a,12,13,14,14a-tetradecahydro-5,7,12,14-tetraoxo-6, 13-[1',2']benzenopentacene-2,3,9,10-tetracarboxylate (TT4) and Compound 17:

A solution of 0.14 g (0.45 mmol) of TT1 and 0.17 g (11 mmol) of compound 16 in 5 mL of toluene was maintained under argon and heated under reflux for 22 h. The solution was directly subjected onto a silica gel column and eluted with a gradient mixture of hexane, methylene chloride, and ethyl acetate to give 0.160 g (54% yield) of TT4 and 30 mg (14% yield) of compound 17. Recrystallization of TT4 from methylene chloride gave light yellow crystals. Single crystal X-ray diffraction analysis was carried on a crystal and the structure was solved. The following Figure shows the ORTEP drawing of the compound. $^1$H NMR (CDCl$_3$) d 7.45 (m, 2H), 7.09 (m, 2H), 6.07 (s, 2H, C6,13 Hs), 3.75 (s, 12H, OMe), 3.2 (bs, 4H, 3C4a,7a,11a,14a Hs), 2.62~2.5 (m, 8H); $^{13}$C NMR (CDCl$_3$) d 192.36 (s, C=O), 167.12 (s, C=O of ester), 154.04 (d), 141.49 (s), 132.51 (d), 126.02 (s), 125.57 (s), 52.33 (q, OMe), 45.5 (d), 43.27 (d), 25.48 (t).

Compound 17: $^1$H NMR (CDCl$_3$) d 7.42 (dd, J=5, 3 Hz, 2H), 7.01 (dd, J=5, 3 Hz, 2H), 6.38 (s, 2H), 6.10 (s, 2H), 3.71 (s, 6H, OMe), 3.17 (bs, 2H, CHC=O), 2.60 (dd, J=17, 4 Hz, 2H), 2.43 (dd, J=17, 4 Hz, 2H). (19).

(4aS*, 5S*, 7R*, 12S*, 14R*, 7aR*, 11aS*, 14aR*)-Tetramethyl 1,4,4a,5,6,7,7a,8,11,11a,12,13,14,14a-tetradecahydro-5,7,12,14-tetrahydroxy-6,13-[1',2']benzenopentacene-2,3,9,10-tetracarboxylate (TT12):

To a solution of 0.10 g (0.15 mmol) of TT4 in 7 mL of methanol (distilled over magnesium turning) under argon were added 0.52 g (1.4 mmol) of CeCl$_3$.7H$_2$O and 51 mg (1.4 mmol) of sodium borohydride. The solution was stirred at room temperature for 12 h, diluted with 70 mL of methylene chloride, and washed with aqueous ammonium chloride and brine. The organic layer was dried (MgSO$_4$), concentrated to give 88 mg (89% yield) of TT12. Proton NMR spectrum indicates the material is pure. $^1$H NMR (CDCl$_3$) d 7.3 (dd, J=5, 3 Hz, 2H), 7.01 (dd, J=5, 3 Hz, 2H), 5.15 (s, 2H, C6,13 Hs), 4.47 (bs, 4H, CHO), 3.74 (s, 12H, OMe), 3.2 (bs, 4H, OH), 2.53 (dd, J=17,4 Hz, 4H), 2.27 (dd, J=17, 4 Hz, 4H), 2.06(m, 4H); $^{13}$C NMR (CDCl$_3$ and acetone-d6) d 168.24 (s, C=O of ester), 145.74 (s), 145.45 (s), 134.46 (s), 123.49 (d), 121.76 (d), 68.32, 59.66, 51.28, 49.36, 34.19.

2-Bromo-3-(methylamino)-9,10-dihydro-9,10-[1',2']benzenoanthracene-1,4,5,8-tetraone (TT14) and 2-hydroxy-3-(methylamino)-9,10-dihydro-9,10-[1',2']benzenoanthracene-1,4,5,8-tetraone (TT15):

A solution of 24 mg (0.057 mmol) of TT13 and 1.8 mg (0.057 mmol) of methylamine in 1 mL of THF was stirred under argon at room temperature for 20 min. The solution was diluted with ether, washed with water and brine, dried (MgSO$_4$), and concentrated. Column chromatographic separation of the crude on silica gel using a gradient mixture of hexane and ether as eluant to give 6 mg (24% yield) of TT14 and 6 mg (29% yield) of TT15. For TT14: $^1$H NMR (CDCl$_3$) d 7.48 (dd, J=5, 3 Hz, 1H), 7.45 (dd, J=5, 3 Hz, 1H), 7.07 (dd, J=5, 3 Hz, 2H), 6.64 (s, 2H, C6,7 Hs), 6.28 (s, 1H), 6.11 (s, 1H), 5.88 (bs, 1H, NH), 3.33 (d, J=5.6 Hz, 3H, MeN). For TT15: $^1$H NMR (CDCl$_3$) d 7.45 (m, 2H, Ar—H), 7.04 (m, 2H, Ar—H), 6.41 (2d, J=6.3 Hz, 2H, C6,7-Hs), 6.23 (s, 1H), 6.1 (s, 1H), 5.9 (bs, 1H, NH), 4.8 (s, 1H, OH), 3.33 (d, J=5.8 Hz, 3H, MeN).

2-Bromo-3-methoxy-6-(dimethylamino)-9,10-dihydro-9,10-[1',2']benzenoanthracene-1,4,5,8-tetraone (TT16):

To a solution of 35 mg (0.083 mmol) of TT13 in 2 mL of THF, a stream of dimethylamine was added via a syringe for few minutes. The solution turned dark brown color immediately, the dimethylamine gas was disconnected, and the solution was stirred at 0° C. for 10 minutes. The solvent and excess of dimethylamine were removed via rotary evaporator and residue was column chromatographed on silica gel using a gradient mixture of hexane and ethyl acetate as eluant to give 5 mg of recovered starting material TT13 and 28 mg of the product TT16. $^1$H NMR (CDCl$_3$) d 7.45 (m, 2H, Ar—H), 7.04 (m, 2H, Ar—H), 6.22 (s, 1H), 6.15 (s, 1H), 5.4 (s, 1H, C7H), 3.81 (s, 3H, OMe), 3.12 (s, 6H, Me$_2$N).

2-Bromo-3-[2-(ethoxycarbonyl)ethylamino]-9,10-dihydro-9,10-[1',2']benzenoanthracene-1,4,5,8-tetraone (TT17) and 2-hydroxy-3-[2-(ethoxycarbonyl)ethylamino]-9,10-dihydro-9,10-[1',2']benzenoanthracene-1,4,5,8-tetraone (TT18).

To a mixture of 0.5 g (0.00325 mol) of b-alanine ethyl ester hydrochloride in 5 mL of THF under argon, 0.156 g (0.00325 mol; 50% oil dispersion) was added. The mixture was stirred at room temperature for 1 h, THF was evaporated under vacuum and while solids, b-alanine ethyl ester and sodium chloride, were obtained.

To a solution of 64 mg (0.151 mmol) of TT13 in 2 mL of THF and 0.5 mL of DMF under argon was added 0.302 mmol each of the above mixture of b-alanine ethyl ester and sodium chloride. The solution was stirred at room temperature for 16 hours, diluted with methylene chloride, the organic layer was washed with water twice, brine, dried (MgSO$_4$), and concentrated. The proton NMR spectrum of the crude products indicated a mixture of TT17 and TT18. This crude product was subjected to column chromatographic separation on silica gel using a gradient mixture of hexane and ethyl acetate as eluant to give 46 mg (69% yield) of TT18. $^1$H NMR (CDCl$_3$) d 7.45 (m, 2H, Ar—H), 7.04 (m, 2H, Ar—H), 6.42 (ABq, J=8.4 Hz, 2H, C6,7 H's), 6.23 (s, 1H, C9H), 6.10 (s, 1H, C10H), 4.15 (q, J=7 Hz, 2H, CH$_2$), 4.10 (broad S, 2H, CH$_2$N), 2.64 (t, J=6 Hz, 2H, CH$_2$CO), 1.25 (t, J=7 Hz, 3H, CH$_3$).

2-Hydroxy-3-[(S)-5-(hydroxycarbonyl)-5-aminopentylamino]-9,10-dihydro-9,10-[1',2']benzenoanthracene-1,4,5,8-tetraone (TT20).

To a mixture of 0.5 g (0.0027 mol) of L-lysine monohydrochloride in 5 mL of THF under argon was added 0.1315 g (0.0027 mol; 50% oil) of sodium hydride. The mixture was stirred at room temperature for 2 h, concentrated to dryness under vacuum to give a mixture of L-lysine and sodium chloride as white solids. To a solution of 40 mg (0.095 mmol) of TT13 in 2 mL of THF and 0.5 mL of DMF was added 20 mg of the above mixture of L-lysine and sodium chloride. The mixture was stirred at room temperature for 2 days, concentrated to dryness under vacuum and the crude product was purified by HPLC using a Econosphere C8 (10 m) semi-preparative column (250 mm×10 mm), 40% acetonitrile in water as solvent, to give pure TT20 (came out in 2 minutes). $^1$H NMR (D$_2$O) d 7.54 (m, 2H, Ar—H), 7.10 (m, 2H, Ar—H), 6.56 (s, 2H, C6,7 H's), 6.2 (s, 1H, C9H), 6.07 (s, 1H, C10H), 3.76 (t, J=6 Hz, 1H, CH), 3.03 (dd, J=8 Hz, 7 Hz, 2H, CH$_2$N), 1.90 (m, 2H, CH$_2$), 1.72 (m, 2H, CH$_2$), 1.48 (m, 2H, CH$_2$).

One Pot Synthesis of 5,8-Disubstituted Triptycene Monoquinones and Inhibition Studies In the reported synthesis of 5,8-disubstituted triptycene monoquinones, (Bartlett, P. D.; Ryan, M. J.; Cohen, S. G. J. Am. Chem. Soc. 1942, 64, 2649; Skvarehenko, V. R.; Shalaev, V. K.; Klabunovskii, E. I. Russ. Chem. Rev. 1974, 43, 951; Iwamura, H.; Maino, K. An intramolecular triptycene quinhydrone. J. Chem. Soc. Chem. Commun. 1978, 720.; Quast, H.; Fuchsbauer, H. -L. Chem. Ber. 1986, 119, 1016–1038; Quast, H.; Fuchsbauer, H. -L. Chem. Ber. 1986, 119, 2414; Patney, H. K. Synthesis 1991, 694. Charge-transfer complexes; Lipczynska-Kochany, E.; Iwamura, H. Chem. Lett. 1982, 1075; Daub, J.; Jakob, L.; Salbeck, J.

Chem. Ber. 1988, 121, 2187. Radical Anions: Russell, G. A.; Suleman, N. K. J. Am. Chem. Soc. 1981, 103, 1560–1561. Liquid Crystals; Norvez, S. J. Org. Chem. 1993, 58, 2414) a sequence of three reactions was carried out: Diels-Alder reaction of 1,4-dimethoxyanthracene (Criswell, T. R.; Klanderman, B. H. J. Org. Chem. 1974, 39, 770) and p-benzoquinone followed by isomerization of the adducts (endo- and exo-adducts) with potassium hydroxide and then oxidation with silver oxide. These three reactions have been successfully combined into one simple operation. Hence, heating of anthracene 2 (derived from the reduction of 1,4-anthracenedione (Perchellet, E. M.; Magill, M. J.; Huang, X.; Brantis, C. E.; Hua, D. H.; Perchellet, J. P. Anti-cancer Drugs, 1999, 10, 749) with sodium hydrosulfite followed by sodium hydride and iodomethane), 1.4 equiv of methoxyhydroquinone (3), 2.7 equiv of silver oxide, and 0.2 equiv of zinc iodide in toluene under reflux for 4 days gave a 70% yield of triptycene monoquinone 4 (Scheme 14). Presumably, silver oxide oxidizes methoxyhydroquinone to methoxy-p-benzoquinone which undergoes Diels-Alder reaction with anthracene 2 to give adducts 5 (endo- and exo-isomers). Compound 5 then undergoes oxidation with silver oxide to give quinone 4. A catalytic amount of zinc iodide was added to facilitate the Diels-Alder reaction. No other regioisomers (such as isomers with methoxy substituent attached at C4a) were detected. To verify the reaction sequence, methoxyquinone 6, obtained from the oxidation of 3 with silver oxide and potassium carbonate in benzene (98% yield), was treated with anthracene 2 in toluene at 150° C. in a sealed tube to give adducts 5 (48% yield). Isomerization of ketones 5 with KOH in p-dioxane and water followed by oxidation with silver oxide gave monoquinone 4 (95% overall yield). Oxidation of monoquinone 4 with ceric ammonium nitrate afforded a 94% yield of triptycene bisquinone 7. Regioselective bromination of 7 was achieved by the treatment with N-bromosuccinimide (NBS) in DMF at 25° C. for 10 h to give bromoquinone 1 (45% yield). Alternatively, compound 1 can also be obtained from the bromination of monoquinone 4 with NBS in DMF at 40° C. followed by oxidation with ceric ammonium nitrate (59% overall yield). The bromination of quinones with NBS has not been reported previously, and apparently, reactivity of the methoxyquinone moiety towards NBS is greater than that of quinone and 1,4-dimethoxyphenyl moieties. Likely, the methoxy substituent of 7 or 4 (at C2) enhances nucleophilicity of adjacent double bond carbon resulting the bromination.

Scheme 14

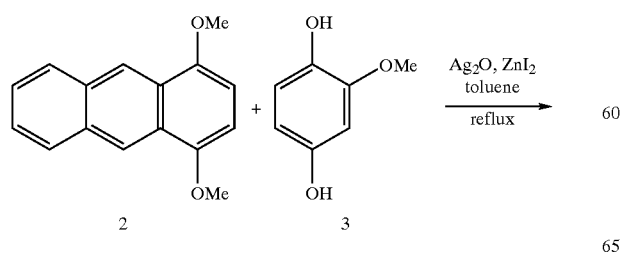

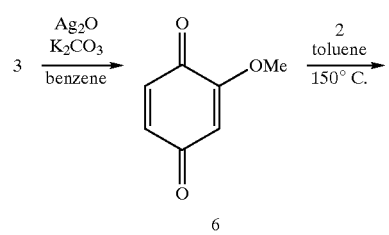

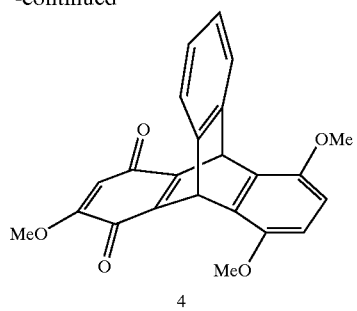

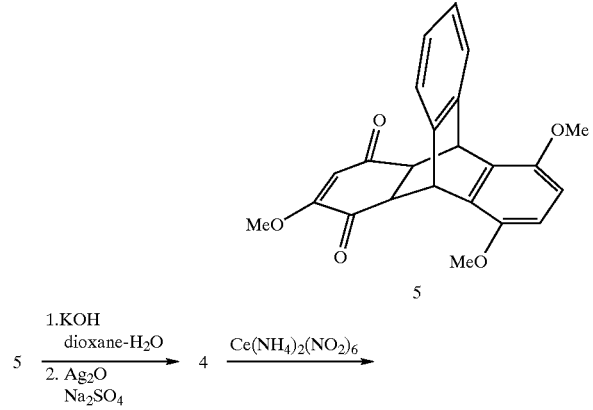

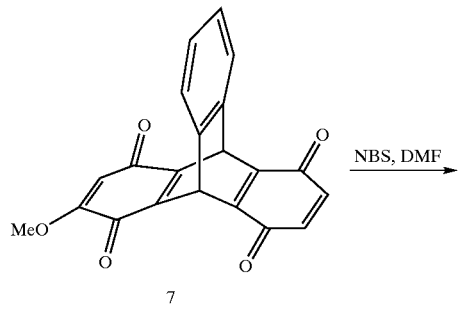

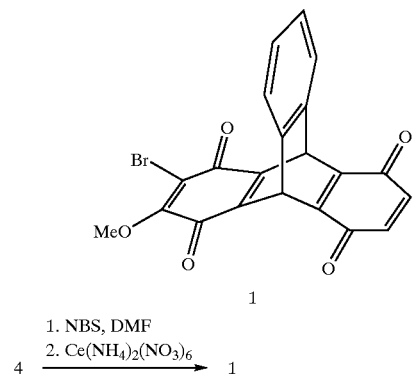

To synthesize new analogs, 1 was treated with primary and secondary amines (Scheme 15). Surprisingly, compound 1 reacts with primary amines such as methylamine and secondary amines such as dimethylamine to give different regio-isomeric products. Hence, addition of bromide 1 with methylamine in THF at 0° C. for 20 min. gave a 66% yield of displacement product 8. On the other hand, when 1 was treated with dimethylamine in THF at 0° C., a 96% yield of regioisomers 9 and 10 (a ratio of 1:1) was isolated. Compounds 9 and 10 were separated by silica gel column chromatography. The regiochemistry of 9 and 10 has not been determined. The presence of bromine atom in the products was indicated by their mass spectra in which the M+2 peaks ($^{81}Br$ isotope) almost equal in intensity to the molecular (EI) or quasimolecular (CI) ions. No other by-products are identifiable in these reactions. These unusual addition reactions are unprecedented. It has been reported that p-benzoquinone undergoes addition reactions with aliphatic primary amines to give a mixture of products including mono- and di-adducts from the 1,4-addition reactions, and tetrachloro-1,4-benzoquinone and 2,3-dichloro-1,4-naphthoquinone react with secondary amines to give displacement products (addition to the double bond followed by elimination of chlorine). Contrary to these literature results, bromide 1 undergoes displacement of the methoxy group instead of bromine with primary amines and simple 1,4-addition on the unsubstituted quinone ring followed by oxidation with secondary amines, exclusively. Presumably, a less basic primary amine, methylamine, undergoes 1,4-addition reaction on the greater electron-deficient bromoquinone ring. Since the C2-bromine of 1 is an electron-withdrawing group, the anion resulted from the addition of an amine on C3 would be more stabilized than that from the addition on C2; resulting a displacement of methoxy group to provide compound 8. On the other hand, a more basic secondary amine, dimethylamine, is less affected by electronic (since it is a more reactive amine) effect of the quinone ring and is more affected by steric effect, in turn it prefers the addition on the unsubstituted (less hindered) quinone moiety to provide compounds 9 and 10.

Scheme 15

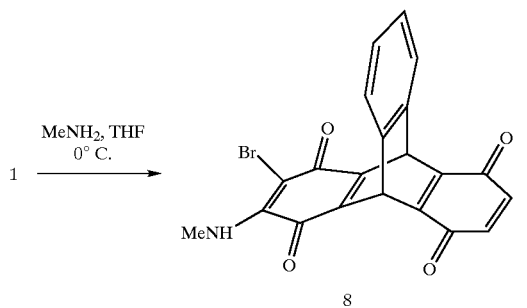

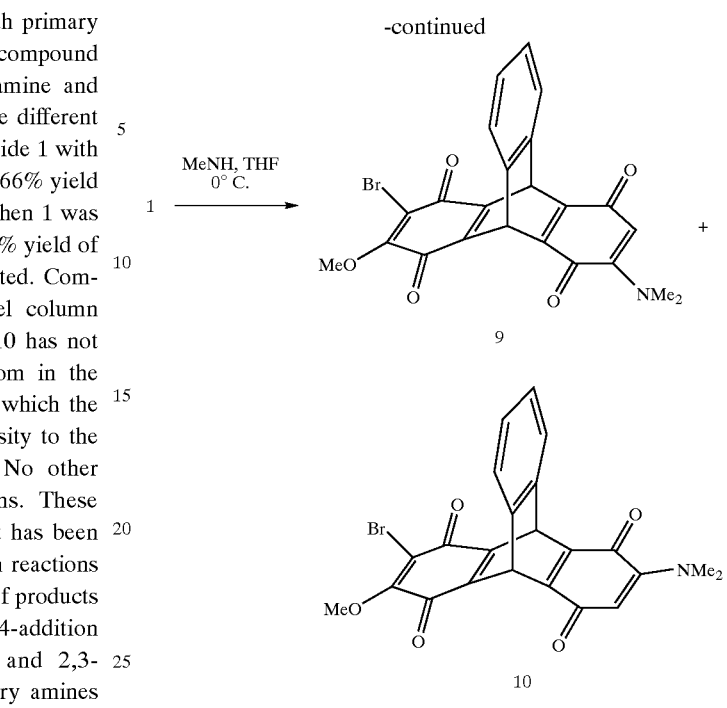

Due to the potent anticancer activity of amine 8 (vide infra) and a need of water soluble analogs, aliphatic primary amines containing ester function were used to synthesize various triptycene quinones, and their biological activities were studied (Scheme 16).

Scheme 16

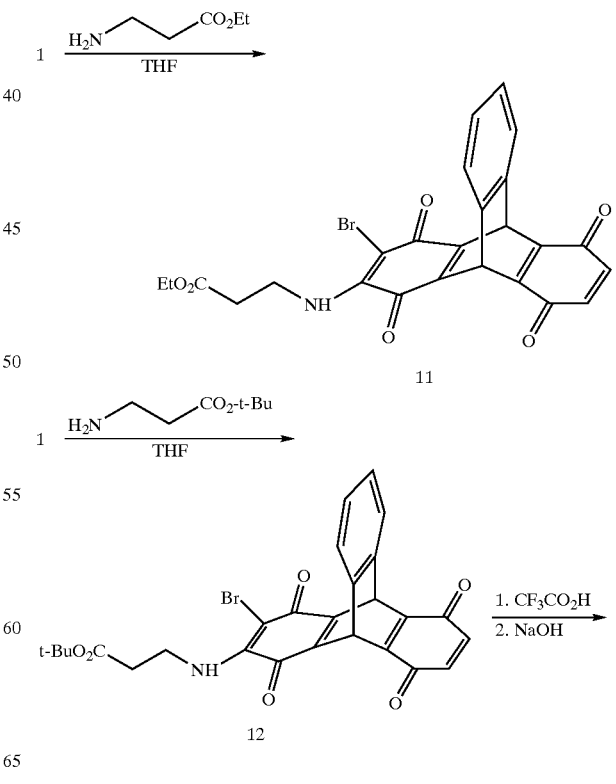

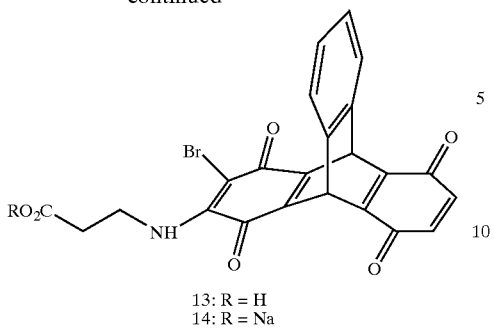

13: R = H
14: R = Na

Treatment of bromide 1 with ethyl 2-aminopropanoate in THF at −40° C. for 6 h afforded a 46% yield of displacement product 11 along with starting material 1 (30% recovery). No other regioisomers were detected. Similarly, reaction of 1 with t-butyl 2-aminopropanoate at −40° C. for 8 h gave a 62% yield of 12. Recrystallization of 12 in hexane:ethyl acetate (5:1) afforded single crystals which structure was unequivocally shown by X-ray analysis. Deprotection of the t-butyl ester of 12 with trifluoroacetic acid in dichloromethane gave a quantitative yield of acid 13. Sodium salt 14, a water soluble material, w=as obtained from the treatment of 13 with 1 equiv of sodium hydroxide.

When compound 1 was treated with dimethylamine in THF (1 M solution in THF; purchased from Aldrich Chemical Company), a mixture of 9 and 10 (1:1) was obtained (Scheme 18). However, when compound 1 was treated with dimethylamine in THF which prepared by adding dimethylamine (a gas purchased from Linde Company) gas into THF, a mixture of 9, 10, TT24A, and T24B (4:4:1:1) was obtained. Compounds 9, 10, and TT24 were separated by column chromatography. TT24A and TT24B were inseparable, however, carbon-13 NMR spectrum indicates two isomers.

Likely, a small of amounts of methylamine is contaminated in the dimethylamine gas, this methylamine then added to the unsubstituted quinone ring of triptycene bisquinone to produce TT24. This mode of addition is different from the reaction of 1 with pure methylamine. It is suggested that dimethylamine acts as a base and remove the proton of methylamine to provide methylamine anion which is more reactive than methylamine itself, and in turn undergoes addition reaction on the unactivated C=C of the quinone moiety.

Scheme 18

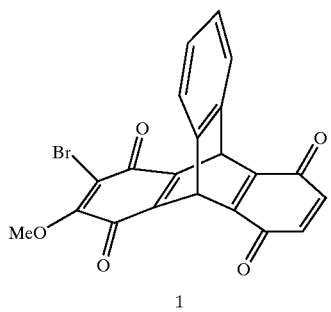

1

1 Me$_2$NH, THF 0° C. (reagent from Aldrich) →

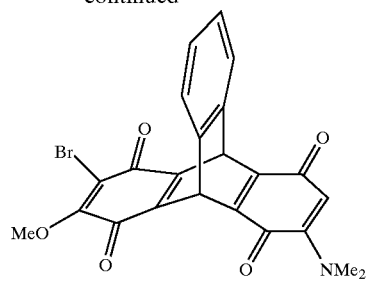

9

+

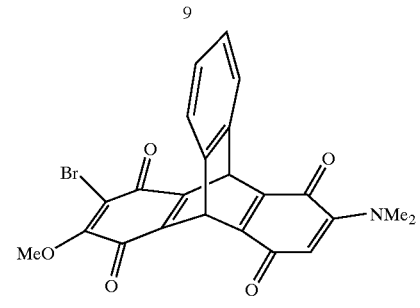

10

1 Me$_2$NH (reagent from a gas cylinder, Linde Co.) THF, 0° C. → 9 + 10 +

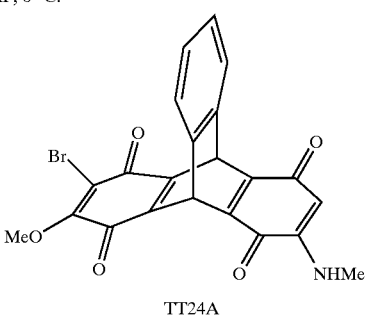

TT24A

+

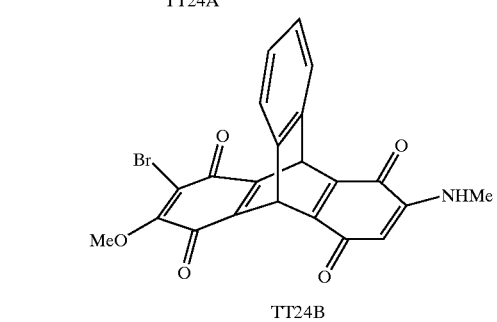

TT24B

Anticancer testing of TT24 show it has an IC$_{50}$ value of 48 nM (or 0.048 μM). The compound is as active as daunomycin.

Anticancer and antimalarial activities of triptycene bisquinones have been evaluated. Table 2 summarizes IC$_{50}$ values (the concentrations of drugs required to inhibit by 50% the viability of L1210 leukemic cells at day 4) of various triptycene bisquinones in the inhibition of L1210 leukemic cell growth. In general, IC$_{50}$ values are in the 0.24~0.43 μM range with the exception of carboxylic acid 13 and its sodium salt 14. Possibly, the passage ability of sodium salt 14 through cell membrane decreases as water solubility increases; in turn, ability in destroying cancer cells decreases. The IC$_{50}$ value of daunomycin, a known anticancer drug, under similar treatment conditions is 0.041 µM. Triptycene bisquinones induce DNA cleavage and inhibit nucleoside transport. In contrast, daunomycin, inhibits topoisomerases I and II, does not block nucleoside transport. Moreover, triptycene bisquinones 7, 8, 9, and ritonavir inhibit Plasmodium falciparum 3D7 (a malaria strain) with $IC_{50}$ values of 8, 4.7, 5.6, and 9.7 µM, respectively. Malaria protease plasmepsin II was also inhibited by compounds 8,9, and ritonavir and $IC_{50}$ values of these compounds are 9.7, 23.6, and 0.10 µM, respectively. Presumably, these reactive triptycene bisquinones undergo addition reactions with lysine, tryptophan, histidine, and cysteine residues of proteins to produce cross-linked proteins.

TABLE 2

Cytotoxicities of triptycene bisquinone analogs in L1210 leukemic cell system in vitro.

| Compound | 1 | 7 | 8 | 9 | 11 | 12 | 13 | 14 |
|---|---|---|---|---|---|---|---|---|
| $IC_{50}$ (µM) | 0.291 | 0.270 | 0.430 | 0.300 | 0.240 | 0.310 | 1.48 | 4.00 |

General Methods. Nuclear magnetic resonance spectra were obtained at 400 MHz for $^1H$ and 100 MHz for $^{13}C$ in deuteriochloroform, unless otherwise indicated. Infrared spectra are reported in wavenumbers (cm$^{-1}$). Mass spectra were taken from a Hewlett Packard 5890A Series II, GC-MS. FAB spectra were taken by using Xe beam (8 KV) and m-nitrobenzyl alcohol as matrix. Methoxyhydroquinone (3), quinizarin, silver oxide, zinc iodide, sodium borohydride methylamine in THF, dimethylamine in THF, ethyl 3-aminopropanoate hydrochloric acid salt, and t-butyl 3-aminopropanoate hydrochloric acid salt were purchased from Aldrich Chem. Co. Davisil silica gel, grade 643 (200~425 mesh), was used for the flash column chromatographic-separation.

1,4-Dimethoxyanthracene (2).

To a cold (0° C.) methanol (20 mL) solution of 1.00 g (0.0042 mol) of quinizarin under argon was added 0.638 g (0.0168 mol) of sodium borohydride. The resulting mixture was stirred at 0° C. for 1 h. To it, 11 mL of 6 N HCl was added dropwise at 0° C. over a period of 10 min. The precipitated orange solids were collected, washed several times with distilled water, dried under vacuum, and recrystallized from acetone-ether to give 0.83 g (95% yield) of anthracene-1,4-dione[17] as yellow crystals, mp 204–206° C. $^1H$ NMR d 8.60 (s, 2H, C 9,10 Hs), 8.10 (dd, J=6.4, 3.2 Hz, 2H, C 5,8 Hs), 7.70 (dd, J=6.4, 3.2 Hz, 2H, C 6,7 Hs), 7.10 (s, 2H, C 2,3 Hs); $^{13}C$ NMR d 184.7 (s, C=O), 140.1 (d), 134.8 (s), 130.2 (d), 129.6 (d), 128.9 (d), 128.4 (d), 128.4 (s).

To 2.00 g (1.00 mmol) of 1,4-anthracenedione, a solution of 6.68 g (38.0 mmol) of sodium hydrosulfite in 50 mL of water and 50 mL of 1,4-dioxane was added. The resulting mixture was stirred at 25° C. for 3 h, and added 100 mL of water. The mixture was cooled over an ice-water bath, and the precipitated dark green solids were collected by filtration, washed twice with water, and dried under vacuum to give 1.75 g (87% yield) of 1,4-dihydroxyanthracene, mp 167–169° C.; $^1H$ NMR d 8.70 (s, 2H, C 9,10 Hs), 8.05 (m, 2H, C 5,8 Hs), 7.50 (s, 2H, C 6,7 Hs), 6.60 (s, 2H, C 2,3 Hs).

To a 0.275 g (11.0 mmol) of pre-washed (with distilled diethyl ether) sodium hydride under argon were added 1.00 g (4.80 mmol) of 1,4-dihydroxyanthracene, 0.75 mL (12.0 mmol) of iodomethane, and 10 mL of DMF (distilled over $CaH_2$). The solution was stirred at 25° C. for 1.5 h, diluted with 20 mL of water, and acidified with 6 N HCl (pH ~2). The mixture was extracted three times with ethyl acetate, and the combined extract was washed twice with water, and brine, dried ($MgSO_4$), concentrated to give 1.07 g (94% yield) of compound 2. Recrystallization from ether:hexane (1:1) gave 0.89 g (78% yield) of yellow solids: mp 132–133° C. (Lit.[6] 134–136° C.); MS, FAB, m/z 239 (M+1), 238 (M+); $^1H$ NMR d 8.70 (s, 2H, C9,10H), 7,97 (dd, J=6.1, 3.6 Hz, 2H, C5,8H), 7.40 (dd, J=6.6, 3.2 Hz, 2H, C6,7H ), 6.55 (s, 2H, C2,3H), 3.97 (s, 6H, $OCH_3$); $^{13}C$ NMR d 149.5 (s, C8a,10a), 131.5 (s, C4a,9a), 128.5 (d, C9,10), 125.5 (d, C5,8), 120.7 (d, C6,7), 100.9 (d, C2,3), 55.6 (s, $OCH_3$).

2,5,8-Trimethoxy-9,10-dihydro-9,10-[1,2] benzenoanthracene-1,4-dione (4).

A mixture of 2.00 g (8.40 mmol) of 1,4-dimethoxyanthracene (2), 1.411 g (10.1 mmol) of methoxyhydroquinone (3), 3.90 g (16.8 mmol) of silver oxide, and 0.536 g (1.68 mmol) of zinc iodide in 30 mL of toluene under argon was refluxed for 3 days. To the mixture, 0.25 g (1.79 mmol) of 3 and 1.30 g (5.60 mmol) of silver oxide were added and the reaction mixture was refluxed for another day. The reaction mixture was cooled, diluted with 200 mL of dichloromethane, filtered through Celite, and the filtrate was washed with aqueous $NH_4Cl$, and brine, dried ($MgSO_4$), concentrated, and column chromatographed on silica gel using a gradient mixture of hexane and ethyl acetate as solvent gave 2.21 g (70% yield) of 4: mp. 108~110° C.; $^1H$ NMR d 7.43 (dd, J=5.5, 3 Hz, 2H), 7.00 (dd, J=5.5, 3 Hz, 2H), 6.52 (s, 2H, C6,7 Hs), 6.25 (s, 1H), 6.23 (s, 1H), 5.71 (s, 1H, C3H), 3.79 (s, 6H, OMe), 3.72 (s, 3H, OMe). $^{13}C$ NMR d 183.5 (C=O), 178.2 (C=O), 158.4, 153.8, 150.9, 150.5, 149.6, 149.5, 144.3, 144.1, 133.6, 133.5, 125.2 (2C), 124.5, 124.4, 109.5, 105.6, 56.4, 56.38, 56.3, 41.5, 41.2. Anal. Calcd for $C_{23}CH_{18}O_5$: C, 73.79; H, 4.85. Found: C, 73.51; H, 5.07.

2,5,8-Trimethoxy-4a,9,9a,10-tetrahydro-9,10-[1,2] benzenoanthracene-1,4-dione (5)

A mixture of 1.00 g (7.10 mmol) of methoxyhydroquinone (3), 2.50 g (10.7 mmol) of silver oxide, and 1.20 g (8.50 mmol) of $K_2CO_3$ in 50 mL of benzene was stirred under argon at 25° C. for 3 h, the mixture was filtered through Celite, and washed with 5 mL of dichloromethane. The filtrate was concentrated to give 0.970 g (99% yield) of methoxybenzoquinone (6): $^1H$ NMR d 6.72 (s, 2H), 5.95 (s, 1H), 3.84 (s, 3H). $^{13}C$ NMR d 187.4, 181.6, 137.1, 134.4, 111.5, 107.6, 56.2. This material was used in the next step without purification.

A solution of 0.70 g (2.90 mmol) of 2 and 1.00 g (7.20 mmol) of 6 in 10 mL of toluene in a sealed tube was heated at 150° C. for 1 day, cooled to 25° C., concentrated to dryness, and column chromatographed on silica gel using a gradient mixture of hexane and ethyl acetate as solvent gave 0.52 g (48% yield) of compounds 5 as a mixture of exo- and endo-(1:1) isomers along with 0.62 g of 6. The exo- and endo-isomers were partially separated by silica gel column and the stereochemistry have not assigned. Compound 5, less polar isomer: MS, m/z 376 (M+), 375. $^1H$ NMR d 7.24–7.18 (m, 2H), 7.08–7.04 (m, 2H), 6.65 (s, 2H, C6,7 Hs), 5.61 (s, 1H), 5.33 (bs, 2H), 3.82 (s, 6H, OMe), 3.48 (s, 3H, OMe), 3.12 (ABd, J=9 Hz, 1H), 3.06 (ABd, J=9 Hz, 1H). More polar isomer: MS, m/z 376 (M+), 375. $^1H$ NMR d 7.40 (m, 2H), 7.16 (m, 2H), 6.60 (ABd, J=8.8 Hz, 1H), 6.56 (Abd, J=8.8 Hz, 1H), 5.65 (s, 1H, =CH), 5.33 (bs, 2H, C9,10 Hs), 3.76 (s, 3H, OMe), 3.73 (s, 3H, OMe), 3.51 (s, 3H, OMe), 3.13 (Abd, J=9 Hz, 1H), 3.08 (Abd, J=9 Hz, 1H). This mixture of compounds was used in the next step.

1,4-Dihydroxy-2,5,8-trimethoxy-9,10-dihydro-9,10-[1,2] benzenoanthracene.

To a solution of 0.77 g (2.0 mmol) of 5 in 30 mL of 1,4-dioxane and 30 mL of water was added 1.12 g (20 mmol)

of KOH. The solution was stirred at 25° C. for 1 h, acidified with 1 N HCl, and extracted three times with dichloromethane. The combined extract was washed with brine, dried (MgSO$_4$), and concentrated to give 0.77 g (100% yield) of 1,4-dihydroxy-2,5,8-trimethoxy-9,10-dihydro-9,10-[1,2]benzenoanthracene: MS, m/z 376 (M+). $^1$H NMR d 7.43 (dd, J=5.5, 3Hz, 1H), 7.38 (dd, J=5.5, 3 Hz, 1H), 6.96 (dd, J=5.5, 3Hz, 2H), 6.51 (s, 2H, C6,7 Hs), 6.29 (s, 1H, C3H), 6.09 (s, 1H), 5.98 (s, 1H), 5.3 (s, 1H, OH), 4.96 (bs, 1H, OH), 3.81 (s, 3H, OMe), 3.805 (s, 3H, OMe), 3.66 (s, 3H, OMe). This compound was used in the next step.

Oxidation of 1,4-Dihydroxy-2,5,8-trimethoxy-9,10dihydro-9,10-[1,2]benzenoanthracene to 4.

To a mixture of 0.77 g (2.0 mmol) of 1,4-dihydroxy-2,5,8-trimethoxy-9,10-dihydro-9,10-[1,2]benzenoanthracene and 0.60 g (4.2 mmol) of sodium sulfate (anhydrous) in 15 mL of dried acetone under argon at 25° C. was added 0.56 g (4.0 mmol) of silver oxide. The mixture was heated under reflux for 6 h, cooled to 25° C., diluted with dichloromethane, and filtered through Celite. The filtrate was concentrated to give 0.77 g of the crude product. Column chromatography on silica gel using a gradient mixture of hexane and ethyl acetate as solvent gave 0.73 g (95% yield) of 4.

2-Methoxy-9,10-dihydro-9,10-[1,2]benzenoanthracene-1,4,5,8-tetraone (7).

To a solution of 0.77 g (2.0 mmol) of 4 in 16 mL of acetonitrile, 26 mL of 1,4-dioxane and 10 mL of water was added 2.0 g (3.6 mmol) of ceric ammonium nitrate at 25° C. The solution was stirred for 12 h, diluted with dichloromethane, and washed with water. The organic layer was dried (MgSO$_4$), concentrated to give the crude product. Recrystallization from ether gave 0.65 g (95% yield) of 7: MS, CI, m/z 345 (M+1), 317 (—CO); $^1$H NMR d 7.48 (dd, J=5.5, 3 Hz, 2H), 7.07 (dd, J=5.5, 3 Hz, 2H), 6.65 (s, 2H, C6,7 Hs), 6.2 (s, 1H), 6.18 (s, 1H), 5.78 (s, 1H, C3H), 3.78 (s, 3H, OMe). $^{13}$C NMR d 182.2, 182.17, 182.0, 176.9, 158.5, 152.5, 151.6, 151.5, 149.6, 142.2, 142.0, 135.4, 135.3, 125.8 (2C), 125.4, 125.3, 105.7, 56.6(OMe), 42.2, 41.9. Anal. Calcd for C$_{21}$H$_{12}$O$_5$: C, 73.25; H, 3.51. Found: C, 73.01; H, 3.80.

2-Bromo-3-methoxy-9,10-dihydro-9,10-[1,2]benzenoanthracene-1,4,5,8-tetraone (1).

To a solution of 0.30 g (0.87 mmol) of 7 in 20 mL of DMF under argon at 25° C. was added 0.16 g (0.87 mmol) of N-bromosuccinimide. After the solution was stirred for 10 h, it was diluted with water, and extracted twice with ethyl acetate. The combined extract was washed with brine, dried (MgSO$_4$), concentrated, and column chromatographed on silica gel using a gradient mixture of hexane and ether as solvent gave 0.29 g (45% yield) of 1: mp 207–210° C.; MS EI, m/z 424 & 422 (1:1, M+), 344 (M—Br), 300, 287, 232, 152, 126; $^1$H NMR d 7.48 (dd, J=5.5, 3 Hz, 2H), 7.09 (dd, J=5.5, 3 Hz, 2H), 6.66 (s, 2H, C6,7 Hs), 6.23 (s, 1H), 6.16 (s, 1H), 4.17 (s, 3H, OMe); $^{13}$C NMR d 182.2 (s, CO), 182.0 (s, CO), 176.2 (s, CO), 175.5 (s, CO), 156.2, 151.6, 151.4, 150.2, 141.8, 135.5, 135.4, 126.2, 126.1, 126.07, 126.0, 125.6, 125.4, 117.2, 61.7 (OMe), 43.0, 42.1. Anal. Calcd for C$_{21}$H$_{11}$BrO$_5$: C, 59.60; H, 2.62. Found: C, 59.33; H, 2.87.

Synthesis of 1 from Bromination of 4 Followed by Oxidation.

To a solution of 90 mg (0.24 mmol) of 4 in 5 mL of DMF under argon at 25° C. was added 52 mg (0.30 mmol) of N-bromosuccinimide (NBS). The solution was stirred at 40° C. for 12 h, diluted with diethyl ether, washed twice with water, and once with brine, dried (MgSO$_4$), and concentrated to give 109 mg (quantitative yield) of 2-bromo-3,5,8-trimethoxy-9,10-dihydro-9,10-[1,2]benzenoanthracene-1,4-dione: $^1$H NMR d 7.44 (dd, J=5.5, 3 Hz, 2H), 7.01 (dd, J=5.5, 3 Hz, 2H), 6.54 (s, 2H, C6,7 Hs), 6.29 (s, 1H), 6.22 (s, 1H), 4.14 (s, 3H, OMe), 3.81 (s, 3H, OMe), 3.79 (s, 3H, OMe). This material was used in next step without purification.

To a solution of 0.109 g (0.240 mmol) of 2-bromo-3,5,8-trimethoxy-9,10-dihydro-9,10-[1,2]benzenoanthracene-1,4-dione in 5 mL of acetonitrile, 6 mL of 1,4-dioxane, and 2 mL of water, was added 0.660 g (1.20 mmol) of ceric ammonium nitrate. The solution was stirred at 25° C. for 6 h, diluted with ether, washed with water, and brine, dried (MgSO$_4$), concentrated, and column chromatographed on silica gel using a gradient mixture of hexane and ether as eluant to give 60 mg (59% yield) of 1.

2-Bromo-3-(methylamino)-9,10-dihydro-9,10-[1,2]benzenoanthracene-1,4,5,8-tetraone (8).

A solution of 0.200 g (0.473 mmol) of 1 and 0.47 mL (0.946 mmol) of methylamine (2.0 M in THF) in 1 mL of THF was stirred under argon at 0° C. for 1 h. The solution was concentrated to dryness, and column chromatographed on silica gel using a gradient mixture of hexane and ethyl acetate as solvent to give 0.132 g (66% yield) of 8: mp. ° C.; MS, CI m/z 424, 422 (~1:1; M+1); $^1$H NMR d 7.48 (dd, J=5, 3Hz, 1H), 7.45 (dd, J=5, 3 Hz, 1H), 7.07 (dd, J=5, 3 Hz, 2H), 6.64 (s, 2H, C6,7 Hs), 6.28 (s, 1H), 6.10 (s, 1H), 5.88 (bs, 1H, NH), 3.33 (d, J=5.6 Hz, 3H, MeN); $^{13}$C NMR (acetone-d$_6$) d 183.33, 183.3, 178.2, 170.9, 154.4, 152.3, 152.0, 148.0, 147.0, 143.7, 143.5, 136.4, 136.3, 126.5 (2C), 126.0, 125.7, 125.0, 44.3, 42.9, 33.2. Anal. Calcd for C$_{21}$H$_{12}$BrNO$_4$: C, 59.74; H, 2.86. Found: C, 59. 74; H, 2.76.

2-Bromo-3-methoxy-6-(dimethylamino)-9,10-dihydro-9,10-[1,2]benzenoanthracene-1,4,5,8-tetraone (9) and 2-Bromo-3-methoxy-7-(dimethylamino)-9,10-dihydro-9,10-[1,2]benzenoanthracene-1,4,5,8-tetraone (10).

To a solution of 0.200 g (0.473 mmol) of 1 in 2 mL of THF under argon at 0° C., was added 0.24 mL (0.473 mmol) of dimethylamine (2.0 M in THF). After stirring at 0° C. for 2 h, the reaction solution was concentrated to dryness, and column chromatographed on silica gel using a mixture of benzene and ethyl acetate (10:1) as solvent to give 0.099 g (48% yield) of 9 (less polar isomer; the regiochemistry has not been determined) and 0.098 g (48% yield) of 10 (more polar).

Less polar isomer: MS, CI, m/z 468, 466 (~1:1; M+1); $^1$H NMR d 7.47–7.43 (m, 2H, Ar—H), 7.05~7.02 (m, 2H, Ar—H), 6.22 (s, 1H), 6.14 (s, 1H), 5.38 (s, 1H, C7H), 3.80 (s, 3H, OMe), 3.11 (s, 6H, Me$_2$N). $^{13}$C NMR d 181.4 (2C), 181.2 (2C), 153.7, 150.4, 149.3, 144.1, 143.9, 142.2, 141.8, 139.1, 127.1, 125.5, 125.3, 124.7, 124.2, 102.5, 61.1, 42.8, 42.7, 42.0, 41.4.

More polar isomer: MS, CI, m/z 468, 466 (~1:1; M+1); $^1$H NMR d 7.48~7.42 (m, 2H, Ar—H), 7.04~7.01 (m, 2H, Ar—H), 6.24 (s, 1H), 6.16 (s, 1H), 5.39 (s, 1H, C7H), 3.79 (s, 3H, OMe), 3.10 (s, 6H, Me$_2$N). $^{13}$C NMR d 181.6 (2C), 181.4 (2C), 154.0, 150.7, 149.6, 144.9, 144.0, 142.6, 141.5, 139.8, 127.2, 125.6 (2C), 125.0, 124.3, 102.4, 61.2, 43.0 (2C), 42.0, 41.9. HRMS m/z 466.0285 (466.0290, calcd for C$_{23}$H$_{17}$Br NO$_5$, M–H$^+$).

2-Bromo-3-[2-(ethoxycarbonyl)ethylamino]-9,10-dihydro-9,10-[1,2]benzenoanthracene-1,4,5,8-tetraone (11).

To a mixture of 5.70 mg (0.236 mmol) of NaH (prewashed with distilled ether) in 2 mL of DMF under argon at 0° C. was added 36.3 mg (0.236 mmol) of b-alanine ethyl ester hydrochloride (ethyl 3-aminopropanoate hydrochloride). The solution was stirred at 0° C. for 30 min, cooled to –46° C., and a solution of 100 mg (0.236 mmol)

of 1 in 1 mL of DMF was added via cannula. The solution was stirred at −46° C. for 6 h, diluted with a mixture of ethyl acetate and benzene (1:1), washed twice with water, brine, dried (Na$_2$SO$_4$), concentrated, and column and benzene (1:1), washed twice with water, brine, dried (Na$_2$SO$_4$), concentrated, and column give 55 mg (46% yield) of 11 and 30 mg (30% recovery) of 1. Compound 11: mp. 119~121° C.; MS, m/z 510, 508 (~1:1; M+1), 422, 420 (1:1); $^1$H NMR d 7.45~7.42 (m, 2H, Ar—H), 7.08~7.04 (m, 2H, Ar—H), 6.65 (s, 2H, C6,7 Hs), 6.3 (bs, 1H, NH), 6.27 (s, 1H), 6.10 (s 1H), 4.16 (q, J=7 Hz, 2H, OCH$_2$), 4.03 (q, J=6 Hz, 2H, CH$_2$N), 2.64 (t, J=6 Hz, 2H, CH$_2$CO), 1.26 (t, J=7 Hz, 3H, CH$_3$); $^{13}$C NMR d 184.0, 183.6, 182.6, 182.3, 177.3, 171.7, 154.5, 151.8, 151.7, 147.4, 144.3, 142.4, 142.2, 135.8, 135.5, 126.2, 126.1, 125.9, 125.3, 61.3, 43.7, 42.2, 40.5, 35.4, 14.4. Anal. Calcd. For C$_{25}$H$_{18}$BrNO$_6$: C, 59.07; H, 3.57. Found: C, 58.69; H, 3.72.

2-Bromo-3-[2-(t-butoxycarbonyl)ethylamino]-9,10-dihydro-9,10-[1,2]benzenoanthracene-1,4,5,8-tetraone (12).

To a mixture of 12.0 mg (0.496 mmol) of NaH (prewashed with distilled ether) in 2 mL of DMF under argon at 0° C. was added 90.0 mg (0.496 mmol) of b-alanine t-butyl ester hydrochloride. The solution was stirred at 0° C. for 30 min, cooled to −46° C., and a solution of 201 mg (0.496 mmol) of 1 in 1 mL of DMF was added via cannula. The solution was stirred at −46° C. for 8 h, diluted with a mixture of ethyl acetate and benzene (1:1), washed twice with water, brine, dried (Na$_2$SO$_4$), concentrated, and column chromatographed on silica gel using a mixture of hexane and ethyl acetate (10:1) as solvent to give 165 mg (62% yield) of 12: mp. 171~173° C.; MS, m/z 538, 536 (~1:1; M+1), 482, 480 (1:1); $^1$H NMR d 7.45~7.42 (m, 2H Ar—H), 7.08~7.04 (m, 2H, Ar—H), 6.64 (s, 2H, C6,7 Hs), 6.27 (s, 1H), 6.22 (bs, 1H, NH), 6.22 (bs, 1H, NH), 6.10 (s, 1H), 4.00 (q, J=6.7 Hz, 2H, CH$_2$N), 2.55 (t, J=6.7 Hz, 2H, CH$_2$CO), 1.44 (s, 9H, CH$_3$); $^{13}$C NMR d 182.3, 182.0, 177.0, 173.5, 170.6, 154.1, 151.4, 151.37, 147.0, 144.2, 142.1, 141.9, 135.4, 135.2, 128.8, 125.8, 125.76, 125.5, 125.0, 81.5, 43.5, 41.9, 40.5, 36.2, 28.0 (3C). Anal. Calcd for C$_{27}$H$_{22}$BrNO$_6$: C, 60.46; H, 4.13. Found: C, 60.75; H, 4.39.

N-(2-Bromo-9,10-dihydro-1,4,5,8-tetraoxo-9,10-[1,2]benzenoanthracene-3-yl)-3-aminopropanoic acid (13).

A solution of 0.100 g (0.187 mmol) of 12 and 0.2 mL (2.60 mmol) of trifluoroacetic acid in 5 mL of dichloromethane was stirred at 0° C. for 1 h and then at 25° C. for 2 h. The solution was concentrated to dryness, and recrystallized from benzene to give 0.090 g (100% yield) of purple solids: mp. 149~151° C.; MS, m/z 482, 480 (~1:1; M+1), 422, 420 (1:1); $^1$H NMR d 7.49~7.46 (m, 2 H), 7.08~7.06 (m, 2H), 6.64 (s, 2H), 6.27 (s, 1H), 6.22 (bs, 1H, NH), 6.10 (s, 1H), 4.04 (q, J=6 Hz, 2H, CH$_2$N), 3.40 (bs, 1H, OH), 2.73 (t, J=6 Hz, 2H, CH$_2$); $^{13}$C NMR (CD$_3$OD) d 182.8, 182.77, 177.2, 174.2, 174.1, 151.6, 151.4, 147.6, 145.6, 142.9, 142.6, 137.9, 135.4, 129.0, 128.9, 128.2, 128.18, 126.1, 125.2, 43.8, 42.4, 42.3, 34.8. Anal. Calcd for C$_{23}$H$_{14}$BrNO$_6$: C, 57.52; H, 2.94. Found: C, 56.72; H, 2.88.

Preparation of TT24:

To 20 mL of THF solution, 1 g (0.022 mol) of dimethylamine gas (from a gas cylinder purchased from Linde Company) was added. A 1.1 M of dimethylamine in THF was resulted. To a cold (0° C.) solution of 0.081 g (0.19 mmol) of triptycene bisquinone 1 in 2 mL of THF under argon was added 0.17 mL (0.19 mmol) of dimethylamine. The solution turn to purple immediately and was stirred at 0° C. for 10 min. The solvent was removed on a rotary evaporator and then under vacuum and the crude product was column chromatographed on silica gel using a gradient mixture of hexane and ethyl acetate as the eluent to give compounds 1,2, and TT24.

Compound TT24: $^1$H NMR (CDCl$_3$) δ 7.44–7.40 (m, 2H), 7.03 (m, 2H), 6.27 (s, 1H), 6.15 and 6.14 (2 s, 1H), 5.69 (q, J=5.6 Hz, NH), 5.26 (s, 1H), 3.80 & 3.79 (2s, 3H, OMe), 2.79 (d, J=5.6 Hz, 3H, NMe); $^{13}$C NMR (CDCl$_3$) δ 181.7, 181.6, 179.5, 156.2, 147.8, 147.6, 143.9, 143.8, 143.6, 142.3, 141.8, 141.3, 139.6, 139.1, 131.2, 126.9, 125.52, 125.49, 125.46, 125.4, 124.8, 124.75, 124.3, 124.2, 102.3, 95.8, 95.7, 61.1, 60.4, 42.2, 41.9, 41.3, 41.0, 29.3 (2C).

Synthesis of Other N Analogs and S Analogs

As illustrated in Scheme 17, nitrogen analog 1 has been prepared. Treatment of TT13 with 1 equivalent each of L-lysine hydrochloric acid and sodium hydride in a 1:1 mixture of THF and DMF under argon at room temperature gave amino acid analog 1 which is a water soluble drug.

Scheme 19 outlines the synthetic route to prepare nitrogen analogs 2–4. Treatment (Kenani, A.; Bailly, C.; Helbecque, N.; Houssin, R.; Bernier, J. -L.; Henichart, J. -P. *Eur. J. Med. Chem.* 1989, 24, 371–377.) of D-galactosamine hydrochloride (commercially available) with sodium hydroxide and di-t-butylcarbonate in 1,4-dioxane and water, followed by protection of the hydroxyl function with excess of acetyl anhydride in pyridine, and removal of the Boc protecting group with hydrochloric acid in 1,4-dioxane produces amine 6. Addition of 6 with TT13 in THF at −40° C. followed by removal of the acetoxy protecting group affords nitrogen analog 2.

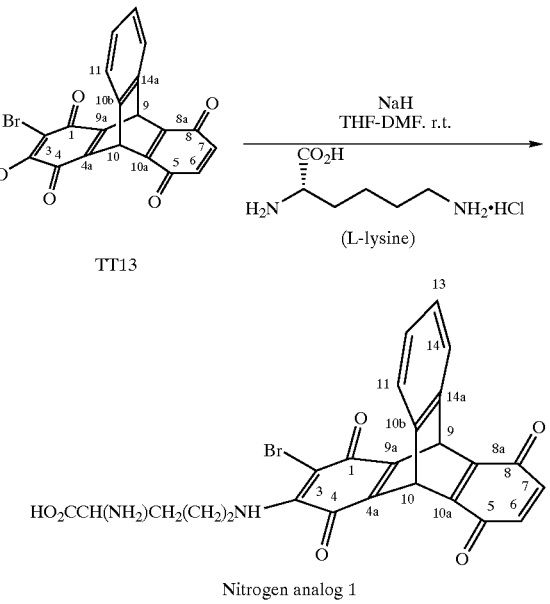

Similarly, glucosamine hydrochloride car, be used to prepare glucosamine analog (of 2; instead of galactosamine analog).

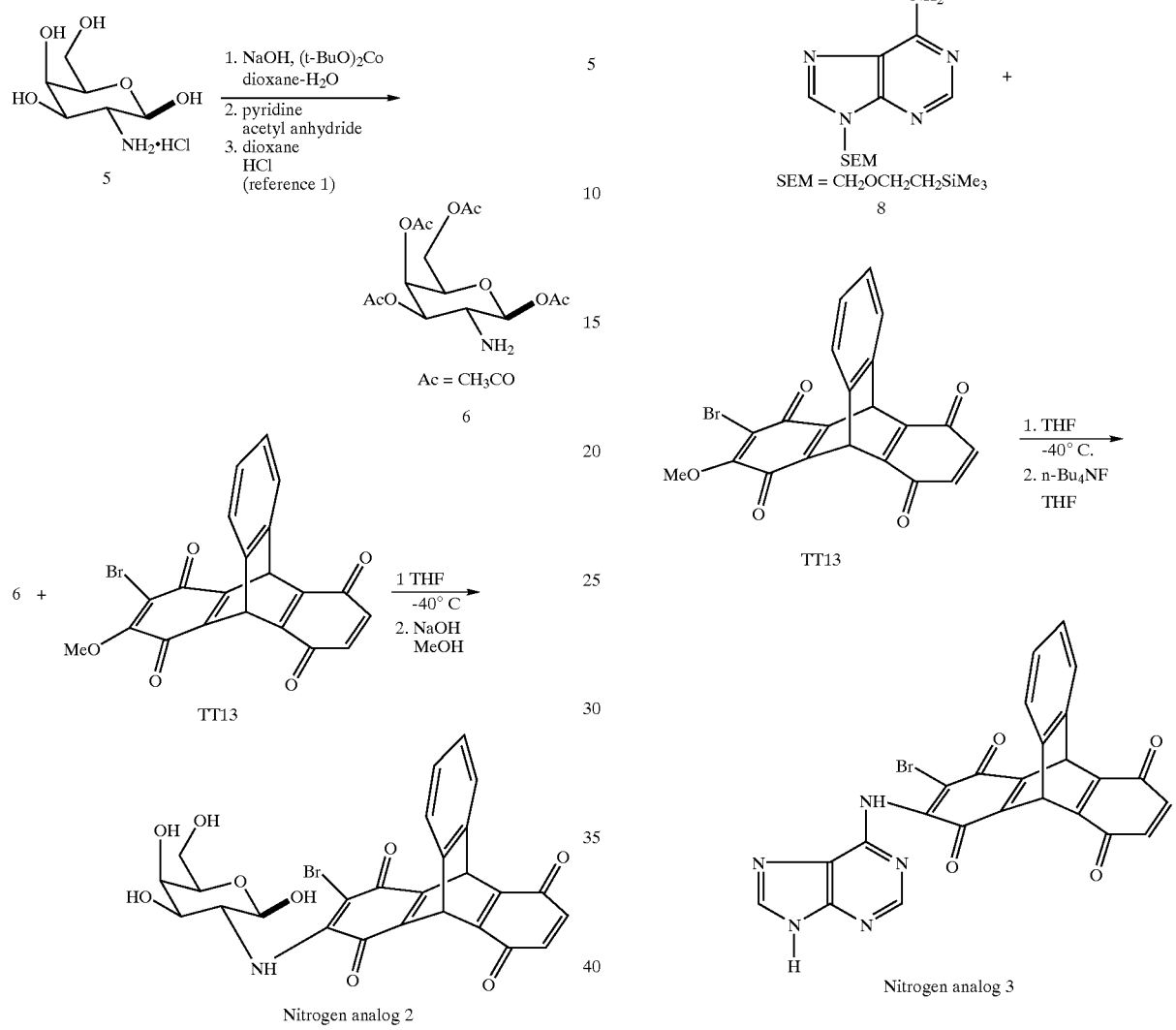

Syntheses of nitrogen analogs 3 and 4 are depicted in Scheme 20. Protection of N-9 of adenine (7) with (trimethylsilyl)ethyl chloromethyl ether (SEM-Cl) and sodium hydride in DMF produces compound 8. Addition of 8 with TT3 in THF at −40° C. followed by removal of the SEM protecting group with tetra-n-butylammonium fluoride in THF furnishes nitrogen analog 3. Direct treatment of adenine and catalytic amount of sodium hydride in THF at −40° C. gives nitrogen analog 4. The N9 hydrogen of adenine (7) is more acidic than that of C6 amine group, hence, N9 nitrogen should react with TT3.

Sulfur analogs: Uses of thiol containing amino acid such as N-protected L-cysteine provides sulfur analog (Scheme 21). Hence, addition of N-Boc cysteine and sodium hydride in DMF-THF followed by trifluoroacetic acid (removal of the Boc protecting group) will afford sulfur analog.

Scheme 21

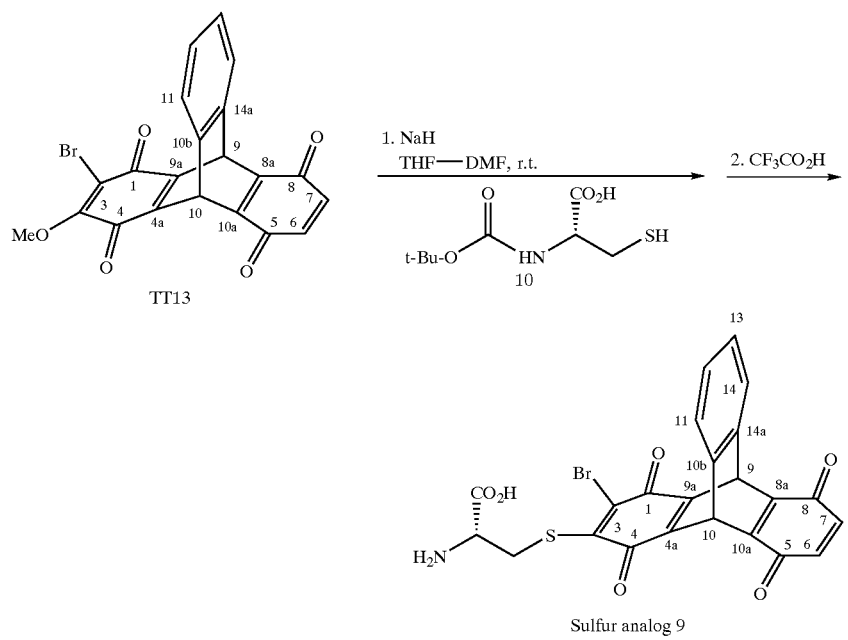

Sulfur analog 9

The above four nitrogen analogs and the sulfur analog are water soluble materials. Other nitrogen and sulfur analogs are prepared by methods known to one of ordinary skill in the art, In using substitutions which are known to one of ordinary skill in the art.

Compounds of this invention other than those particularly shown may be prepared without undue experimentation by those skilled in the art of synthetic chemistry by methods analogous to, those specifically disclosed herein or in publications and patent applications incorporated by reference or by methods known in the art.

Although the description above contains many specificities these should not be construed as limiting the scope of the invention, but merely providing illustrations of some of the presently preferred embodiments of the invention. Thus, the scope of the invention should be determined by the appended claims and their legal equivalents, rather than by the examples given. All references cited herein are incorporated by reference to the extent not inconsistent with the disclosure herein.

Literature References in Synthesis Section:
1. Iwamura, H.; Maino, K. 5,8-Dihydroxy-9,10-dihydro-9,10-[1,2]benzenoanthracene-1,4-dione. An intramolecular triptycene quinhydrone. *J. Chem. Soc. Chem. Commun.* 1978, 720–721.
2. Lipczynska-Kochany, E.; Iwamura, H. Charge-transfer complexation with a new class of electron acceptors made of triptycenequinone unit. *Chem. Lett.* 1982, 1075–1078.
3. (a) Quast, H.; Fuchsbauer, H. -L. ESR-spektrosckopischer nachweis intramolekularer wechselwirkungen in radikalkationen von poly(a-methoxy)triptycenen. *Chem. Ber.* 1986, 119, 1016–1038. (b) Quast, H.; Fuchsbauer, H. -L. Intramolekulare wechselwirkungen in radikalkationen von di-und tetra(a-methoxy)-9,10-dihydro-9,10-ethanoanthracen. *Chem. Ber.* 1986, 119, 2414–2429. (c) Patney, H. K. A general and simple route to the synthesis of triptycenes. *Synthesis* 1991, 694–696.
4. Russell, G. A.; Suleman, N. K. Radical Anions of Triptycene Bis- and Tris(quinones). *J. Am. Chem. Soc.* 1981, 103, 1560–1561.
5. (a) Daub, J.; Jakob, L.; Salbeck, J. Chirale elektronentransfer-aktive chinone mit triptycen-teilstrukturen: synthesekonzeption und eigenschaften. *Chem. Ber.* 1988, 121, 2187–2194. (b) Siegfried, H.; Sinzger, K.; Bau, R.; Metzenthin, T.; Salbeck, J. 1,4,5,8-Tetraoxo-1,4,5,8-tetrahydrothianthrene: synthesis, structure, and spectroelectrochemical properties. *Chem. Ber.* 1993, 121, 465–471.
6. Criswell, T. R.; Klanderman, B. H. Studies related to the conversion of 9,10-anthraquinones to anthracenes. *J. Org. Chem.* 1974, 39, 770–774.
7. Hamon, D. P. G.; Spurr, P. R. Reductive elimination of bromine from 2,3-disubstituted 1,4-dibromo-2-butenes by iodide ion: a convenient route to 2,3-bis[iodomethyl]-1,3-butadiene and related compounds. *Syntheses* 1981, 873–874.
8. Hamon, D. P. G.; Spur, P. R. *J. Chem. Soc. Chem. Commun.* 1981, 873–4.

What is claimed is:
1. A triptycene analog comprising a compound of formula:

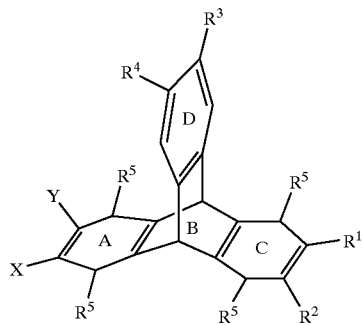

wherein
X is selected from the group consisting of: H, R, SR and $NR_2$;

Y is selected from the group consisting of: halogen, R, NR₂, SR and H;

R and $R^{1-2}$ are independently selected from the group consisting of: H, halogen, OR, and hydrocarbyl;

$R^{3-4}$, independently of one another, are selected from the group consisting of: H, bromine, R, SR, and NR₂;

$R^5$, independently of other $R^5$s, is selected from the group consisting of: =O, =N—OH and =CHR; and reduced forms thereof, wherein in reduced forms, either ring A or ring C or both is replaced with

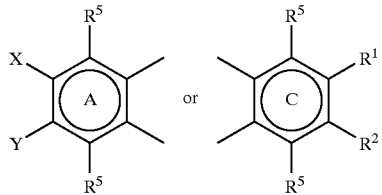

and wherein reduced form, each $R^5$ is independently H, C1–C8 alkyl or —OR;

and pharmaceutically acceptable salts of the forgoing, as well as optical isomers thereof;

wherein when all of $R^5$ are =O, at least one of X, Y, $R^1$—$R^4$ is not H.

2. The triptycene analog of claim 1 having the formula:

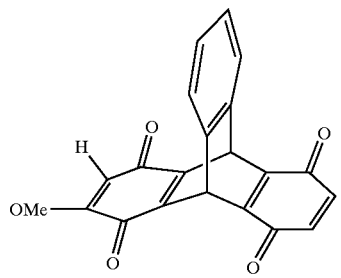

3. The triptycene analog of claim 1 having the formula:

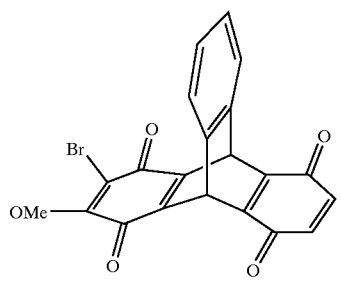

4. The triptycene analog of claim 1, wherein:

X is selected from the group consisting of: H, OMe and CO₂Me;

Y is selected from the group consisting of: H, Br, and OMe;

$R^1$, $R^2$, $R^3$ and $R^4$ are all H; and $R^5$ is, independently of other $R^5$s, selected from the group consisting of: OH, OMe, =O, and H.

5. A triptycene analog having the formula:

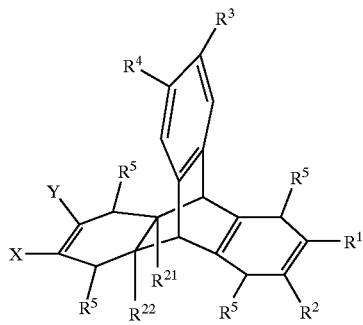

wherein
X is selected from the group consisting of: H, R, SR and NR₂
Y is selected from the group consisting of: halogen, NR₂, R, SR and H;
R and $R^{1-2}$, are independently selected from the group consisting of: H, halogen, OR, and hydrocarbyl;
$R^{3-4}$, independently of one another, are selected from the group consisting of: H, bromine, R, SR, and NR₂;
$R^5$, independently of other $R^5$s, is selected from the group consisting of: =O, =N—OH, and =CHR;
$R^{21}$ and $R^{22}$ are independently selected from the group consisting of: H, R, and OR; and
reduced forms thereof and pharmaceutically acceptable salts of the foregoing, as well as optical isomers thereof.

6. A triptycene analog having the formula:

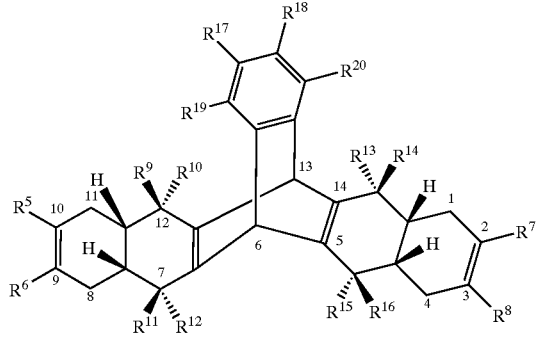

wherein
$R^5$ is selected from the group consisting of: R, halogen, NR₂, SR, and H;
$R^6$ is selected from the group consisting of: H, R, SR and NR₂;
$R^7$ and $R^8$ are independently selected from the group consisting of: H, halogen, and hydrocarbyl;
$R^{17}$ and $R^{18}$ are independently are selected from the group consisting of: H, bromine, R, SR, and NR₂;
$R^{19}$ and $R^{20}$ are, independently of one another, H, R, or OR;
($R^9$ and $R^{10}$) and ($R^{11}$ and $R^{12}$) and ($R^{13}$ and $R^{14}$) and ($R^{15}$ and $R^{16}$) are independently together =O or are independently H or —OR;
R is selected from the group consisting of: H, halogen, OR, and hydrocarbyl; and reduced forms thereof;
and pharmaceutically acceptable salts of the foregoing, as well as optical isomers thereof.

7. A method of making a compound of claim 1, comprising: heating an optionally substituted anthracene with an optionally substituted quinone with silver oxide.

8. The method of claim 7, further comprising adding zinc iodide.

9. The method of claim 7, wherein the optionally substituted anthracene has the formula:

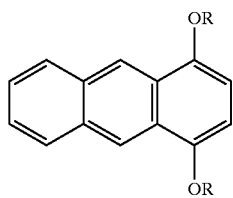

and the optionally substituted quinone has the formula:

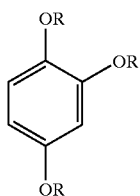

where R is H or hydrocarbyl.

10. A method of brominating a triptycene derivative of formula (I):

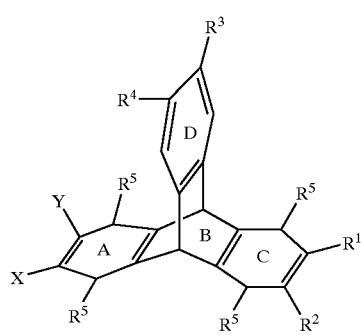

wherein X is selected from the group consisting of: H, R, SR and $NR_2$;

Y is selected from the group consisting of: halogen, R, $NR_2$, SR and H;

R and $R^{1-2}$ are independently selected from the group consisting of: H, halogen, OR, and hydrocarbyl;

$R^{3-4}$, independently of one another, are selected from the group consisting of: H, bromine, R, SR, and $NR_2$;

$R^5$, independently of other $R^5$s, is selected from the group consisting of: =O, =N—OH and =CHR; and reduced forms thereof, wherein in reduced forms, either ring A or ring C or both is replaced with

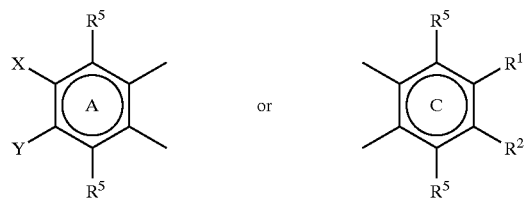

and wherein in reduced forms, each $R^5$ is independently H, C1–C8 alkyl or —OR;

and pharmaceutically acceptable salts of the foregoing, as well as optical isomers thereof;

wherein when all of $R^5$ are =O, at least one of X, Y, $R^1$—$R^4$ is not H; and wherein either:
(a) Y is a hydrogen and X is a methoxy group;
(b) $R^1$ is a hydrogen and $R^2$ is a methoxy group; or
(c) $R^2$ is a hydrogen and $R^1$ is a methoxy group, by reacting a triptycene derivative of formula (I) with N-bromosuccinimide, wherein the Y, $R^1$ or $R^2$ that is hydrogen is replaced with a bromine.

11. The method of claim 10, wherein the triptycene derivative is:

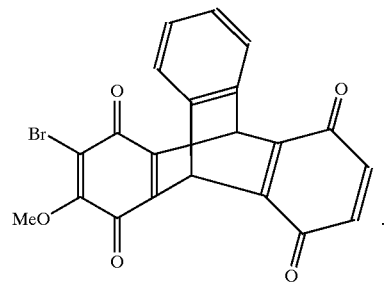

12. A triptycene analog of claim 1,
wherein at least one of X, Y, $R^1$ and $R^2$ is selected from the group consisting of: a nitrogen containing group, a water soluble group, and a sulfur containing group.

13. The compound of claim 12, wherein X is —$NR_2$.

14. The compound of claim 12, wherein $R^2$ is —$NR_2$.

15. The compound of claim 14, wherein $R^2$ is —$NMe_2$.

16. The compound of claim 12, wherein at least one of X, Y, $R^1$ and $R^2$ is selected from the group consisting of: amine, amino acid and amine sugar.

17. The compound of claim 12, wherein X is —NH—$(CH_2)_n$—$CO_2R$, where n is an integer from 0 to 8, and R is as defined in claim 12.

18. The compound of claim 17 wherein R is H.

19. The compound of claim 12, wherein one or more of X, Y, $R^1$ and $R^2$ contains an optionally substituted nitrogen containing hydrocarbyl group.

20. The compound of claim 19, wherein the optionally substituted nitrogen containing hydrocarbyl group is a fused ring structure.

21. The compound of claim 12, wherein X is a sulfur containing group.

22. The compound of claim 21, wherein the sulfur containing group also contains one or more N atoms.

23. The compound of claim 12 having the formula:
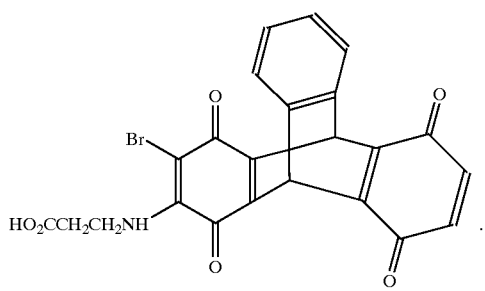
24. The compound of claim 12 having the formula:
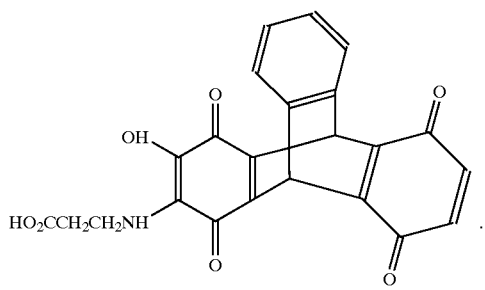
25. The compound of claim 12 having the formula:
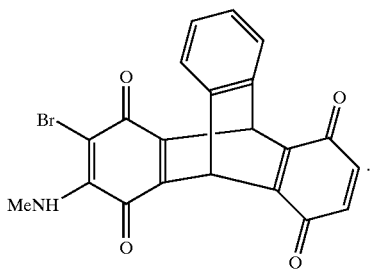
26. The compound of claim 12 having the formula:
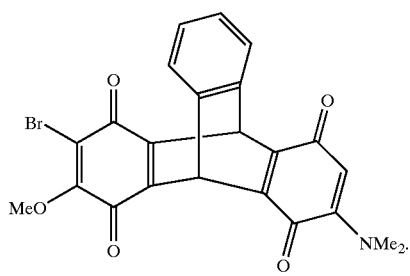
27. The compound of claim 12 having the formula:
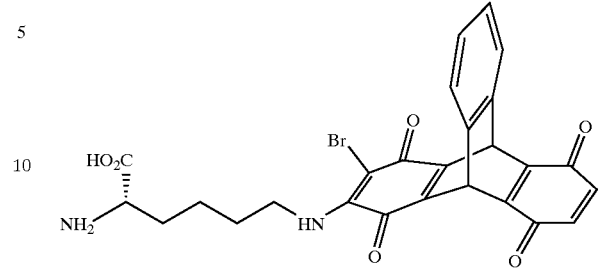
28. The compound of claim 12 having the formula:
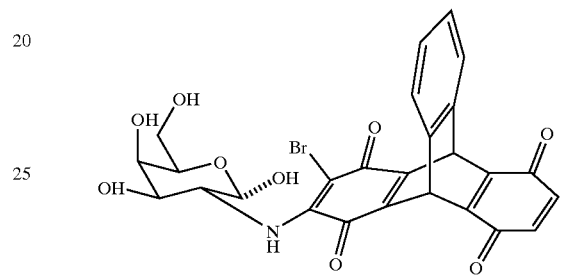
29. The compound of claim 12 having the formula:
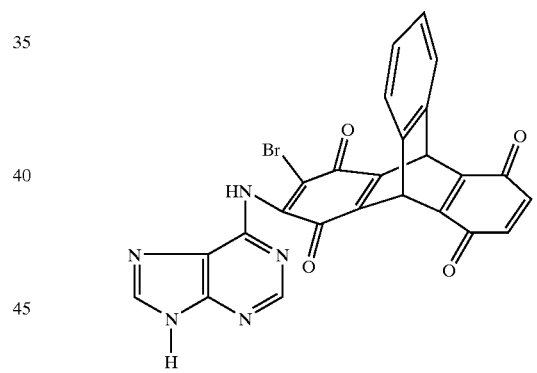
30. The compound of claim 12 having the formula:
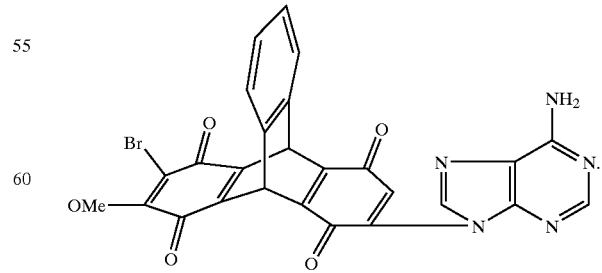

31. The compound of claim 12 having the formula:

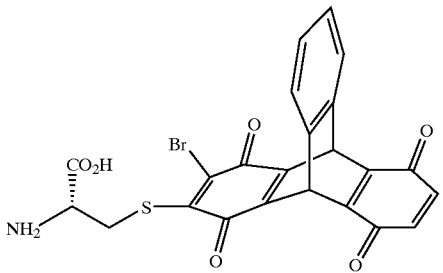

32. The triptycene analog of claim 12 having the formula:

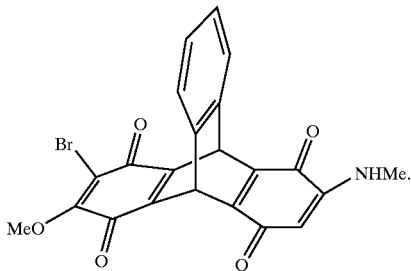

33. A triptycene analog comprising a compound of formula:

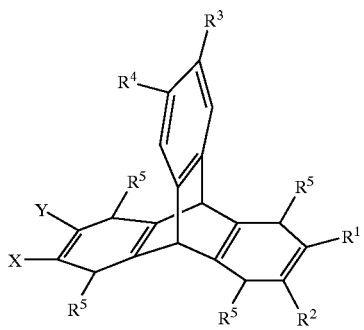

wherein X is —NW(CW$_2$)$_n$Z, where the Ws are independently selected from the group consisting of: H, C1–C8 alkyl, and C1–C8 alkenyl; n is an integer from 1 to 8; and Z is selected from the group consisting of: R, COR, COOR, CONR$_2$, OOCR and NRCOR;

Y is selected from the group consisting of: halogen, C1–C8 alkyl, C1–C8 alkenyl, OR, NR$_2$, SR, H, COR, OCOR and NRCOR;

R and R$^{1-2}$, are independently selected from the group consisting of: H, OR, and hydrocarbyl;

R$^{3-4}$, independently of one another, are selected from the group consisting of: H, OR, SR, and NR$_2$;

R$^5$, is =O; and reduced forms thereof and pharmaceutically acceptable salts of the foregoing, as well as optical isomers thereof.

34. The triptycene analog of claim 5, wherein at least one of X, Y, R$^1$ and R$^2$ is selected from the group consisting of: a nitrogen containing group, a water soluble group, and a sulfur containing group.

35. The compound of claim 34 wherein at least one of R$^{21}$ and R$^{22}$ is —CO$_2$R.

36. The compound of claim 12 which blocks nucleoside transport, induces DNA fragmentation, inhibits nucleic acid synthesis, inhibits protein synthesis, decreases the proliferation of cancer cells, or decreases the viability of cancer cells.

37. The triptycene analog of claim 6, wherein at least one of R$^5$, R$^6$, R$^7$ and R$^8$ is selected from the group consisting of: a nitrogen containing group, a water soluble group, and a sulfur containing group.

38. A method of making a nitrogen-containing compound of claim 12, comprising: reacting a triptycene derivative of formula:

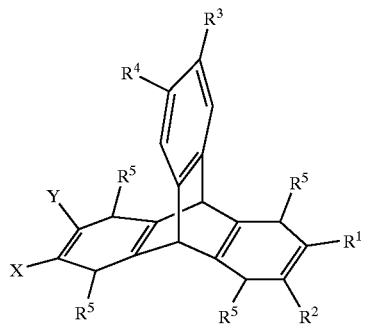

wherein
R$^{3-4}$, independently of one another, are selected from the group consisting of: H, bromine, R, SR and NR$_2$;
R$^5$, independently of other R$^5$s, is selected from the group consisting of: =O, and =N—OH, and =CHR;
Y is Br, and X is —OR;
R and R$^{1-2}$ are independently selected from the group consisting of: H, OR, and hydrocarbyl; and reduced forms thereof;
with a primary or secondary amine.

39. A triptycene analog of formula:

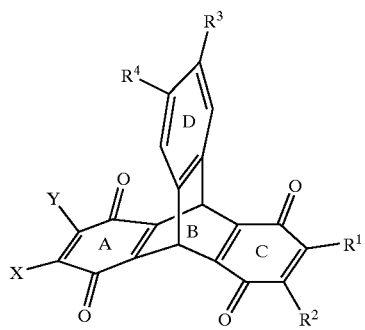

and the reduced forms thereof, wherein in said reduced forms, either ring A or ring C or both is reduced to

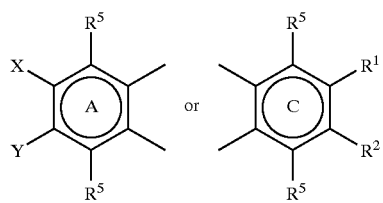

wherein all but one of X, Y, R1 and R2 is independently H, C1–C6 alkyl, C1–C6 alkenyl, OR, SR or NR2 wherein each R is independently H or C1–C6 alkyl and the other R1 or R2 is a solubilizing group; and each R5 is independently H, C1–C6 alkyl or OR.

40. The triptycene analog of claim 39, wherein the solubilizing group is of the formula:

NR(CR$_2$)$_n$X wherein X is a sugar, R, COR, COOR, CONR$_2$, OOCR and NRCOR; R is independently selected from the group consisting of: H, C1–C8 alkyl and C1–C8 alkenyl; n is an integer from 1 to 8.

* * * * *

UNITED STATES PATENT AND TRADEMARK OFFICE
CERTIFICATE OF CORRECTION

PATENT NO. : 6,828,450 B2  Page 1 of 4
APPLICATION NO. : 09/974716
DATED : December 7, 2004
INVENTOR(S) : Hua et al.

It is certified that error appears in the above-identified patent and that said Letters Patent is hereby corrected as shown below:

Title Page:

Under heading "References Cited" under "U.S. PATENT DOCUMENTS", please add the following
--5,958,970   9/1999   Hua et al…………….....514/555--.

In the Specification:

Column 5, line 52, replace "TT2:X = PMe, Y = H" with -- TT2:X = OMe, Y = H --.

Column 6, lines 28-50, move the structures

"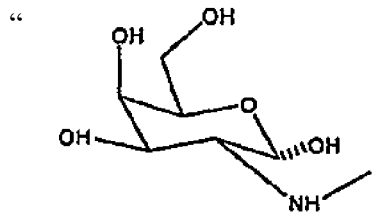

N analog 3: Y = Br, X =

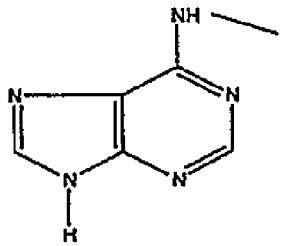

N analog 4: X = OMe, Y = Br, $R^2$ =

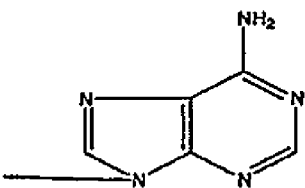

S analog 9: Y = Br, X = $SCH_2CH(CO_2H)NH_2$ " to the bottom of column 5 after X =.

UNITED STATES PATENT AND TRADEMARK OFFICE
CERTIFICATE OF CORRECTION

PATENT NO.       : 6,828,450 B2  
APPLICATION NO.  : 09/974716  
DATED            : December 7, 2004  
INVENTOR(S)      : Hua et al.

It is certified that error appears in the above-identified patent and that said Letters Patent is hereby corrected as shown below:

Column 7, lines 13-27, replace the following structure

"
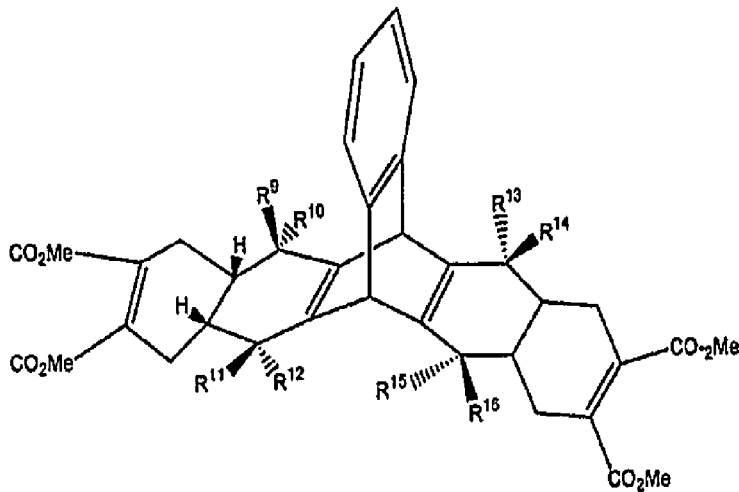

TT4: $R^9 = R^{10} = R^{11} = R^{12} = R^{13} = R^{14} = R^{15} = R^{16} = O$  
TT12: $R^9 = R^{11} = R^{13} = R^{15} = H$, $R^{10} = R^{12} = R^{14} = R^{16} = OH$ "

with --

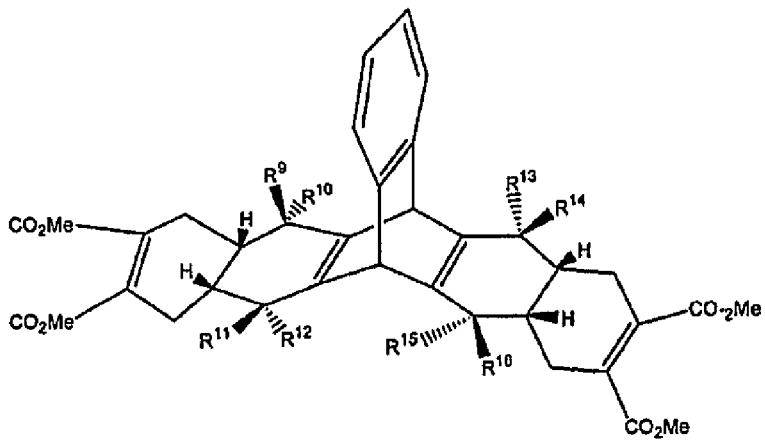

TT4: $R^9 = R^{10} = R^{11} = R^{12} = R^{13} = R^{14} = R^{15} = R^{16} = O$  
TT12: $R^9 = R^{11} = R^{13} = R^{15} = H$, $R^{10} = R^{12} = R^{14} = R^{16} = OH$ --.

UNITED STATES PATENT AND TRADEMARK OFFICE
CERTIFICATE OF CORRECTION

PATENT NO.      : 6,828,450 B2
APPLICATION NO. : 09/974716
DATED           : December 7, 2004
INVENTOR(S)     : Hua et al.

It is certified that error appears in the above-identified patent and that said Letters Patent is hereby corrected as shown below:

Column 15, line 52, replace "combinations thereof" with -- combinations thereof. --.

Column 34, lines 57-65, Scheme 3, insert -- + -- after the structure.

Column 37, lines 23-63, Scheme 6, replace all structures shown in Scheme 6 with --

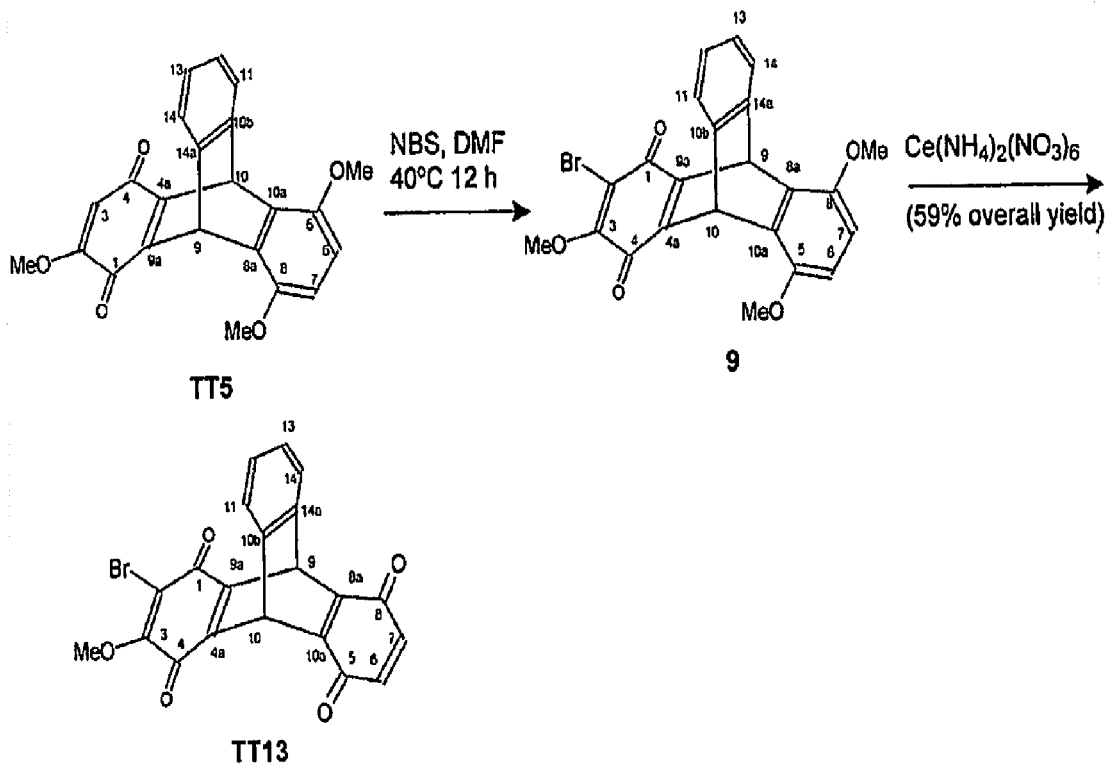

--.

Column 40, line 24, underneath the arrow after structure 15, insert -- toluene, reflux 5 h --.

Column 41, line 32, Scheme 10, under the first structure, insert -- TT1 --.

Column 53, line 11, replace "3C4a," with -- C4a, --.

UNITED STATES PATENT AND TRADEMARK OFFICE
CERTIFICATE OF CORRECTION

PATENT NO. : 6,828,450 B2
APPLICATION NO. : 09/974716
DATED : December 7, 2004
INVENTOR(S) : Hua et al.

It is certified that error appears in the above-identified patent and that said Letters Patent is hereby corrected as shown below:

Column 66, lines 38-64, Scheme 17, replace the entire Scheme with the following

--

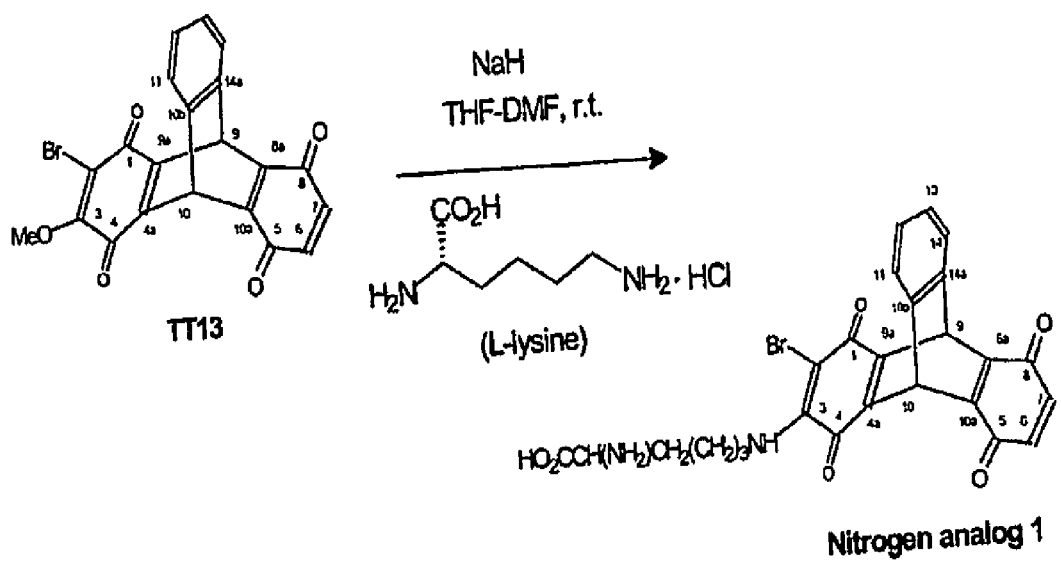

--.

Signed and Sealed this

Twenty-seventh Day of February, 2007

JON W. DUDAS
*Director of the United States Patent and Trademark Office*